US007074911B2

(12) United States Patent
Xu et al.

(10) Patent No.: US 7,074,911 B2
(45) Date of Patent: Jul. 11, 2006

(54) ENDOGENOUS GRANZYME B IN NON-IMMUNE CELLS

(75) Inventors: Hong-Ji Xu, Houston, TX (US);
Shi-Xue Hu, Houston, TX (US);
Gordon B. Mills, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 136 days.

(21) Appl. No.: 10/670,135

(22) Filed: Sep. 24, 2003

(65) Prior Publication Data

US 2004/0126846 A1 Jul. 1, 2004

Related U.S. Application Data

(60) Provisional application No. 60/413,591, filed on Sep. 25, 2002.

(51) Int. Cl.
*C12N 15/57* (2006.01)
*C12N 9/64* (2006.01)
*C12N 15/79* (2006.01)

(52) U.S. Cl. .................. 536/23.2; 435/69.1; 435/252.3; 435/320.1

(58) Field of Classification Search ................. 536/23.2; 435/69.1, 252.3, 320.1
See application file for complete search history.

(56) References Cited

U.S. PATENT DOCUMENTS 5,858,758 A * 1/1999 Hillman et al. ............. 435/226
5,965,711 A * 10/1999 Hillman et al. .......... 530/387.9

(Continued)

FOREIGN PATENT DOCUMENTS

WO    WO 1991/10685 A  *  7/1991
WO    WO 99/43840 A2  *  9/1999

(Continued)

OTHER PUBLICATIONS

Caputo, A., et al., 1990, "Nucleotide sequence and genomic organization of a human T lymphocyte serine protease gene", Journal of Immunology, vol. 145, No. 2, pp. 737–744.*

(Continued)

*Primary Examiner*—Ponnathapula Achutamurthy
*Assistant Examiner*—William W. Moore
(74) *Attorney, Agent, or Firm*—Vinson & Elkins LLP

(57) ABSTRACT

The instant invention relates to the determination that constitutively nearly silent GrB locus in human breast carcinoma and osteosarcoma cells activated upon retinoblastoma protein (pRB)-induced growth arrest owing to the usage of an alternative promoter/transcription start site. Cloned novel cDNA from the locus adds 34 amino acid residues to the N-terminus of GrB zymogen. The alternate product has been designated as GrB-NIC. Tumor cells with accumulated endogenous GrB-NIC, whose mature form was identical to lymphocyte GrB but with a distinctive glycosylation pattern, undergoes post-growth-arrest apoptosis that occurs concurrently with pRB cleavage, and are capable of inducing rapid apoptosis of bystander pRB$^-$ tumor cells. Expression of GrB-NIC is also observed in malignant cells of other types as well as in normal non-immune cells upon cell differentiation, especially in differentiating and differentiated neural cells. GrB-NIC plays a physiological role in embryonic, and particularly in early neuronal development. The disclosure further provides compositions and methods utilizing this new GrB-NIC technology.

14 Claims, 20 Drawing Sheets

U.S. PATENT DOCUMENTS

Figure 2:
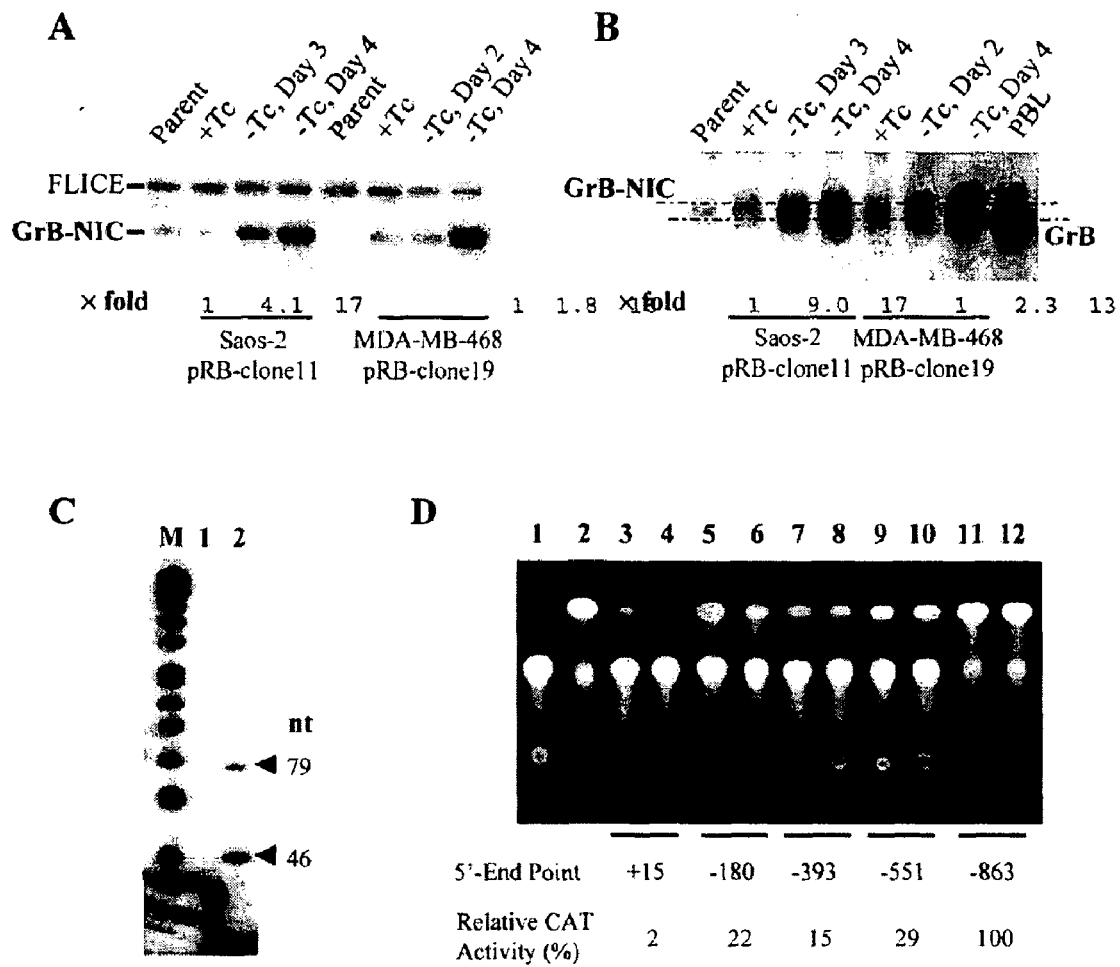

| | | | | |
|---|---|---|---|---|
| 6,537,784 | B1 * | 3/2003 | Tatake et al. | 435/91.1 |
| 6,607,879 | B1 * | 8/2003 | Cocks et al. | 435/6 |
| 6,812,339 | B1 * | 11/2004 | Venter et al. | 536/24.31 |
| 2003/0086919 | A1 * | 5/2003 | Rosenblum et al. | 424/94.63 |
| 2003/0143530 | A1 * | 7/2003 | Klepp et al. | 435/5 |

FOREIGN PATENT DOCUMENTS

| | | | |
|---|---|---|---|
| WO | WO 2002/34910 | A2 * | 5/2002 |
| WO | WO 2002/46467 | A2 * | 6/2002 |
| WO | WO 2002/68579 | A2 * | 9/2002 |
| WO | WO 2003/016475 | A2 * | 2/2003 |

OTHER PUBLICATIONS

Dahl et al., 1990, "Isolation of a cDNA encoding a novel form of granzyme B from human NK cells", Human Genetics, vol. 84, pp. 465–470.*

Haddad, P., et al., 1990, "Structural organization of the hCTLA–1 gene encoding a human granzyme B", Gene, vol. 87, No. 2, pp. 265–271.*

Hanson et al., 1990, "Transcriptional activation of the human cytotoxic serine protease gene CSP–B in T lymphocytes", Molecular and Cellular Biology, vol. 10, No. 11, pp. 5655–5662.*

Caputo et al., 1988, "Structure and differential mechanisms of regulation of expression of a serine gene in activated human T lymphocytes", The Journal of Biological Chemistry, vol. 263, No. 13, pp. 6363–6369.*

Trapani, J.A., et al., 1988, "Molecular cloning of an inducible serine esterase gene from human cytotoxic lymphocytes", Proceedings of the National Academy of Sciences, U.S.A., vol. 85, No. 18, pp. 6924–6928.*

An, B., and Dou, Q. P. (1996). Cleavage of retinoblastoma protein during apoptosis: an interleukin 1 beta–converting enzyme–like protease as candidate. Cancer Res. 56, 438–442.

Babichuk, C.K., Duggan, B.L., and Bleackley, R.C. (1996). In vivo regulation of murine granzyme B gene transcription in activated primary T cells. J. Biol. Chem. 271, 16485–16493.

Berthou, C., et al. (1995). Granzyme B and perforin lytic proteins are expressed in CD34+ peripheral blood progenitor cells mobilized by chemotherapy and granulocyte colony-stimulating factor. Blood 86, 3500–3506.

Berthou, C., et al. (1997). Acquisition of granzyme B and Fas ligand proteins by human keratinocytes contributes to epidermal cell defense. J. Immunol. 159, 5293–5300.

Bruno, A.P., et al. (2000). Acute myeloblastic leukemic cells acquire cellular cytotoxicity under genotoxic stress: implication of granzyme B and perforin. Blood 96, 1914–1920.

Chen, P.L., et al. (1992). Stability of retinoblastoma gene expression determines the tumorigenicity of reconstituted retinoblastoma cells. Cell Growth Differ. 3, 119–125.

Chen, W.D., et al. (1997). Apoptosis is associated with cleavage of a 5–kDa fragment from RB which mimics dephosphorylation and modulates E2F binding. Oncogene 14, 1243–1248.

Cordon–Cardo, C., and Richon, V.M. (1994). Expression of the retinoblastoma protein is regulated in normal human tissues. Am. J. Pathol. 144, 500–510.

Dyson, N. (1998). The regulation of E2F by pRB–family proteins. Genes Dev. 12: 2245–2262.

Fattman, C.L., et al. (1998). p53–independent dephosphorylation and cleavage of retinoblastoma protein during tamoxifen–induced apoptosis in human breast carcinoma cells. Cancer Letters 130,103–113.

Graubert, T.A., et al. (1997). Perforin/granzyme–dependent and independent mechanisms are both important for the development of graft–versus–host disease after murine bone marrow transplantation. J. Clin. Invest. 100, 904–911.

Haas–Kogan, D.A., et al. (1995). Inhibition of apoptosis by the retinoblastoma gene product. EMBO J. 14, 461–472.

Heusel, J.W., et al. (1994). Cytotoxic lymphocytes require granzyme B for the rapid induction of DNA fragmentation and apoptosis in allogeneic target cells. Cell 76, 977–987.

Hirst, C.E., et al. Perforin–independent expression of granzyme B and proteinase inhibitor 9 in human testis and placenta suggests a role for granzyme B–mediated proteolysis in reproduction. Molecular Human Reproduction, 7:1133–1142, 2001.

Hofmann, F., et al. (1996). The retinoblastoma gene product protects E2F–1 from degradation by the ubiquitin–proteasome pathway. Genes Dev. 10, 2949–2959.

Hu, SX, et al. (2003) Expression of endogenous granzyme B in a subset of human primary breast carcinomas. Br. J. Can. 89(1):135–9.

Huang, H.J., et al. (1988). Suppression of the neoplastic phenotype by replacement of the RB gene in human cancer cells. Science 242, 1563–1566.

Kennea, NL, and Mehmet, H.J (2002) Neural stem cells, Pathol., 197(4):536–50.

Klein, J.L., et al. (1989). Genomic organization and chromosomal assignment for a serine protease gene (CSPB) expressed by human cytotoxic lymphocytes. Genomics 5, 110–117.

Kontani, K., et al. (2001). Involvement of granzyme B and perforin in suppressing nodal metastasis of cancer cells in breast and lung cancers. Eur. J. Surg. Oncol. 27, 180–186.

Krek, W., et al. (1995). Cyclin A–kinase regulation of E2F–1 DNA binding function underlies suppression of an S phase checkpoint. Cell, 83: 1149–1158.

Lobe, C.G., et al. (1986). Novel serine proteases encoded by two cytotoxic T lymphocyte–specific genes. Science 232, 858–861.

Motyka, B., et al. (2000) Mannose 6–phosphate/insulin–like growth factor II receptor is a death receptor for granzyme B during cytotoxic T cell–induced apoptosis. Cell 103, 491–500.

Ogura, Y., et al. (2001). Apoptosis and allograft rejection in the absence of CD8[30] T cells. Transplantation 71, 1827–1834.

Pinkoski, M. J., et al. (2000). Nuclear translocation of granzyme B in target cell apoptosis. Cell Death Differ. 7, 17–24.

Qin, X.Q., et al. (1992). Identification of a growth suppression domain within the retinoblastoma gene product. Genes Dev. 6, 953–964.

Romano, G., et al. (2000) Latest Developments in Gene Transfer Technology: Achievements, Perspectives, and Controversies over Therapeutic Applications Stem Cells 18: 19–39.

Schmid, J., and Weissmann, C. (1987) Induction of mRNA for a serine protease and a β–thrombo–globulin–like protein in mitogen–stimulated human leukocytes. J. Immunol. 139, 250–256.

Shan, B., et al. (1996). The molecular basis of E2F–1/DP–1–induced S–phase entry and apoptosis. Cell Growth Differ. 7, 689–697.

Shi, L., et al. (1997). Granzyme B (GraB) autonomously crosses the cell membrane and perforin initiates apoptosis and GraB nuclear localization. J. Exp. Med. 185, 855–866.

Shresta, S., et al. (1997). Mechanisms responsible for granzyme B–independent cytotoxicity. Blood 89, 4085–4091.

Sun, J., et al. (2001). Importance of the P4' residue in human granzyme B inhibitors and substrates revealed by scanning mutagenesis of the proteinase inhibitor 9 reactive center loop. J. Biol. Chem. 276, 15177–15184.

Tan, X., et al. (1997). Degradation of retinoblastoma protein in tumor necrosis factor and CD95–induced cell death. J. Biol. Chem. 272, 9613–9616.

Trapani, J. A., et al. (1996). Localization of granzyme B in the nucleus. A putative role in the mechanism of cytotoxic lymphocyte–mediated apoptosis. J.Biol.Chem. 271, 4127–4133.

Wargnier, A., et al. (1995). Identification of human granzyme B promoter regulatory elements interacting with activated T–cell–specific proteins: implication of Ikaros and CBF binding sites in promoter activation. Proc. Natl. Acad. Sci. U. S. A. 92, 6930–6934.

Xu, H.–J. (1995). Altered retinoblastoma (RB) protein expression in human malignancies. Adv. Anat. Pathol. 2, 213–226.

Xu, H.–J., et al. (1997). Reexpression of retinoblastoma protein iduces tumor cell senescence and telomerase inhibition. Oncogene 15, 2589–2596.

Yang, X., et al, (1998). Granzyme B mimics apical caspases. Description of a unified pathway for transactivation of executioner caspase–3 and –7. J. Biol. Chem. 273, 34278–34283.

Yasukawa, M., et al. (2000). Granule exocytosis, and not the Fas/Fas ligand system, is the main pathway of cytotoxicity mediated by alloantigen–specific CD4(+) as well as CD8(+) cytotoxic T lymphocytes in humans. Blood 95, 2352–2355.

Zhou, Y., et al. (1994). Further characterization of retinoblastoma gene–mediated cell growth and tumor suppression in human cancer cells. Proc. Natl. Acad. Sci. U. S. A. 91, 4165–4169.

* cited by examiner

```
                                        TCACAAGAATCGAACCATGTAGAGAG    -855
AP-1 site           CCAAT box
ACTTAGTTGTCTTTTAACAGAATTGGGCACGGGCTGTTCAGAAACAACAATCTTTCACAT          -795
CCATTATAATGATAGCATTAGTGTAGTTTGTTTAGCAAATGTTTACTGTGAGCCTGTTAT          -735
GTGCTGAGCCTGCTATGTAAGAAGTGTGGCTCTCTGGACAGGAGACAGAATACTAAACAA          -675
CACAACTACTGATCTTTGGCTGCCTGGCATGCTTCCTCACTTCATATGGTATCAGCAATT          -615
TAGCACCACAAACGTCCTTTAGAGAACCAGCCCTTTCTCATTCTTGGTTCTAGTGGCTTG          -555
AGTAGACTGACCCCAGCCTACCCAAAGTGGATTTGACTCCTAGCAATTCATTAATCTAGC          -495
CCAAT box
CCAATAAAATGTCAAGTACAGGACTTTTATTGAAAGCATTCAGAAAAGAGGTGGACTCTC         -435
ACACTAAACATTTGTAACTAAATAAGGGATGTTAGAAATTCTCTAGAAAGGAAGCTATGA          -375
TAATAAATGGGTTGCTAGATGGGTCTAGTAGATGGTGGCCGTGCTTTGTTACTGCCTTGT          -315
GTATTGTGCTACCATAGCCCTCCCCAAACTGTACTCTGGCTCCTGGCATTTCCGTCTCTT         -255
CAACCAGATGGTCAGCTCTCTAAGTGAAGGAGACACATCTCCAACATGCTTGGTTCTAGC         -195
ACAACAGAAGGGCTCAAACACATACCTGCTAAAGAAACTATCCTGATGGATTTAGCAGCA         -135
         Inverted CCAAT Box/E2F-like site
TGGCCATGAGGCATTGGCGGTTCTATCACTGGGAACTCAGGTTTCTGGTGCTCCAGTACC          -75
                                                   GC-rich motif
TCTACTGGCTGATACCACATCCTACAATTCACTTCATAGGCTTGGGTTCCTGCTCTGGGC          -15
          +1    AP-1     AP-4
TGAATAGGTGGTCCACTCTGAGTCATCAGCTGTGGGTGATGATGTGGTCACTGCATGATT           46

CRE                    Ikaros
CTCACACAAGCACCCAGAGGACGTCATCAGGCAGAGGCAGTGGGGGTGGGCAGCATTTAC          106
                       Start of GrB-NIC cDNA
         CBF/AP-1            *            CRE
AGAAAATCTGTGATGAGACACCACAAAACCAGAGGGGAACATGAAGTCACTGAGCCTGCT          166
                                      M  K  S  L  S  L  L            7
            (GrB)TATA box        NF-AT site   ---▶
CCACCTCTTTCCTCTCCCAAGAGCTAAAAGAGAGCAAGGAGGAAACAACAGCAGCTCCAA          226
 H  L  F  P  L  P  R  A  K  R  E  Q  G  G  N  N  S  S  S  N          27

Start of human CTL GrB cDNA
                  *
CCAGGGCAGCCTTCCTGAGAAGATGCAACCAATCCTGCTTCTGCTGGCCTTCCTCCTGCT          286
 Q  G  S  L  P  E  K  M  Q  P  I  L  L  L  L  A  F  L  L  L          47

GCCCAGGGCAGATGCAGGGGAGATCATCGGGGACATGAGGCCAAGCCCCACTCCCGCCC           346
 P  R  A  D  A  G  E  I  I  G  G  H  E  A  K  P  H  S  R  P          67

CTACATGGCTTATCTTATGATCTGGGATCAGAAGTCTCTGAAGAGGTGCGGTGGCTTCCT         406
 Y  M  A  Y  L  M  I  W  D  Q  K  S  L  K  R  C  G  G  F  L         87

GATACAAGACGACTTCGTGCTGACAGCTGCTCACTGTTGGGGAAGCTCCATAAATGTCAC         466
 I  Q  D  D  F  V  L  T  A  A  H  C  W  G  S  S  I  N  V  T         107

CTTGGGGGCCCACAATATCAAAGAACAGGAGCCGACCCAGCAGTTTATCCCTGTGAAAAG         526
 L  G  A  H  N  I  K  E  Q  E  P  T  Q  Q  F  I  P  V  K  R         127

ACCCATCCCCCATCCAGCCTATAATCCTAAGAACTTCTCCAACGACATCATGCTACTGCA         586
 P  I  P  H  P  A  Y  N  P  K  N  F  S  N  D  I  M  L  L  Q         147

GCTGGAGAGAAAGGCCAAGCGGACCAGAGCTGTGCAGCCCCTCAGGCTACCTAGCAACAA         646
 L  E  R  K  A  K  R  T  R  A  V  Q  P  L  R  L  P  S  N  K         167

GGCCCAGGTGAAGCCAGGGCAGACATGCAGTGTGGCCGGCTGGGGGCAGACGGCCCCCCT         706
 A  Q  V  K  P  G  Q  T  C  S  V  A  G  W  G  Q  T  A  P  L         187

GGGAAAACACTCACACACACTACAAGAGGTGAAGATGACAGTGCAGGAAGATCGAAAGTG         766
 G  K  H  S  H  T  L  Q  E  V  K  M  T  V  Q  E  D  R  K  C         207

CGAATCTGACTTACGCCATTATTACGACAGTACCATTGAGTTGTGCGTGGGGGACCCAGA         826
 E  S  D  L  R  H  Y  Y  D  S  T  I  E  L  C  V  G  D  P  E         227

GATTAAAAAGACTTCCTTTAAGGGGGACTCTGGAGGCCCTCTTGTGTGTAACAAGGTGGC         886
 I  K  K  T  S  F  K  G  D  S  G  G  P  L  V  C  N  K  V  A         247

CCAGGGCATTGTCTCCTATGGACGAAACAATGGCATGCCTCCACGAGCCTGCACCAAAGT         946
 Q  G  I  V  S  Y  G  R  N  N  G  M  P  P  R  A  C  T  K  V         267

CTCAAGCTTTGTACACTGGATAAAGAAAACCATGAAACGCTACTAACTACAGGAAGCAAA        1006
 S  S  F  V  H  W  I  K  K  T  M  K  R  Y  *                        281

CTAAGCCCCCGCTGTAATGAAACACCTTCTCTGGAGCCAAGTCCAGATTTACACTGGGAG        1066
AGGTGCCAGCAACTGAATAAATACCT                                          1092
```

Figure 1

Genomic Map of the Murine GrB-NIC (GrB) Gene
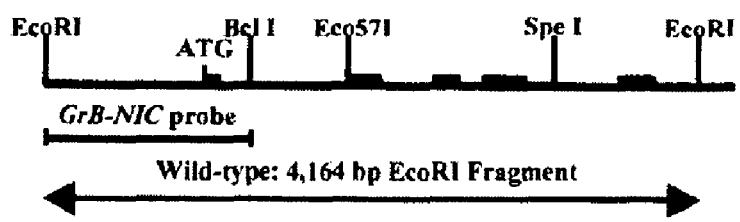
Structure of the Targeting Vector
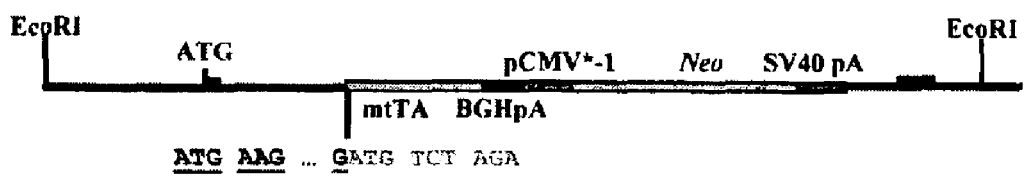
Schematics of the Disrupted GrB-NIC (GrB) Allele
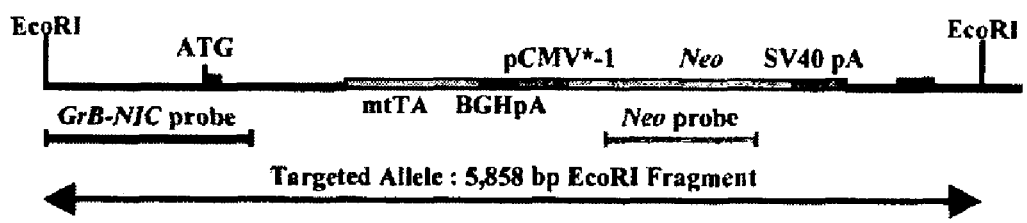
Figure 14

A
Saos-2.pRB clone with chromosomally
integrated pGrB-NIC-Luc
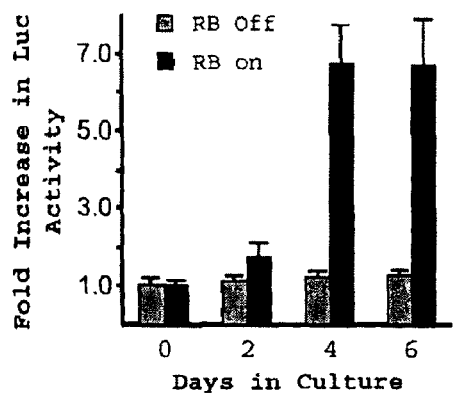
B
MC3T3 Stably Transfected
with pGrB-NIC-Luc
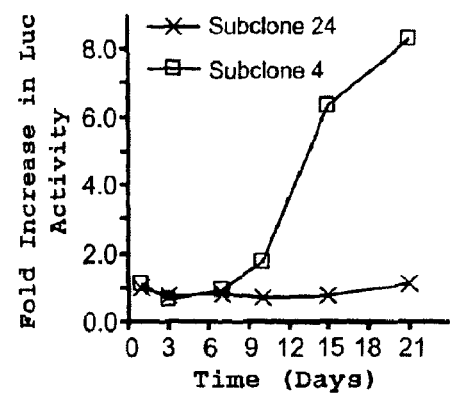
Figure 20

ENDOGENOUS GRANZYME B IN NON-IMMUNE CELLS

STATEMENT REGARDING FEDERALLY SPONSORED RESEARCH OR DEVELOPMENT

The development of this invention was supported in part by grants from the National Institutes of Health (R01CA67274) and the Texas Higher Education Coordinating Board (ATP003657-0159). Accordingly, the U.S. government may have certain rights in the invention.

CROSS-REFERENCES TO RELATED APPLICATIONS

Not applicable.

REFERENCE TO A "MICROFICHE APPENDIX"

Not applicable.

BACKGROUND OF THE INVENTION

1. Field of the Invention

The instant invention relates to the fields of molecular biology, diagnostics and therapeutics. More particularly, the invention relates an isolated nucleic acid sequence encoding a novel endogenous precursor for granzyme B in non-immune cells (GrB-NIC). The invention also relates to methods of detection, expression, or inhibition of GrB-NIC in non-immune cells to modulate apoptosis and maintain tissue homeostasis for prevention and therapy of human diseases.

2. Description of Related Art

Human granzyme B (GrB) is a member of a subfamily of serine proteases originally found in granules of cytotoxic T lymphocytes (CTL) and natural killer (NK) cells. Since its cloning in the late 1980s (Lobe et al., 1986; Schmid and Weissmann, 1987; Trapani et al., 1988), GrB has been mainly, if not exclusively, implicated in immune cell-mediated target cell killing (Yang et al., 1998; Yasukawa et al., 2000). The critical role of GrB in DNA fragmentation and apoptosis of target cells was established by compelling studies using CTL from GrB-deficient mice (Heusel et al., 1994). In a wide range of cellular immune reactions against bacterium/virus-infected, alloreactive, or neoplastic cells, GrB is produced by activated cytotoxic lymphocytes and stored in cytoplasmic granules; after effector-target cell conjugation, these granules are exocytosed, releasing GrB and other cytolytic proteins including a pore-forming protein (perforin). Then, perforin-dependent and perforin-independent mechanisms, the latter involving, at least in part, an insulin-like growth factor-II receptor (IGF-IIR) on the target cell surface (Shi et al., 1997; Motyka et al., 2000), facilitate the entry and intracellular trafficking of GrB in target cells. Once in the target cell cytosol, GrB leads to rapid induction of DNA fragmentation and apoptosis by activating downstream caspases (Yang et al., 1998) or through a Bcl-2-inhibitable mitochondrial pathway (Pinkoski et al., 2001).

Although generally associated with cytotoxic lymphocytes, more recently, albeit controversially (Graubert et al., 1997), expression of GrB-like protease was reported in other normal and malignant hematopoietic (non-lymphoid) cells, such as pluripotent stem cells capable of giving rise to all hematopoietic lineages, mobilized $CD34^+$ hematopoietic progenitor cells, acute myeloblastic leukemic cells under genotoxic stress (Berthou et al., 1995; Bruno et al., 2000), epidermal keratinocytes (Berthou et al., 1997), testis and placenta (Hirst et al., 2001). In these later studies, however, expression of so called "GrB" mRNA was demonstrated only by in situ hybridization using antisense GrB RNA probes. The method was not able to determine the extent of the nucleotide sequence identity between more or less closely related RNA species, nor the size of the transcripts. Independent studies reported by others failed to detect GrB mRNA expression in mobilized hematopoietic CD34+ progenitor cells when an S1 nuclease protection assay was employed.

BRIEF SUMMARY OF THE INVENTION

The instant invention relates to the discovery and isolation of a nucleic acid sequence that encodes a novel protease precursor (pre-enzyme, preproenzyme, or zymogen) for endogenous granzyme B in non-immune cells (designated GrB-NIC). (Hu, et al. 2003, herein expressly incorporated by reference). This new protease precursor was ascertained based upon the observation that the constitutively nearly silent GrB locus in human breast carcinoma and osteosarcoma cells is activated upon retinoblastoma protein (pRB)-induced growth arrest and differentiation owing to the usage of an alternative promoter/transcription start site. Novel cloned cDNA from the locus was predicted to add 34 amino acid residues to the N-terminus of known GrB zymogen from cytotoxic lymphocytes. Subsequent experiments have demonstrated the presence of GrB-NIC in a variety of cancer cells and normal non-immune cells, including endothelial and mesenchymal cells, and particularly in differentiating neuronal cells.

The novel GrB-NIC of this invention is expressed in non-immune cells as a pre-enzyme with an unusually long signal peptide (52 amino acids in length, the longest signal peptide among mammalian serine proteases reported to date) prior to post-translational processing. However, post-translational modification of the pre-enzyme entails that the mature, active form of GrB-NIC is essentially identical to lymphocyte GrB but with a distinctive glycosylation pattern. The many biochemical and biological similarities between GrB-NIC and GrB support the view that in non-immune cells, up-regulation of GrB-NIC has the same biological consequences as acquiring exogenous GrB from cytotoxic lymphocytes. The discovery of a novel pre-enzyme for endogenous granzyme B in non-immune cells, and the functional similarities of its mature form with lymphocyte granzyme B challenge the current paradigm for cytotoxic lymphocyte-mediated immunity, providing a more rational basis and intellectual framework for designing innovative methods and compounds for diagnosis, prognosis and treatment of a variety of human diseases.

The present invention relates to methods of detection, expression, or inhibition of GrB-NIC in non-immune cells of a mammal, such as a human. In one embodiment, expression of GrB-NIC in human breast carcinoma and osteosarcoma cells upon pRB-mediated senescent arrest and differentiation was determined at the mRNA level by RPA assay, Northern blotting and nucleotide sequencing analysis; at the protein level by Western blotting and immunochemical staining; and at the biochemical/biological function levels by enzymatic and apoptosis assays. Tumor cells with accumulated GrB-NIC undergo apoptosis that occurs concurrently with pRB cleavage, and are capable of inducing rapid apoptosis of bystander cells.

In another embodiment, the endogenous GrB-NIC-induced cell death is accelerated by infection with replication-deficient adenovirus (vector only), which can function as a substitute for perforin, enabling GrB-NIC to enter into the cytosol In another embodiment, by immunohistochemical staining of paraffin-embedded tumor sections, GrB-NIC is detected in vivo in malignant cells of a subset of breast cancers and their adjacent reactive endothelial and mesenchymal cells in which endogenous retinoblastoma protein (pRB) is overexpressed. The percentage of breast and lung cancer cells with positive GrB-NIC immunoreactivity is correlated with low incidence of regional lymph node metastasis, and consequently correlated with good prognosis of cancer patients.

In another embodiment, the alternative GrB-NIC promoter in non-immune cells is activated by overexpression of pRB or p53 tumor suppressor genes, by overexpression of E2F-1 transcription factor, and by induction of cell differentiation.

In another embodiment, as determined by immunochemical staining, Northern blotting, Western blotting, and reverse transcriptase (RT)-PCR analysis, expression of the GrB-NIC gene is activated during retinoic acid (RA)-induced neuronal differentiation of mouse P19 pluripotent embryonic stem cells. GrB-NIC transcripts were also present in normal mouse embryonic brains in vivo at embryonic day 12.5, 13.5 and 14.5, with a related peak at E13.5. Successful embryonic neuronal development and tissue homeostasis reflects a balance between the functional consequences of pRB and GrB-NIC expression, which is essential for selective, post-mitotic neuronal cells to exit the cell cycle, to complete migration or differentiation, and to survive.

In another embodiment, expression of GrB-NIC was also detected in human normal differentiating embryonic neuronal cells coinciding with elevated expression of pRB in the same cells. RT-PCR analysis indicated that GrB-NIC mRNA from human neuronal cells indeed contained the upstream AUG codon, identical to the endogenous granzyme B (GrB-NIC) mRNA in Saos-2 osteosarcoma cells upon pRB-mediated terminal differentiation.

In another embodiment, GrB-NIC, when produced in excess in vivo, cause apoptosis of normal cells and allograft cells, and is related to autoimmune diseases and allograft rejection. Thus, methods and compounds for inhibition of endogenous GrB-NIC expression can be used rationally as a novel treatment for a subset of autoimmune diseases, such as rheumatoid arthritis and type-I diabetes, and allograft rejection after bone marrow, skin, renal, and other organ transplantation.

In another embodiment, given the objective of human therapeutic cloning is to produce pluripotent stem cells that carry the nuclear genome of the patient and then induce them to differentiate into replacement cells, regulation of apoptosis and tissue homeostasis through targeting the endogenous GrB-NIC of this invention becomes an essential step towards production of genetically matched cells and tissues from these pluripotent stem cells for transplantation. The genetically matched cells and tissues include, for example, cardiomyocytes for replacing damaged heart tissue, insulin-producing cells for patients with diabetes, or neurons for patients with neurological disorders.

A further embodiment of the instant invention encompasses isolated nucleic acid. The isolated nucleic acid sequence may consisting essentially of the nucleic acid sequence of SEQ ID NO: 1, the nucleic acid sequence of SEQ ID NO: 2, or be an isolated nucleic acid encoding the amino acid sequence of SEQ ID NO: 3. A further embodiment encompasses a polypeptide, consisting essentially of the amino acid sequence of SEQ ID NO: 3.

Another embodiment of the instant invention comprises a method for producing a GrB-NIC polypeptide, comprising: transforming or transfecting a host cell with a nuclei acid comprising the nucleic acid sequence of SEQ ID NO: 1, to obtain a transformed or transfected host cell; culturing the transformed or transfected host cell to obtain a cell culture; expressing the nucleic acid in the transformed or transfected host cell to produce the polypeptide; and isolating the polypeptide from the cell culture. It is contemplated that this method may be carried out in a prokaryotic cell or alternatively in a eukaryotic cell. The method may be further carried out with a nucleic acid further comprising regulatory elements necessary to express GrB-NIC polypeptide in a eukaryotic host cell. The regulatory elements may be native GrB-NIC regulatory elements.

Further embodiments of the invention include a vector comprising a cloned nucleic acid, the cloned nucleic acid consisting essentially of the nucleic acid sequence of SEQ ID NO: 1 or alternatively SEQ ID NO: 2.

The invention is further contemplated to include a pharmaceutical composition, comprising a nucleic acid expression vector or expression cassette comprising a cloned nucleic acid, said cloned nucleic acid consisting essentially of the nucleic acid sequence of SEQ ID NO: 1 or SEQ ID NO:2, in combination with a pharmaceutically acceptable carrier.

It is further contemplated that the invention encompasses a method for identifying modulators of a GrB-NIC activity, comprising: incubating GrB-NIC and a candidate modulator; introducing a GrB-NIC substrate; and comparing the activity of GrB-NIC in the presence and absence of the modulator. This method may be practiced where GrB-NIC activity is Asp-ase activity.

A further method within the scope of this invention comprises inhibiting the expression of GrB-NIC comprising contacting tissues or cells which express GrB-NIC with an antisense compound, wherein said antisense compound inhibits GrB-NIC gene expression. In this method the tissues or cells may include non-hematopoietic or non-immune cells or tissues.

Another embodiment of the instant invention encompasses a method for screening for neurological disorders, comprising assessing GrB-NIC expression. Such screening may be of neural cells. The GrB-NIC may be assessed by detecting mRNA encoding GrB-NIC or by detecting GrB-NIC protein or polypeptide. It is contemplated that the neurological disorder may be a degenerative neurological disorder, an apoptosis based degenerative neurological disorder or that it may be selected from a group consisting of Alzheimer's Disease, Parkinson's disease, Huntington's chorea, multiple sclerosis, Progressive Supranuclear Palsy, Stiff-Person Syndrome and Transverse Myelitis.

A further embodiment of the instant invention encompasses a method for screening for autoimmune diseases, comprising assessing GrB-NIC expression in non-immune cells.

It is further contemplated that the disclosed invention encompasses a method for screening for transplant rejection and graft-versus-host diseases, comprising assessing GrB-NIC expression in non-immune cells of grafted tissues and organs.

A still further embodiment of the invention comprises a method of inducing apoptosis in a cell comprising introducing a nucleic acid comprising a sequence encoding GrB-NIC into the cell under conditions permitting the expression of GrB-NIC so as to thereby induce apoptosis in the cell. This method may be further characterized as a sequence encoding GrB-NIC with an internal deletion of the activation dipeptide Gly53–Glu54. In alternate embodiments of this method, the nucleic acid may comprise a vector or naked DNA. In this method the nucleic acid may be introduced into the cell by a number of techniques, including via a liposome, via an antibody-coated liposome, via a mechanical means or via an electrical means. It is contemplated that a number of cell types may be utilized in various embodiments of this method, including, cancer cells, non-immune cell and cells infected with a virus.

A still further embodiment of the claimed invention comprises a method of detecting cells in an apoptotic or pre-apoptotic state comprising assessing GrB-NIC expression. In a particular aspect of this method the cell may be a non-immune cell. It is contemplated that a variety of means of assessing GrB-NIC expression may be used, including detecting RNA encoding GrB-NIC or detecting GrB-NIC protein or peptide.

A further embodiment encompasses a method of modulating endogenous GrB-NIC expression, comprising regulating the expression of a tumor suppressor gene. Further embodiments of this method include regulating tumor suppressor such as pRB or p53.

An additional embodiment of the invention relates to a method of modulating intracellular trafficking of endogenous GrB-NIC, comprising administering a composition comprising adenovirus.

The instant disclosure further relates a gene therapy agent comprising: an expression construct and a nucleic acid consisting essentially of the nucleic acid sequence of SEQ ID NO:2. A variety of expression constructs may be employed in this method, including, for example, a viral vector.

A still further embodiment of the instant invention encompasses a method of treating a cancer comprising, administering an expression construct to a patient, wherein said expression construct comprises a nucleic acid consisting essentially of the nucleic acid sequence of SEQ ID NO:2. A variety of cancers may be treated in alternate embodiments of this method, including cancers selected from a group consisting of breast cancer, osteosarcoma, prostate cancer, bladder cancer, ovarian cancer and lung cancer.

An alternate embodiments of the instant invention are methods of inhibiting GrB-NIC comprising contacting tissues or cells which express GrB-NIC with an composition comprising SPI-6 or PI-9, wherein said SPI-6 or PI-9 inhibits GrB-NIC enzymatic activity. The tissues or cells utilized in these methods may come from a variety of sources, such as, for example, non-hematopoietic origins, human neural cell lineages and embryonic stem cells.

Still further embodiments encompasses methods of blocking surface expression of GrB-NIC comprising contacting tissues or cells which express GrB-NIC with an composition comprising SPI-6 or PI-9, wherein said SPI-6 or PI-9 inhibits GrB-NIC surface expression.

A particular embodiment of the instant invention encompasses a method for identifying modulators for GrB-NIC expression, comprising: incubating a cell comprising the nucleic acid sequence of SEQ ID NO: 1; contacting said cell with a candidate modulator; and assaying GrB-NIC expression in said cell. This method may incorporate an expression construct comprising the nucleic acid sequence of SEQ ID NO: 1 and may include the use of a non-immune cell.

It is further contemplated that the invention discloses a method for identifying modulators of a GrB-NIC expression, comprising: incubating a cell comprising the nucleic acid sequence of SEQ ID NO: 1; contacting said cell with a candidate modulator; and assaying GrB-NIC transcription in said cell. This method may generally incorporate expression constructs comprising the nucleic acid sequence of SEQ ID NO: 1 and may further be carried out in a non-immune cell.

A further method contemplated as within the scope of the invention is a method of inhibiting GrB-NIC comprising contacting tissues or cells which express GrB-NIC with a modulator, wherein said modulator inhibits GrB-NIC gene expression. The tissues or cells utilized in embodiments of this method may come from a variety of sources, such as, for example, non-hematopoietic origins, human neural cell lineages and embryonic stem cells.

A still further embodiment comprises method of inhibiting apoptosis in cultured stem cells by introducing a modulator to inhibit GrB-NIC expression. In the context of this method, a number of modulator can be employed, including, for example SpI-6 or PI-9.

Another embodiment of the invention relates to cells resulting from the differentiation of stem cells or progenitor cells cultured in the presence of a modulator of GrB-NIC and a differentiation factor.

FIGURES

The following drawings form part of the present specification and are included to further demonstrate certain aspects of the present invention. The invention may be better understood by reference to one or more of these drawings in combination with the detailed description of specific embodiments presented herein.

FIG. 1. Complete Nucleotide Sequence of the Cloned GrB-NIC cDNA and 5'-flanking Genomic Region. The nucleotide sequence and predicted amino-acid sequence are aligned by sequence overlap with human CTL GrB and its 5'-flanking region. The first AUG codons for GrB-NIC and for lymphocyte GrB are boxed. The putative activation dipeptide is in bold type, and the upright arrow indicates the predicted DPPI cleavage site. The polyadenylation site is underlined. Bend arrows indicate the transcriptional start sites of GrB-NIC as mapped by primer extension assay (see FIG. 2C). The major start site is assigned position +1. The immediate upstream GC-rich motif, putative CCAAT boxes, E2F-like site, and AP-1 and AP-4 sites of the deduced GrB-NIC core promoter (underlined) are shown in bold type. A further upstream sequence resembling the TATA box is doubly underlined. The nucleotides in italic bold type are revised from the public databases, where apparent discrepancies exist (GenBank M38273, M38193, and M28879). Dashed arrow, lymphocyte GrB transcriptional start site (Klein et al., 1989). In comparison, the GrB proximal promoter is underlined with broken lines, and consensus sequences within the region are in italic type. The GrB-NIC cDNA sequence GenBank database accession number is AY372494 (bankit504735).

FIG. 2. Analysis of GrB-NIC Transcripts and Corresponding Promoter. (A) RPA and (B) Northern blotting analyses of GrB-NIC transcripts in RB-reconstituted Saos-2 and MDA-MB-468 clones. Cellular RNAs extracted from parental Saos-2 and Tc-regulated pRB clone cells were analyzed at each indicated day. (+Tc) medium containing 0.5 μg/ml of Tc; (−Tc) Tc-free medium. An RNA sample from PBL of healthy donors cultured in the presence of 50 units/ml of IL-2 was included in the Northern blot as GrB-positive control. Note that GrB-NIC mRNAs are larger than the GrB mRNA on the Northern blot. The numbers under the blots indicate the fold increases in GrB-NIC transcription. (C) Mapping the transcriptional initiation sites by primer extension assay. Lane 1, total RNAs from a human B-lymphoblast cell line, Daudi; Lane 2, total RNAs from Saos-2 pRB-clone 11 grown in Tc-free medium. The lengths (in nucleotides) of the primer extension products are indicated. M, ($\gamma$-32P)-labeled ($\phi$X174 Hinf I DNA markers. (D) Deletion analysis of the GrB-NIC promoter. A DNA fragment spanning the GrB-NIC 5'-flanking region from −863 to +70 was inserted into a promoterless CAT vector, pCAT3 (Promega). From this master reporter plasmid construct, a series of 5' deletion mutants of the putative promoter region were generated. The reporter plasmid constructs with 5'-end points of the promoter fragments at +15, −180, −393, −551, and −863, as indicated (lanes 3–12), were transfected into Saos-2 cells, and cell extracts were assayed for CAT activity. Saos-2 cells were also transfected with the promoterless pCAT3 vector (lane 1) and a CAT-expressing plasmid driven by an RB promoter fragment (−201/+257 relative to the RB transcription start site) (lane 2) for comparison. Cell extracts containing 100 µg (lane 2) or 200 µg (all other lanes) of the total protein were used for the CAT assay. CAT activities were visualized by TLC. Each transfection was carried out in duplicate. The experiment was repeated three times and only one representative plate is shown. CAT activities were measured by conversion rates of substrate to acetylated products and are expressed in percentages relative to the conversion rate of cells transfected with the master reporter plasmid construct.

Figure 3:
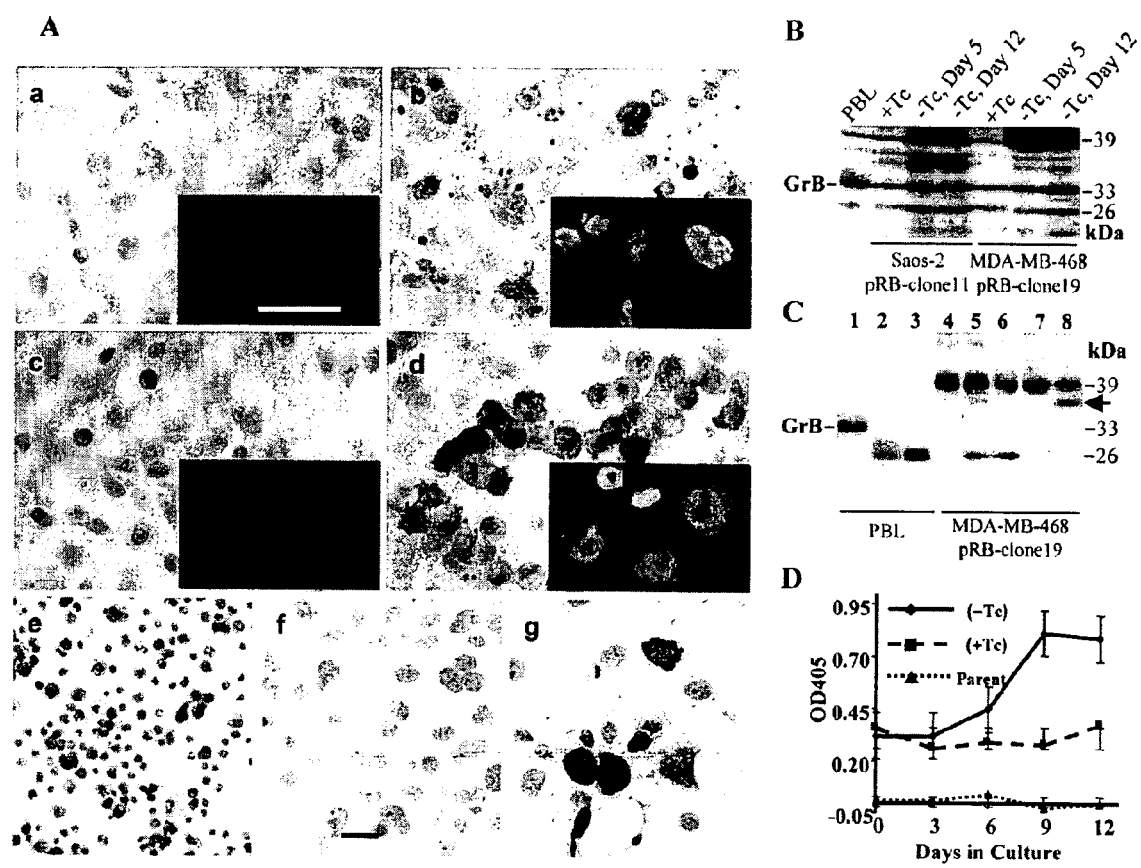

FIG. 3. Analysis of GrB-NIC expression in RB-reconstituted Saos-2 and MDA-MB-468 tumor cells at the protein level.(A) Immunochemical staining of GrB-NIC. Panel a & b, Tc-regulatable Saos-2 pRB-clone 11; Panel c & d, MDA-MB-468 pRB-clone 19-4. Expression of GrB-NIC (brown staining) was induced in Tc-free medium (b, d). The CLSM images shown in the inserts illustrate the double immunofluorescence staining of pRB (FITC, green) and GrB-NIC (Texas Red). Scale bars, 25 µm. Panel e, IL-2-activated human PBL as GrB-positive control; Panel f, Cos-7 cells, GrB-NIC negative; and Panel g, Cos-7 cells, 36 h after transfection with pCMV. GrB-NIC plasmid. (B) Western blotting. GrB-NIC protein triplets with molecular weights of 26, 33, 39 kDa were accumulated in RB-reconstituted cells grown in Tc-free medium. (C) The deglycosylated GrB-NIC and GrB proteins are identical in apparent molecular masses. Cell lysates were prepared from IL-2-activated PBL or MDA-MB-468 pRB-clone 19 cells (in Tc-free medium, Day 5). Each lane contains 5 µg of total cellular proteins treated: (Lanes 1 & 4) reaction buffer without Endo H, and (Lanes 2, 3, 5 & 6) with Endo H. Cell extracts in lanes 3 & 6 were pre-denatured. Following deglycosylation, both the 33-kDa mature lymphocyte GrB protein (lanes 1) and the 39-kDa GrB-NIC protein (lanes 4) migrated to the identical position with an apparent Mr of 26 kDa (lanes 2, 3, 5 & 6). Also note that when small amounts of total cellular proteins (5 µg) were loaded in each lane, only the major species, that is, the 33-kDa glycosylated GrB in lane 1 and the 39-kDa glycosylated GrB-NIC in lane 4 were visible prior to Endo H treatment. (Lane 7 & 8) The RB-reconstituted MDA-MB-468 cells were cultured in the absence (Lane 7) or presence (Lane 8) of tunicamycin. Arrow indicates a partially deglycosylated GrB-NIC of ~36 kDa. (D) ASPase assay of immunoprecipitated GrB-NIC proteins. ASPase activity is presented as absorbance at 405 nm. □, Saos-2 pRB-clone 11 in Tc-free medium; □, medium containing 0.5 µg/ml of Tc; □, parental Saos-2. All results are the means of triplicate wells in a single representative experiment of three performed.

Figure 4:
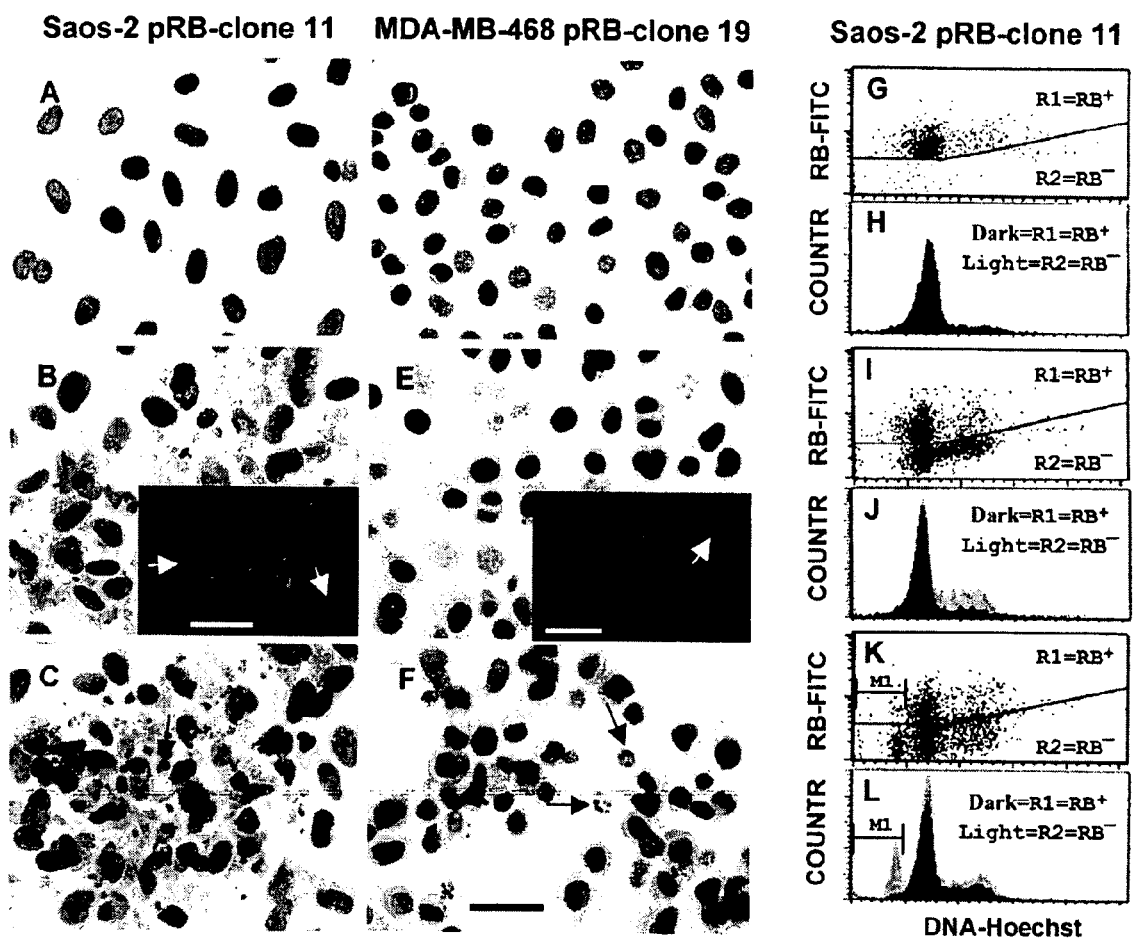

FIG. 4. RB-reconstituted Osteosarcoma and Breast Carcinoma Cells Induce Apoptosis of Parental pRB⁻ Cells in Mixed Cultures. (A to F) Immunocytochemical staining of pRB. Panel A, Saos-2 pRB-clone 11 in Tc-free medium for 2 days shows uniformly pRB⁺ staining; Panels B & C, Saos-2 pRB-clone 11 mixed with parental pRB⁻ Saos-2 cells (2:1) in Tc-free medium, at day 2 (B) and day 5 (C). Panel D, MDA-MB-468 pRB-clone 19-4 in Tc-free medium for 2 days, pRB⁺; Panels E & F, MDA-MB-468 pRB-clone 19-4 mixed with parental pRB⁻ MDA-MB-468 cells (2:1) in Tc-free medium, at day 2 (E) and day 5 (F). Scale bars, 50 µm. CLSM images in the inserts of Panels B & E exemplify the double immunofluorescence staining of pRB (FITC, green) and GrB-NIC (Texas Red). Note that both pRB⁺ and pRB⁻ (open arrows) tumor cells in the mixed cultures show positive GrB-NIC staining. In Panels C & F, the majority of the pRB⁻ cells had died with the presence of numerous condensed subnuclear bodies (solid arrows). Scale bars, 12.5 µm. (G to L) Dual-parameter FACS analysis illustrates apoptosis of mainly pRB⁻ parental tumor cells in mixed cultures. Panel G & H, Saos-2 pRB-clone 11 in Tc-free medium, day 2; Panel I-L, Saos-2 pRB-clone 11 mixed with parental Saos-2 (1:1) in Tc-free medium at day 2 (I, J) and day 3 (K, L). Panel G, I & K, dot plots depicting profiles of FITC (pRB) versus Hoechst 33342 (DNA) fluorescence. The pRB⁺ cells in gate RI are arrested in $G_1$ phase and are easily distinguished from the pRB⁻ cells in gate R2. Panels H, J, & L are corresponding histograms depicting profiles of cells in gate R1 (dark) and gate R2 (light). Panels K & L, M1 (sub-$G_1$)=2.4% in gate R1 (pRB⁺) versus 17.5% in gate R2 (pRB⁻).

Figure 5:
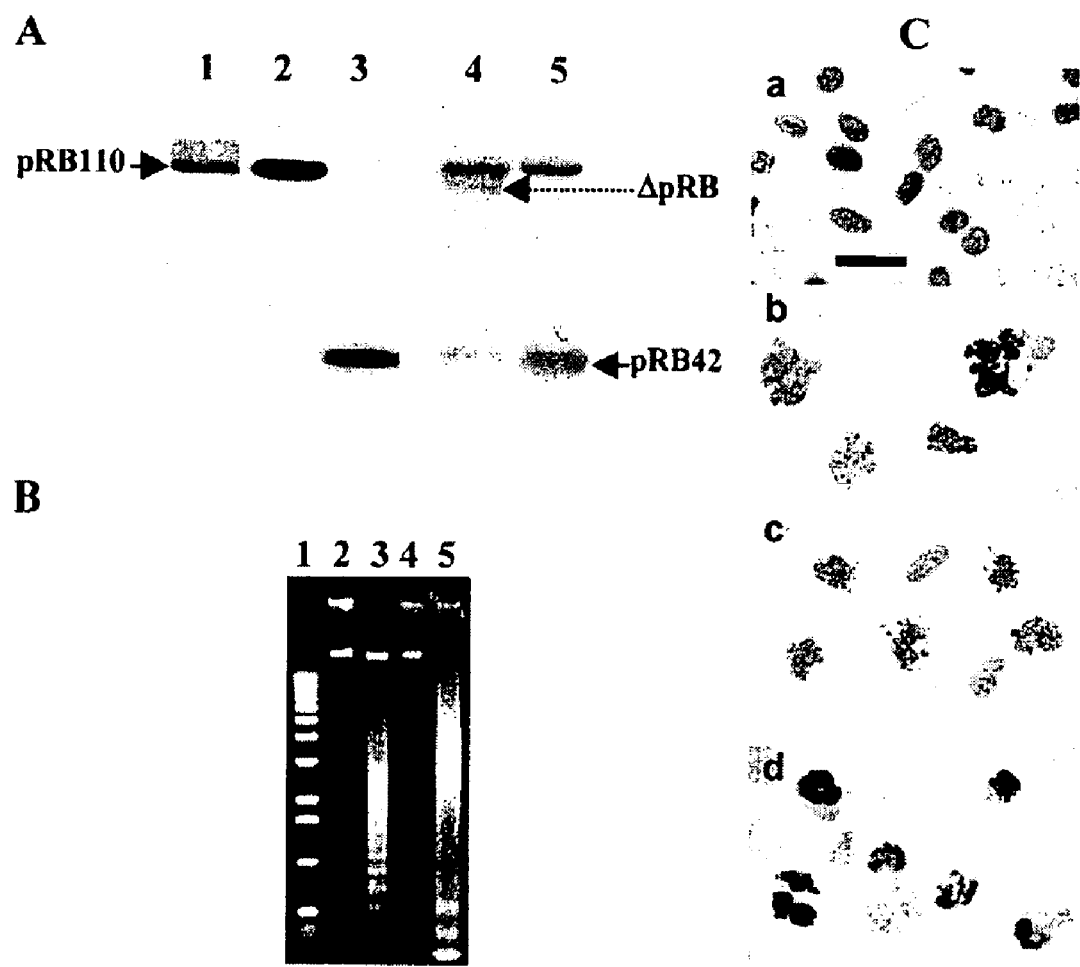

FIG. 5. Proteolytic Cleavage of pRB and Post-growth-arrest Apoptosis of RB-reconstituted Saos-2 Tumor Cells. (A) Western blotting analysis of interior (pRB42) and C-terminal (ΔpRB) cleavage fragments of pRB. Cell lysates were prepared from WI-38 fibroblasts (wild-type pRB110 control, lane 1) and the Tc-regulated Saos-2 pRB-clone-11 (lanes 2–5). The clone cells were cultured in Tc-free medium for 4 days (lane 2), and were subsequently grown in medium containing 0.5 µg/ml of Tc for 48 h (lane 3), or in medium containing 0.05 µg/ml of Tc for 4 days (lane 4) or 8 days (lane 5). (B) DNA fragmentation assay. Lane 1, molecular weight markers; Lanes 2–5, DNAs isolated from corresponding Saos-2 pRB-clone 11 cell cultures of Panel A, lanes 2–5. Characteristic DNA ladders are evident in lanes 3 & 5. (C) Post-growth-arrest apoptosis of RB-reconstituted tumor cells is illustrated by ³H-thymidine labeling and pRB immunocytochemical staining (b, c), or by TUNEL (d). Panel a, Saos-2 pRB-clone 11 cells continuously grown in medium containing 0.5 µg/ml of Tc for 2 weeks (pRB⁻) had apparently viable nuclei and heterogenous ³H-thymidine incorporation consistent with asynchronous cell culture; Panel b, Saos-2 pRB-clone 11 cells cultured under the same condition as indicated in Panels A & B, lane 3, but in medium containing Tc for 4 days, showing pRB-negative but ³H-positive lobulated nuclei; Panel c, Saos-2 pRB-clone 11 cells cultured under exactly the same condition as indicated in Panels A & B, lane 5 show weaker pRB⁺ (as compared with FIG. 4, panel A) and ³H-positive lobulated nuclei. Either withdrawal (b) or reduction (c) of pRB expression from these post-growth-arrested cells led to cell-cycle reentry (³H-thymidine incorporation) and strikingly deformed nuclei. Panel d, duplicated culture of Panel c, confirming that the deformed nuclei were TUNEL positive. Scale bar, 50 µm.

Figure 6:
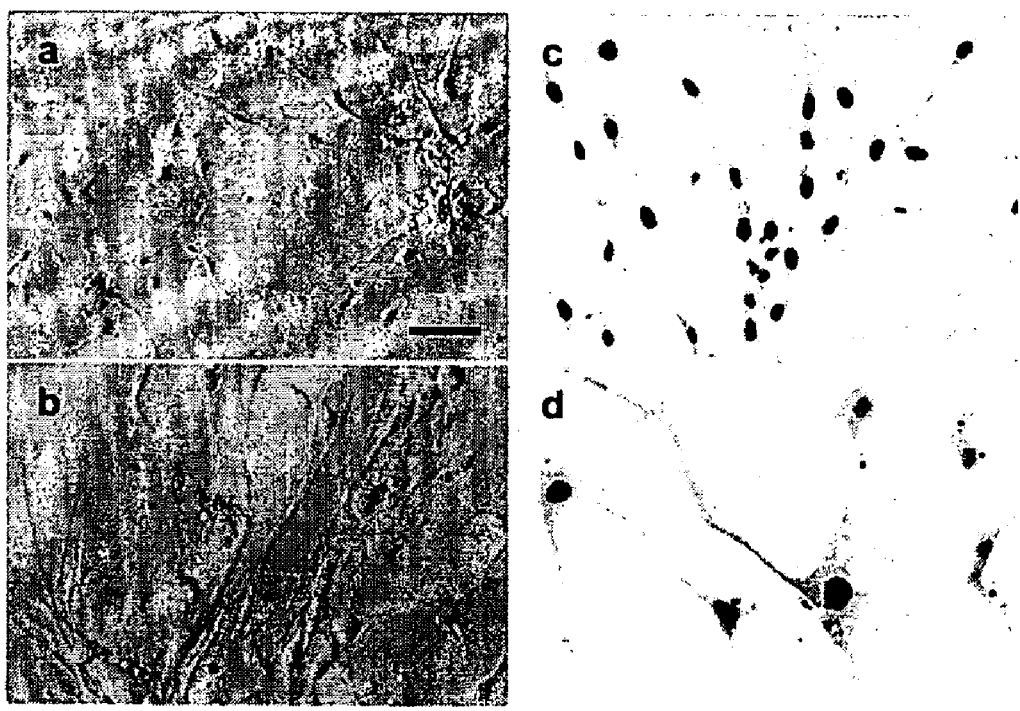

FIG. 6. GrB-NIC Expression in Human Differentiated Neuronal Cells. Human primary embryonic neural progenitor spheroids (a) and differentiating neuronal cells (b), the latter exhibiting positive pRB (c) and GrB-NIC (d) immunoreactivity. The high intensity of pRB staining in embryonic neuronal cells (c) was comparable to that of RB-reconstituted tumor cells (see FIG. 4 above). Scale bar, 100 µm (a, c), 50 µm (b) and 37.5 µm (d).

Figure 7:
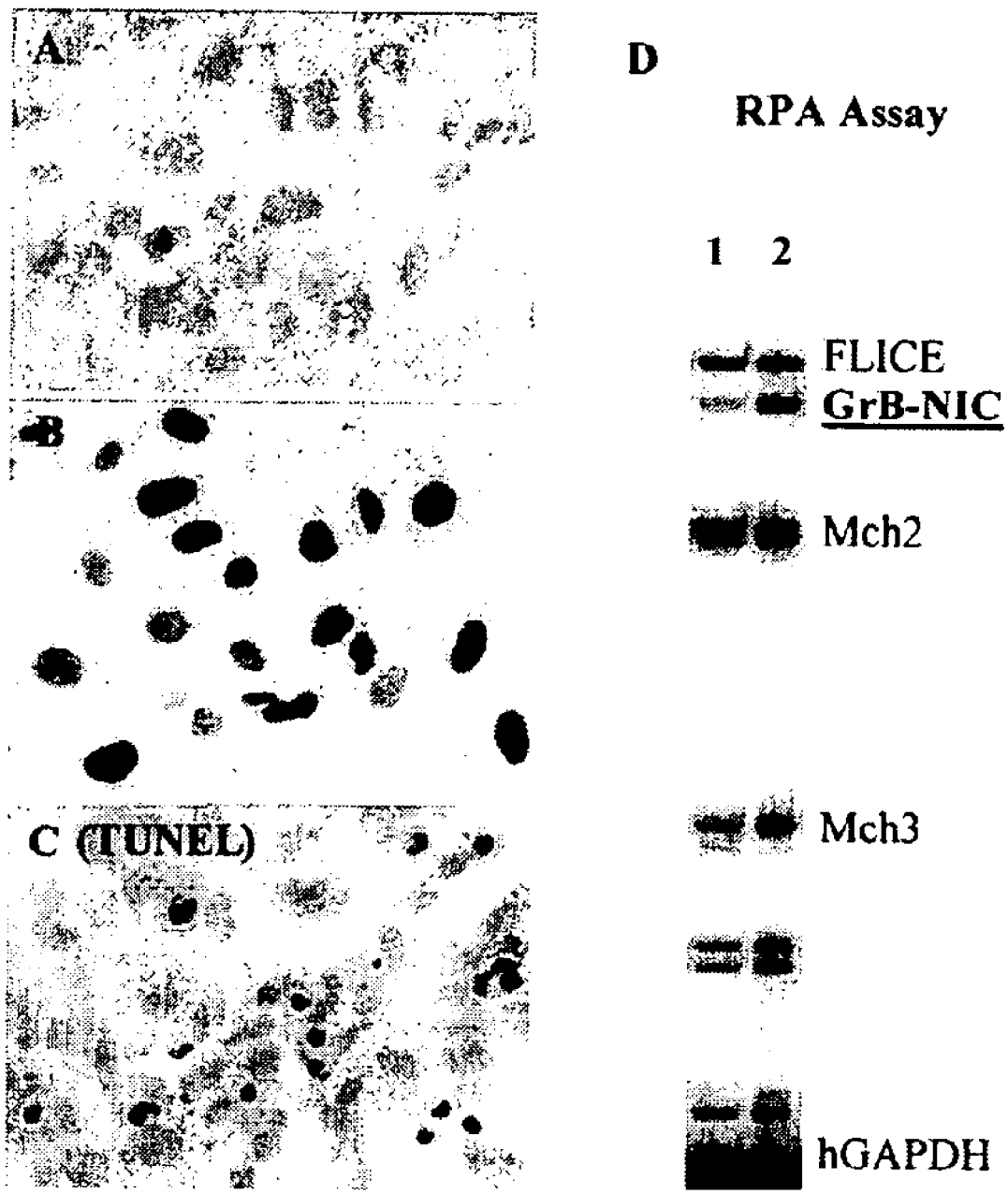

FIG. 7. Wt-p53 induces rapid apoptosis in RB-deficient Saos-2 clone cells which is associated with up-regulation of endogenous GrB (GrB-NIC) transcription. A representative Tc-regulated Saos-2 p53 clone in Tc-containing medium (Panel A, and D, lane 1). Or in Tc-free medium for 12 h (Panel B) and 24 h (Panel C, and D, lane 2). By using the improved Tc-regulatable gene expression system as described in FIG. XX, stable Saos-2 tumor cell clones, in which expression of wt p53 can be turned on and off were established. The osteosarcoma cell line, Saos-2, was chosen as a model system, since it contains a complete deletion of p53 gene ($p53^{null}$) and a defective (non-functional) RB gene ($pRB^-$). The tight control of wt p53 expression in one of the representative Saos-2 p53 clones is demonstrated by p53 immunostaining. Expression of wt p53 in the tumor cells was almost completely abrogated ($p53^-$) when there was as little as 0.1–0.5 µg/ml of Tc in the medium (compare panels A and B). In this model, it was found that wt-p53 can induce endogenous GrB-NIC in the absence of pRB, resulting in rapid apoptosis of pRB mutant cells. Reexpression of wt p53 in $p53^{null}/pRB^-$ Saos-2 cells (that is, in Tc-free medium for less than 24 h) triggered rapid apoptosis, which is shown by numerous TUNEL-positive cells in panel C. The apoptotic cell death was associated with transcriptional activation of the endogenous GrB gene (in the absence of functional pRB) (panelD).

Figure 8:
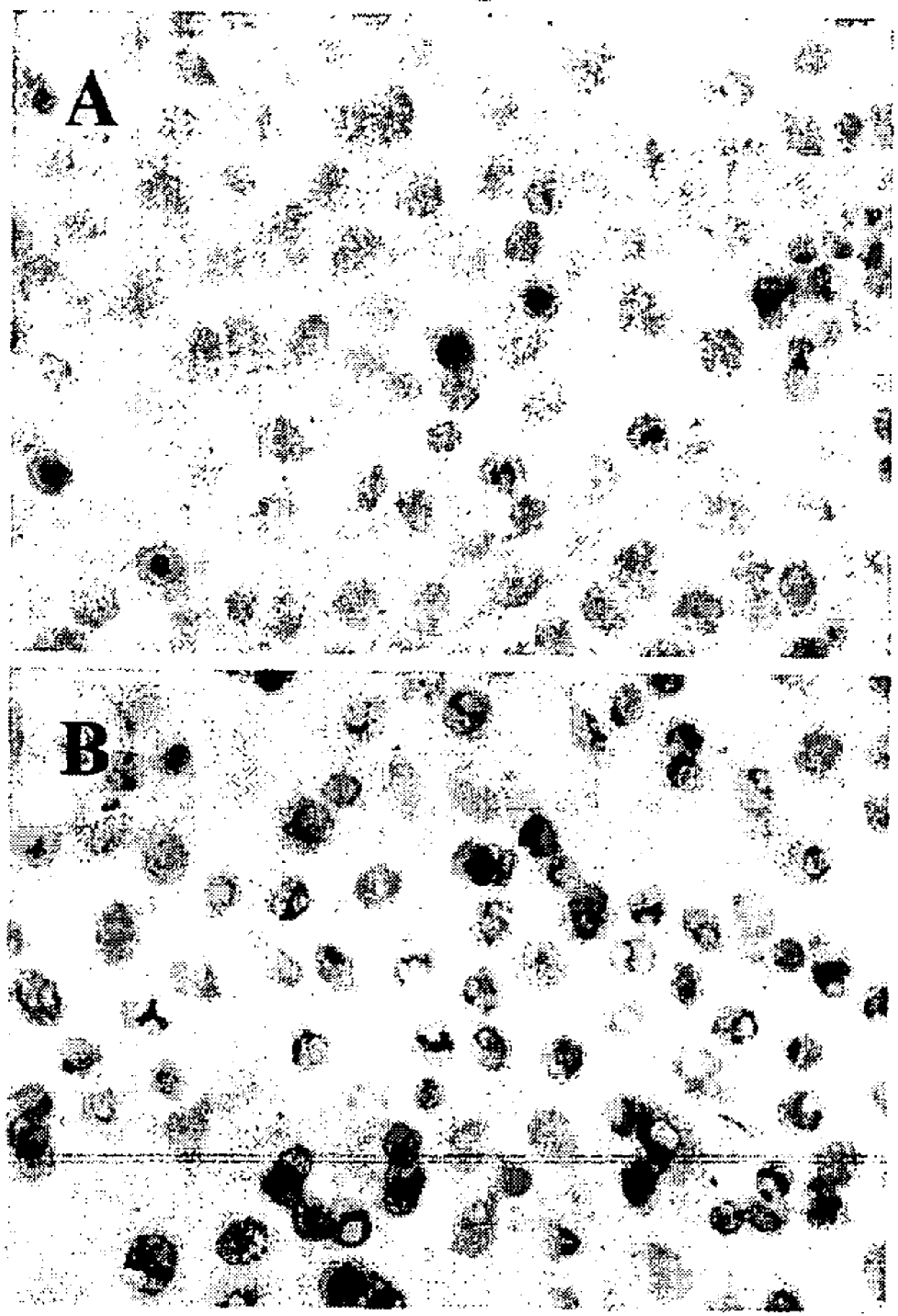

FIG. 8. Immunostaining of casein in Tc-regulated MDA-MB-468 pRB-clone 19. (A), medium containing 0.5 µg of Tc; (B), in Tc-free medium. Overexpression of pRB in RB-reconstituted MDA-MB-468 breast carcinoma cells led to a terminal differentiation phenotype, as evidenced by increased expression of the milk protein casein and accumulation of intracytoplasmic lipid droplets, both are biomarkers associated with breast cell differentiation. The MDA-MB-468 pRB-clone cells in Tc-free medium are arrested in G1/G0 phase of the cell cycle, exhibiting mature cell morphology, characterized by lacy nuclei surround by sizeable cytoplasms. It appears that overexpression of pRB in $RB^{-/-}$ tumor cells of our models results in cell differentiation, endogenous GrB-NIC expression, and apoptosis of bystander $pRB^-$ (or low pRB) cells, while presence of ectopic pRB in these tumor cells prevents cell death induced by their own GrB-NIC.

Figure 9:
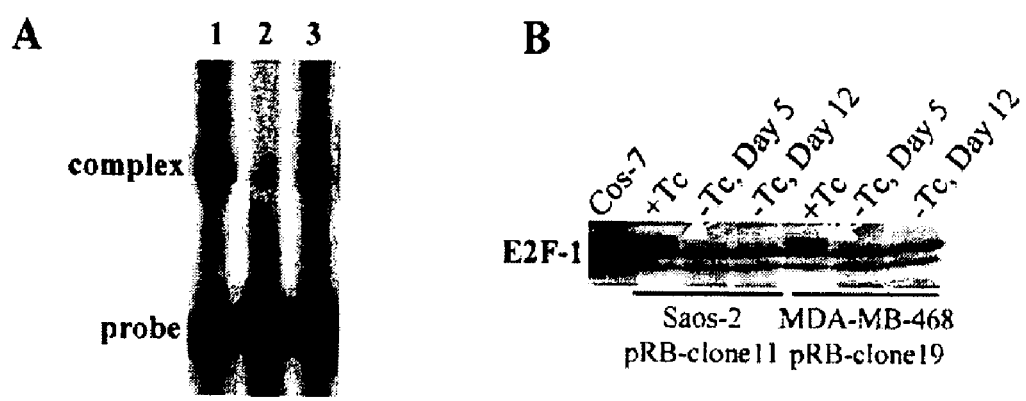

FIG. 9. GrB-NIC promoter and the E2F-1 transcription factor. (A) EMS assay showed sequence-specific binding of E2F-1 with GrB-NIC promoter. A Ban II/Pvu II fragment (−180 to +15) of the GrB-NIC promoter, containing a putative E2F site, was $^{32}$P-labeled and incubated with cell extracts prepared from pCMV.E2F-1 plasmid-transfected Saos-2 cells (Lane 1). Cold DNA fragments, containing either the wild-type (Lane 2) or mutated (Lane 3) E2F site, were added as competitors. (B) Western blotting analysis showed changes in phosphorylation of E2F-1 in RB-reconstituted Saos-2 and MDA-MB-468 cells. Cell lysates from Saos-2 pRB-clone 11 and MDA-MB-468 pRB-clone 19 in 0.5 µg/ml of Tc (+Tc), or in Tc-free medium (−Tc) as indicated were analyzed. pCMV.E2F-1 plasmid-transfected Cos-7 cells was used as E2F-1 protein control (Cos-7). E2F-1 was nearly completely dephosphorylated upon pRB-mediated growth arrest. Arrows, phosphorylated E2F-1. Anti-E2F-1 KH95 monoclonal antibody (PharMingen) was used for the assay.

Figure 10:
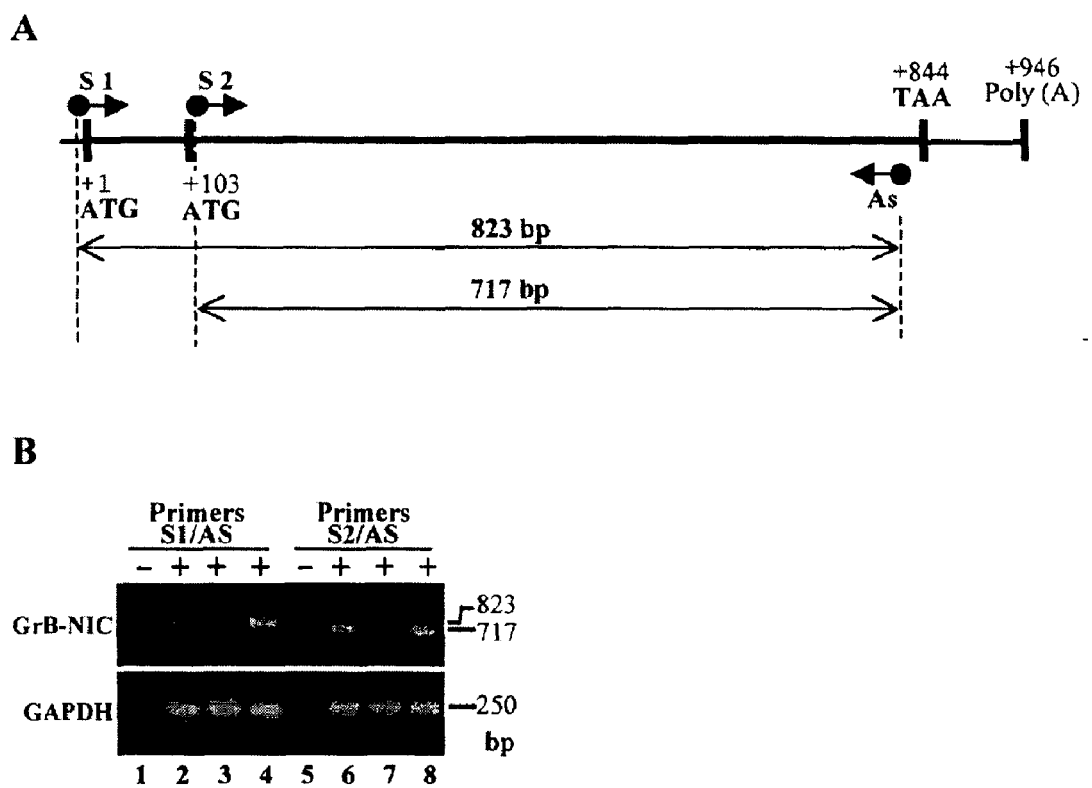

FIG. 10. GrB-NIC transcripts in human normal embryonic neuronal cells. (A) A schematic representation of human GrB-NIC cDNA and locations of PCR primers used in this study. (B) RT-PCR was performed on 0.1 µg of total RNAs from: Lane 1–2 & 5–6, human embryonic neurons (lane 1 & 5, without primers); Lane 3 & 7, Cos-7 (GrB-NIC negative control); Lane 4 & 8, Saos-2 pRB-clone 11 cells in Tc-free medium (GrB-NIC positive control). Primers were designed to amplify GrB-NIC mRNA corresponding to nucleotide sequences (Primer S1/AS) +143/+965 (823 bp, covering the first AUG start codon), and (Primer S2/AS) +249/+965 (717 bp, starting at the second AUG codon). The same RNA samples were subject to RT-PCR amplification of the GAPDH housekeeping gene transcripts (a 250-bp fragment). The results from RT-PCR analysis indicated that GrB-NIC mRNA from human neuronal cells indeed contained the upstream AUG codon, identical to the endogenous granzyme B (GrB-NIC) mRNA in Saos-2 osteosarcoma cells upon pRB-mediated senescent arrest.

Figure 11:
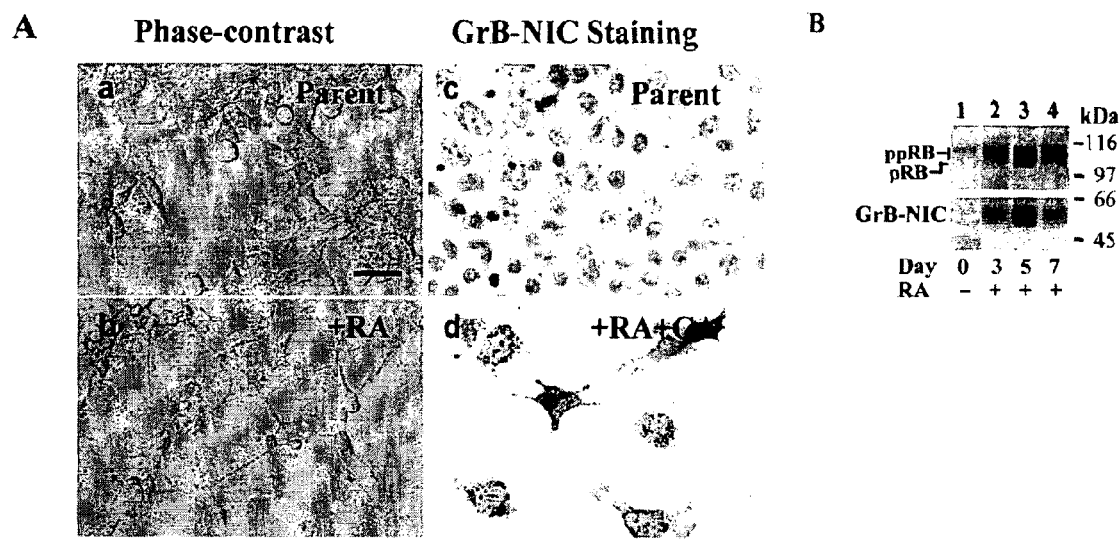

FIG. 11. Detection of mouse GrB-NIC proteins by immunochemical staining (A) and Western Immunoblotting (B) in differentiating P19 neuronal cells. (A) Morphology of parental P19 cells in exponential growth phase (Panel a) and RA-induced differentiating P19 neuronal cells (Panel b) was illustrated by phase-contrast photography. Immunostaining showed that the parental P19 cells were GrB-NIC negative (Panel c), and the differentiating P19 neuronal cells (after further treatment with cytosine arabinoside to eliminate glial cells) were GrB-NIC positive (Panel d). (B) Western blotting analysis of mouse pRB and GrB-NIC in parental P19 (Lane 1), and RA-treated P19 spheroids (exposed to RA for 48 h) at Day 1, 3, and 5 after plating (Day 3, 5, and 7 after treatment with RA) (Lanes 2–4). The GrB-NIC was detected in differentiating P19 neuronal cells, coincident with elevated expression of pRB (Lanes 2–4), with peak levels at Day 5 after RA treatment (i.e., Day 3 after plating), but not in the parental P19 cells (Lane 1). Anti-GrB polyclonal antibodies N-19 (Santa Cruz) were used, which recognized mouse glycosylated GrB. RA, retinoic acid; CA, cytosine arabinoside; ppRB, phosphorylated RB protein; pRB, underphosphorylated RB protein.

Figure 12:
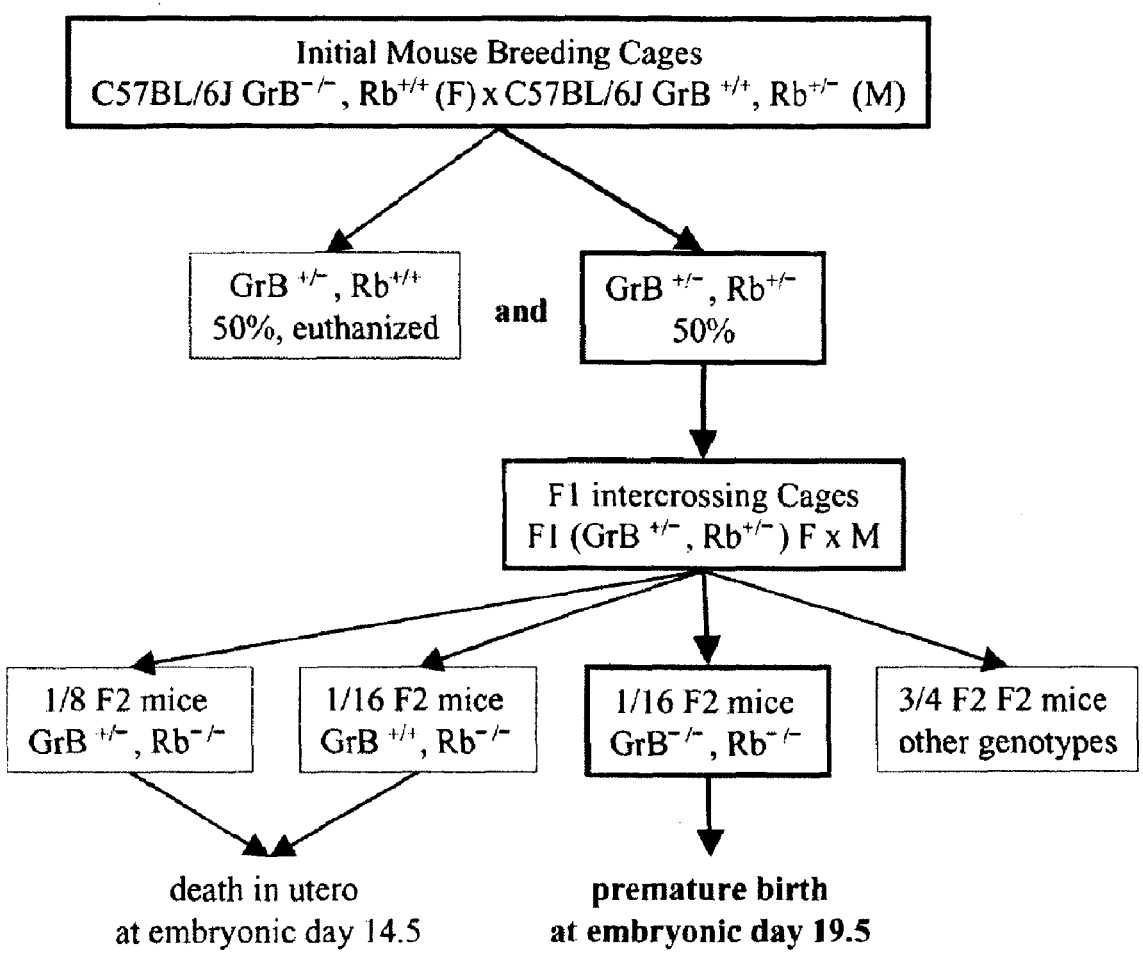

FIG. 12. The RB and GrB-NIC Double-mutant Mouse Embryos Extended Survival to Approximately Embryonic Day 19.5 (E19.5): A Schematic Diagram of the Breeding Scheme.

Figure 13:
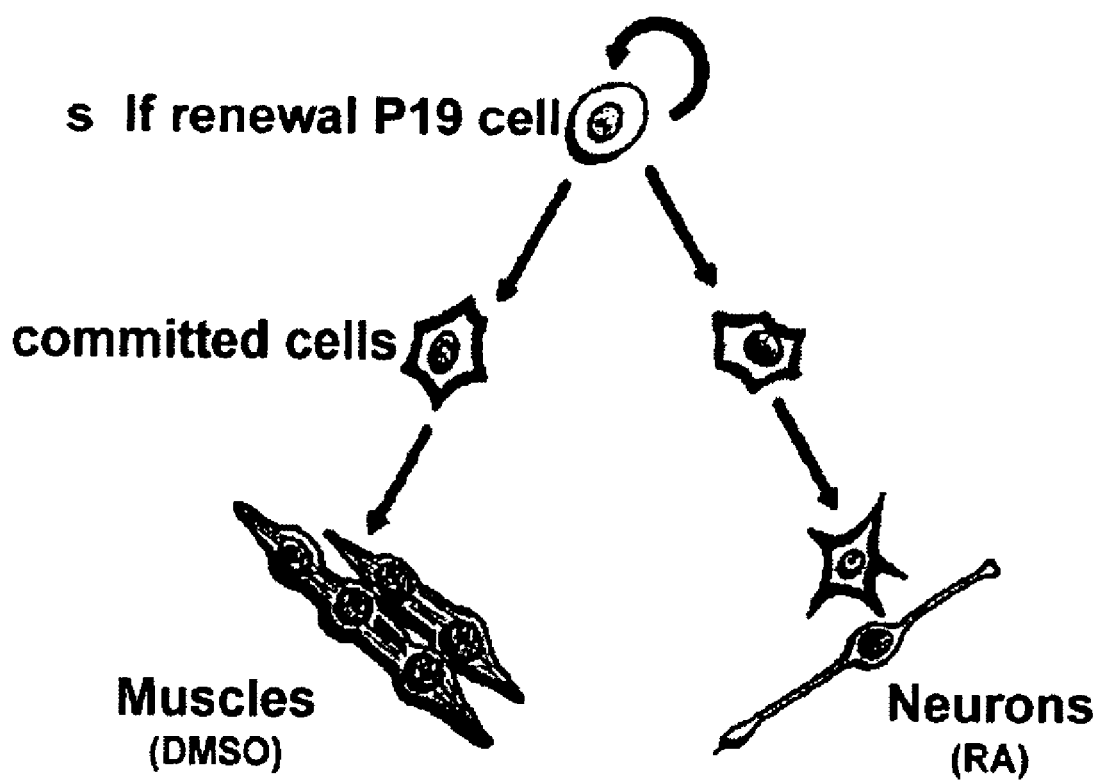

FIG. 13. P19 teratocarcinomas stem cell two-alternative differentiation model showing the relationship between stem cells and their committed and differentiated derivatives. Shown at the top of the diagram is the stem cell. Its ability for self renewal is indicated by a semicircular arrow. Morphologically undifferentiated but developmentally restricted (committed precursor) cells are represented by the second tier of cells, and the fully differentiated cells are shown in the bottom row denoting neurons and glial cells (induced by RA) and muscles (induced by DMSO).

FIG. 14. Targeting the nearly silent GrB-NIC gene in P19 embryonal carcinoma stem cell line by homologous recombination. Maps of the genomic region encompassing the GrB-NIC gene and the targeting vector are diagramed. The sizes of the EcoRI fragments expected from the wild-type and disrupted alleles are also indicated. Note that the novel targeting vector specially designed for disrupting a nearly silent gene in mammalian cells is promoterless for the modified tTA (mtTA) cassette, while the neoR gene is placed downstream the mtTA-dependent promoter (pCMV*-1). After sequential disruption of two GrB-NIC alleles, no wild-type-specific 4,164 bp EcoRI fragments are present in the knockout cells.

Figure 15:
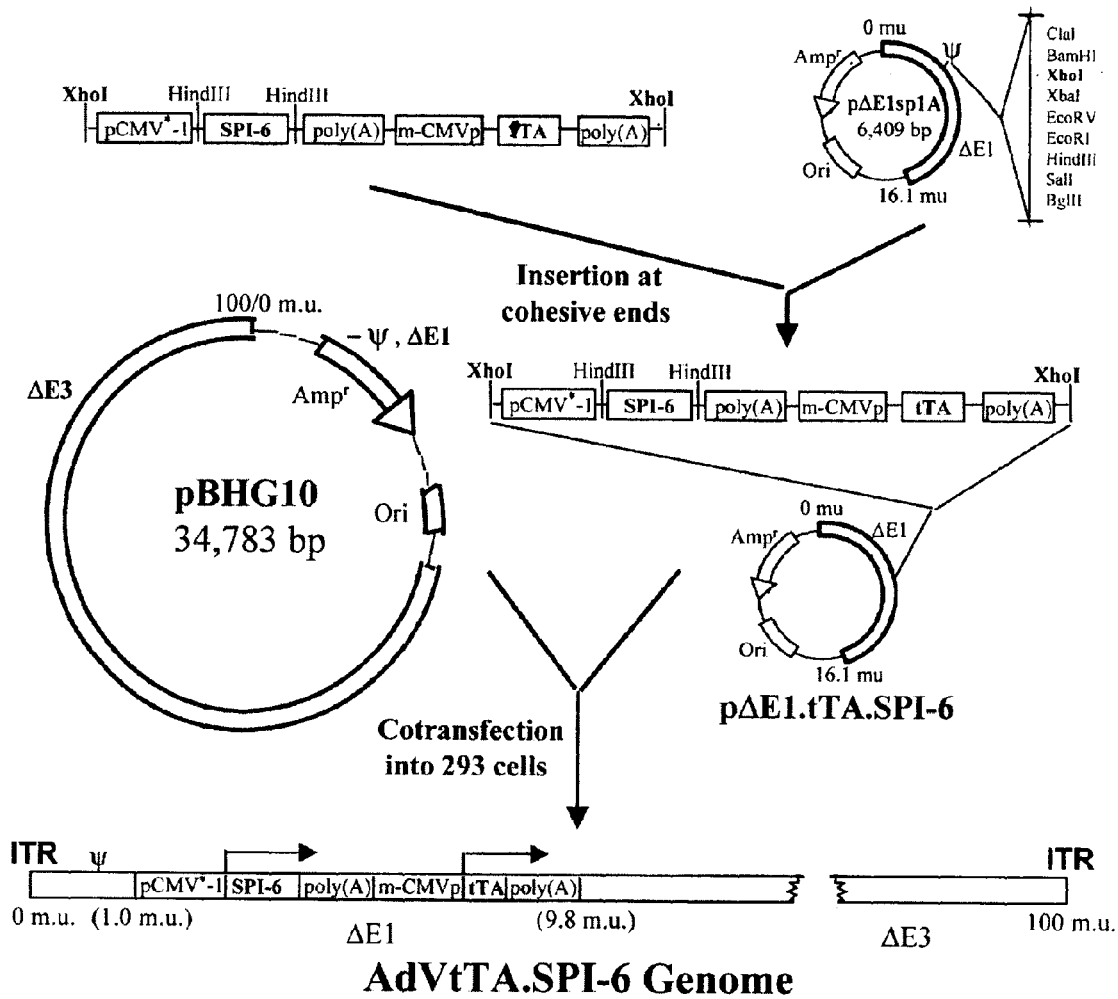

FIG. 15. Construction of the replication-deficient recombinant adenovirus, AdVtTA.SPI-6 and schematic representation of its genome. In the resultant recombinant virus, a large portion of the E1a and E1b region (1.0–9.8 m.u.) of the Ad5 genome was replaced by a modified tTA expression cassette and a tetracycline-responsive SPI-6 expression cassette. tTA, tetracycline-controlled transactivator, pCMV*-1, tTA-dependent promoter, m-CMVp, modified CMV promoter, ψ, Ad5 packaging signal sequence.

Figure 16:
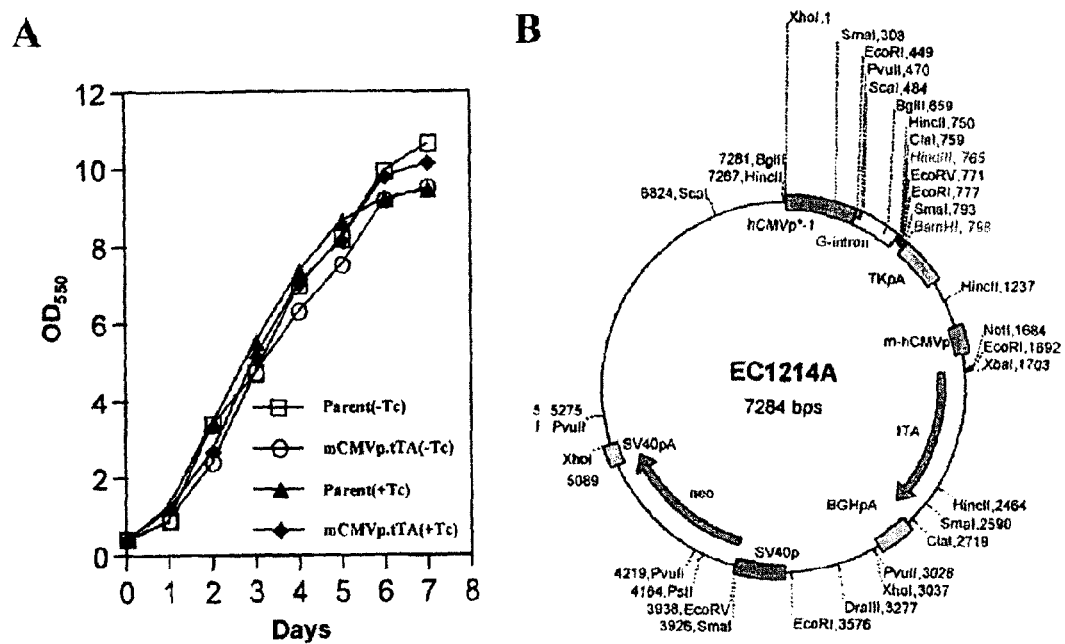

FIG. 16. (A) Expression of the modified m-tTA has no squelching effects on the host 5637 cell growth. (B) The modified, single-plasmid tetracycline-responsive gene expression system, EC1214A.

Figure 17:
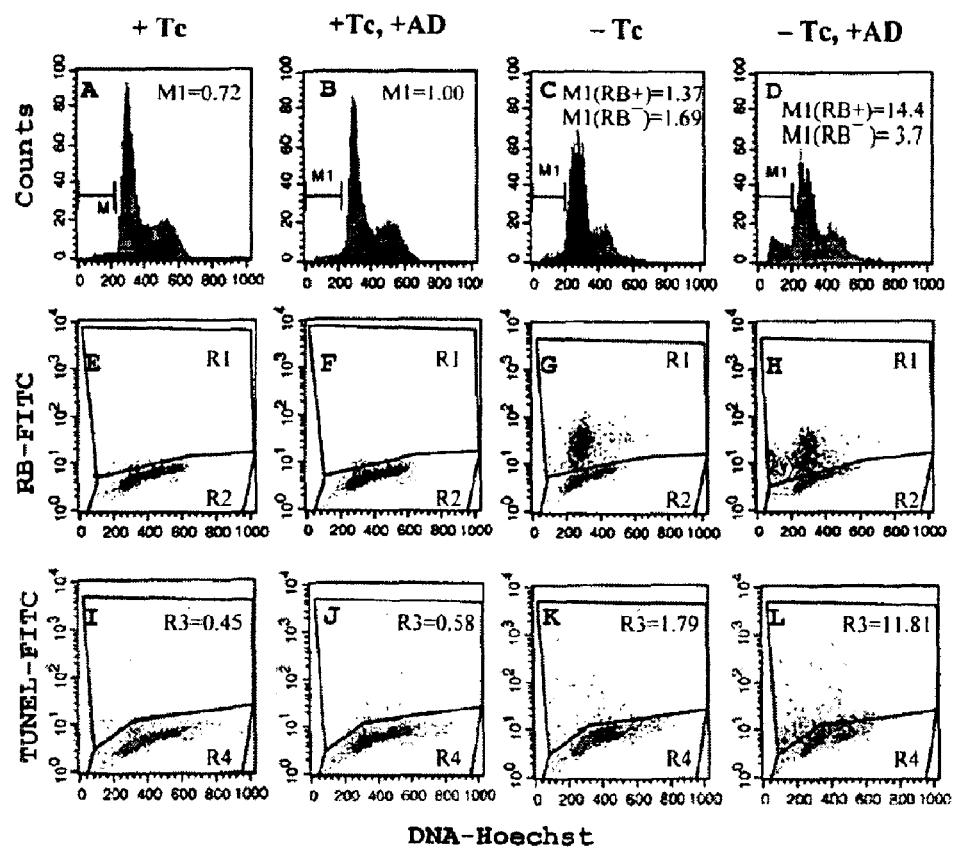

FIG. 17. GrB-NIC-associated apoptosis is accelerated by infection with adenovirus, a substitute for perforin. Parental Saos-2 (pRB$^-$) tumor cells were added, in an approximate 1:1 ratio, to RB-reconstituted Saos-2 pRB-clone 11 cell monolayers that had been grown in Tc-containing (+Tc, pRB$^-$/GrB-NIC$^-$) or Tc-free (–Tc, pRB$^+$/GrB-NIC$^+$) medium for 4 days, and the mixed cultures were infected with a replication-deficient adenovirus, AdV β-gal (AD) as indicated (multiplicity of infection of 100) (Xu et al., 1996). Three hours after removal of AD supernatant, all cell cultures were harvested and processed for dual-parameter FACS analysis (RB or TUNEL labeling versus DNA content). (A–D) Histograms depict DNA content profiles of pRB$^+$ (red) and pRB$^-$ (green) cells in the mixed cultures. M1, sub-G1 phase. Note that after infection with AD, the number of pRB$^+$ sub-G1 cells was increased to 14.4% (Panel D), from 1.37% before AD infection (Panel C). (E–H) Dot plots depict dual-parameter profiles of pRB-FITC versus DNA-Hoechst. Gate R1, pRB$^+$; R2, pRB$^-$. (I–L) Dot plots depict dual-parameter profiles of TUNEL-FITC versus DNA-Hoechst; R3, TUNEL-positive labeling; R4, TUNEL-negative labeling. The apoptotic nature of the sub-G1 cells was confirmed by TUNEL-positive labeling (compare Panel L with D & H). All the profiles shown here were from a single experiment representative of at least three independent experiments with similar results. Panel A, B, E, F, I, and J, mixed cultures in medium containing 0.5 µg/ml of Tc, all cells including both Saos-2 pRB-clone 11 and parental Saos-2 were pRB$^-$, and AD infection had no effect in these cultures (B, F, J).

Figure 18:
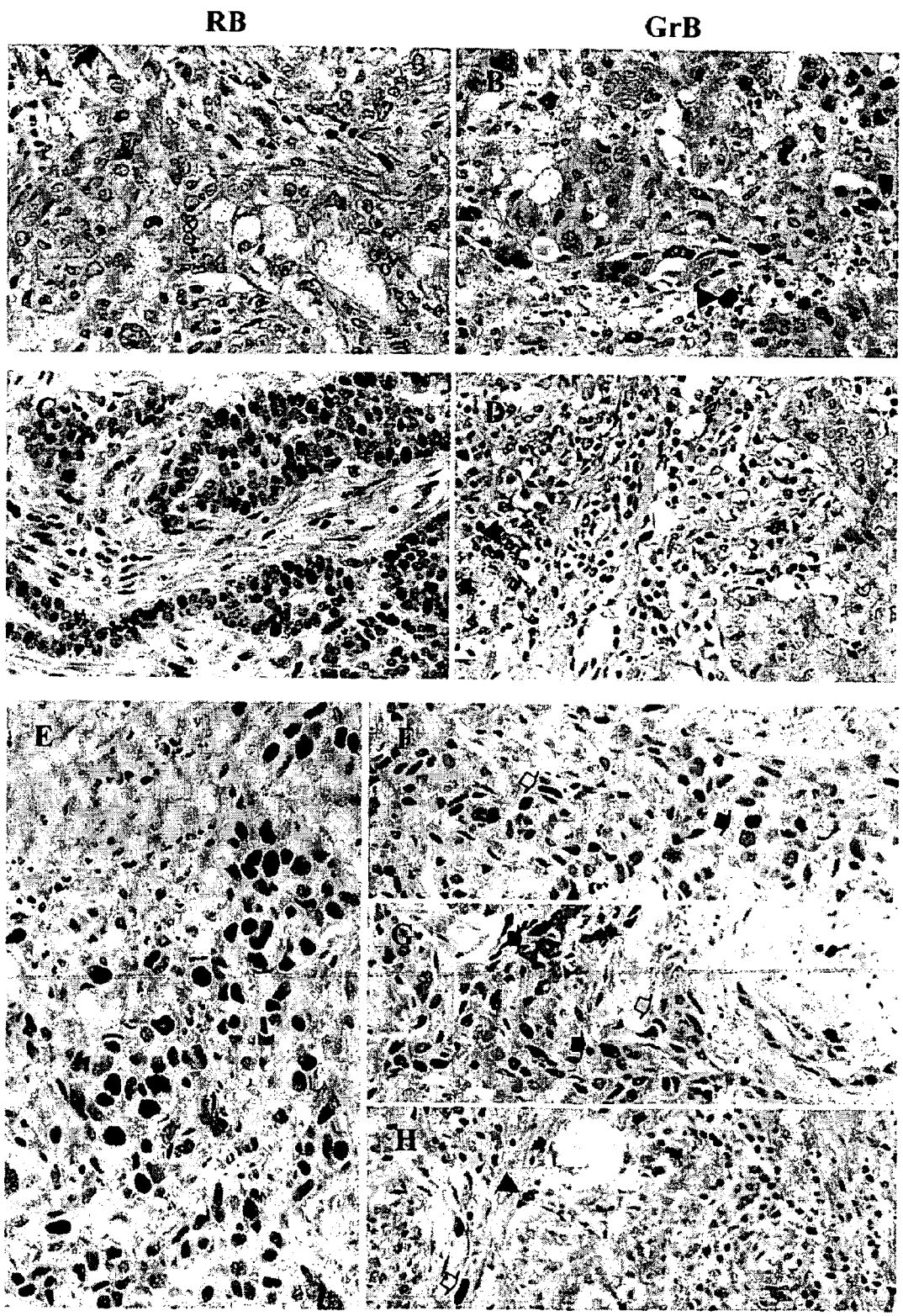

FIG. 18. Detection of endogenous GrB-NIC in primary breast carcinomas overexpressing pRB (pRB$^{++}$) by immunohistochemical staining of paraffin-embedded tissue sections. (A, C, and E) pRB staining, showing typical pRB$^-$ (A), pRB$^+$ (C), and pRB$^{++}$ (E) tumors. Note that the tumor cells in panel E (pRB$^{++}$) display uniformly strong pRB staining, while the tumor cells in panel G (pRB$^+$) show nuclear staining heterogeneity of the RB protein, ranging from quite positive to seemingly negative (15). (B, D, and F–H) The same tumors corresponding to the left panels were stained for GrB-NIC. Panel B and D, in either pRB$^-$ (B) or pRB$^+$ (D) tumors, malignant cells are GrB-NIC negative, but some infiltrating lymphocytes are GrB$^+$. Panels F–H, representative areas of the same pRB tumor shown in Panels E. GrB-NIC$^+$ tumor cells (F, G), or lymphocytes (H) were evident. Note the finely granular distribution of endogenous GrB-NIC protein in tumor cells of Panel G. Arrowheads, GrB$^+$ lymphocytes; solid arrows, GrB-NIC$^+$ tumor cells; open arrows, GrB-NIC$^+$ mesenchymal and endothelial cells. Scale bar, 50 µm.

Figure 19:
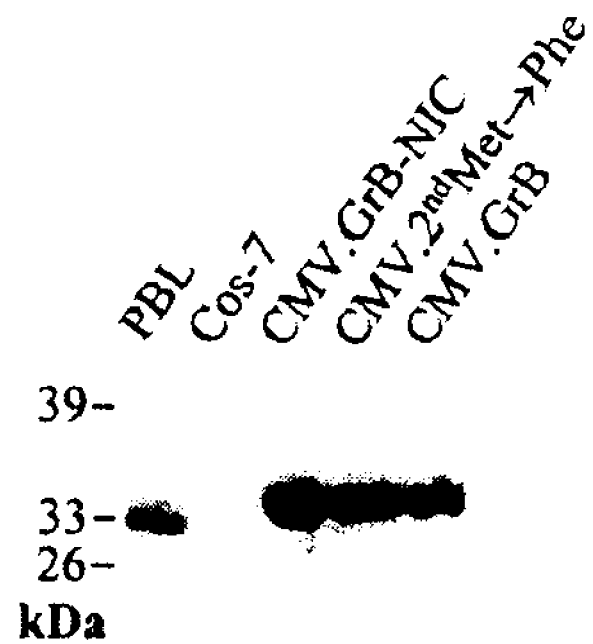

FIG. 19. Analysis of GrB-NIC and cytotoxic lymphocyte GrB expression in Cos-7 cells through plasmid constructs: evidence for an authentic translation initiation AUG site in vivo. COS-7 cells transfected with plasmids expressing a wild-type GrB-NIC cDNA (pCMV.GrB-NIC), a second AUG codon (the native authentic translation initiation site for cytotoxic lymphocytes GrB)-mutated version of GrB-NIC cDNA (pCMV.2$^{nd}$Met Phe), or a wild-type lymphocyte GrB cDNA (pCMV.GrB), all produced immunoreactive proteins of the same size ~33 kDa) as determined by immune Western blotting.

FIG. 20. The Chromosomally Integrated GrB-NIC Promoter Is Transcriptionally Activated in Normal and Malignant Osteoblasts upon Cell Differentiation. A, Tc-regulated, RB-reconstituted Saos-2 cells, and B, subclone 4 (Ascorbic acid-sensitive) and subclone 24 (Ascorbic acid-insensitive) of the normal mouse MC3T3-E1 osteoblast cell line were stably transfected with a GrB-NIC promoter-luciferase reporter plasmids. Luciferase reporter activity was significantly increased in pRB-induced differentiating Saos-2 transfectants in Tc-free medium (A), and in ascorbic acid (50 µg/ml)-stimulated differentiating MC3T3-E1 subclone 4 cells with an integrated GrB-NIC promoter-luc construct, but not in the ascorbic acid-insensitive MC3T3-E1 subclone 24 transfectants (B). All experiments were repeated at least twice.

DETAILED DESCRIPTION OF THE INVENTION

The instant invention relates to the discovery and subsequent isolation of a nucleic acid sequence that encodes a novel protease precursor (pre-enzyme, preproenzyme, or zymogen) for endogenous granzyme B in non-immune cells, designated GrB-NIC. The discovery was based on the observation that the constitutively nearly silent GrB locus in breast and osteosarcoma tumor cells is transcriptionally activated during pRB-induced growth arrest and cell differentiation. The cloned cDNA from this locus predicts a protease precursor that shows complete amino acid identity to the cytotoxic lymphocyte-produced GrB zymogen, but is 34 amino acids longer at the amino terminus. Nonetheless, both endogenous GrB in non-immune cells (GrB-NIC) and GrB from cytotoxic lymphocytes have the same enzymatic specificity. Consequently, solid tumor cells with accumulated GrB-NIC undergo post-growth-arrest apoptosis and induce apoptosis of bystander tumor cells through an exocytosis/endocytosis mechanism.

As set forth herein, SEQ ID NO. 1 corresponds to the nucleic acid sequence of the putative mRNA of GrB-NIC extending from the transcription start site to nucleotide 1092 of FIG. 1. SEQ ID NO. 2 corresponds to the nucleic acid sequence extending from the codon encoding the 5' Met of GrB-NIC to nucleotide 1092 of FIG. 1. SEQ ID NO. 3 corresponds to the amino acid sequence of GrB-NIC including the signal peptide. SEQ ID NO. 4 corresponds to the nucleic acid sequence extending from the codon encoding the 5' Met of GrB-NIC to the stop codon of the GrB-NIC transcript. SEQ ID NO. 5 corresponds to the nucleic acid sequence of the cloned GrB-NIC cDNA extending from nucleotide 141 (the start of GrB-NIC cDNA) to nucleotide 1092 of FIG. 1. SEQ ID NO. 6 extends from nucleotide +1 (a major transcription start site of GrB-NIC cDNA) to nucleotide 1092 of FIG. 1.

The instant invention also relates to the observation that there is a marked increase in GrB-NIC activity in differentiating neuronal cells. Terminally differentiated neurons maintain exceptionally high levels of pRB and GrB-NIC over their entire lifetime. This reflects that during embryonic neuronal development, the "birthday"- and "birthplace"-specific differentiating and differentiated neurons may physiologically express GrB-NIC to eliminate neighboring dividing neuronal precursor cells which have a low level of pRB after metaphase. This mechanism provides a simple way to eliminate "out-of-date" or misplaced cells, for regulating total nerve cell numbers and, perhaps, for selecting the most competitive, fittest neuron cells. In adults, GrB-NIC can protect the nerve tissue against invading pathogens or immune-mediated damage, but the latter function fails increasingly with age or disease-specific genetic alterations; an excessive accumulation of the intrinsic GrB-NIC activity late in life may cause nerve cells to die, contributing to degenerative neurological disorders (such as Parkinson's and Alzheimer's diseases).

Interestingly, p53 can induce endogenous GrB-NIC in the absence of pRB, resulting in rapid apoptosis of pRB mutant cells. Accumulation of unphosphorylated (active) free E2F-1 in RB-reconstituted cells could eventually account for transcriptional activation of the otherwise silent GrB-NIC gene. In considering that GrB induces apoptosis by activating downstream caspases or through a Bcl-2-inhibitable mitochondrial pathway (GrB-mediated cytochrome c release), all current available data suggests that there is critical requirement for both pRB and endogenous GrB (GrB-NIC) by neural cells during embryonic neuronal development, particularly in the first phase of neuronal development (genesis of neurons), to eliminate neural stem cells as early as the phase is completed. Expression of endogenous GrB (GrB-NIC) in differentiating and mature neurons may be responsible for massive neuronal cell death in RB or Bcl-x mutant mice, while caspase-3 might play a role mainly in late phases, involving morphogenesis of the nervous system— most types of neurons in the vertebrate central and peripheral nervous system are produced in excess; up to 50% or more of them then die soon after they reach their target (normal target-related neuronal death).

Definitions

As used herein, "a" or "an" may mean one or more. As used herein in the claim(s), when used in conjunction with the word "comprising", the words "a" or "an" may mean one or more than one. As used herein "another" may mean at least a second or more.

As used herein, "native" refers to a nucleic acid or protein sequence as it generally occurs in nature.

As used herein, "cloned nucleic acid" refers to an isolated nucleic acid sequence subsequently engineered or inserted onto or into another nucleic acid molecule.

Induction of an Endogenous Granzyme B in Human Non-hematopoietic Cells

The instant invention includes the identification of an endogenous version of the cytotoxic lymphocyte-specific GrB in human non-hematopoietic, non-immune cells. Expression of GrB-NIC in breast carcinoma and osteosarcoma cells upon pRB-mediated growth arrest was determined at the mRNA level by RPA assay, Northern blotting and nucleotide sequencing analysis; at the protein level by Western blotting and immunochemical staining; and at the biochemical/biological function levels by enzymatic and apoptosis assays. The GrB-NIC transcript detected on the Northern blot is larger than the lymphocyte GrB mRNA, intimating alternative promoter usage. Post-translational processing of GrB-NIC and GrB (that is, signal peptidase cleaves away the signal peptide from the N-terminus, and then the dipeptide $Gly_{53}$-$Glu_{54}$, or $Gly_{19}$–Glu20 if the second AUG codon used by lymphocyte GrB is assigned +1, is removed by DPPI) (Smyth et al., 1995), generates the same mature or active enzyme, as demonstrated by deglycosylation assay. Differential usage of promoters at the GrB locus may be a mechanism to allow tissue-specific regulation of this deadly protease at the transcription level.

Comparison With Induction of Endogenous GrB in Activated Keratinocytes

Berthou et al., 1997, reported the expression of GrB in mobilized hematopoietic $CD34^+$ progenitor cells and confluent epidermal keratinocytes (Berthou et al., 1995; Berthou et al., 1997). However, expression of the GrB mRNA was demonstrated only by in situ hybridization using antisense GrB RNA probes. The method was not able to determine the extent of the nucleotide sequence identity between more or less closely related RNA species, nor the size of the transcripts. Consequently, this article does not report nor postulate that the detected transcript was anything other than a molecule identical with that observed in thoroughly characteristic lymphocytes, particularly CTLs and NK cells. Independent studies reported by others failed to detect GrB mRNA expression in mobilized hematopoietic $CD34^+$ progenitor cells when S1 nuclease protection assay was employed (Graubert et al., 1997). Nevertheless, we have recently detected immunoreactive GrB proteins of high molecular mass in primary keratinocyte cultures by Western blotting, which can be reduced by deglycosylation to 26 kDa, a size identical to nonglycosylated mature GrB in lymphocytes; even though we were unable to detect GrB transcripts in either preconfluent or confluent keratinocytes on Northern blots or by S1 nuclease protection assay (Hu et al., 2003). The combined results indicate that endogenous GrB proteins accumulate in keratinocytes with extremely low mRNA levels (undetectable by conventional Northern blotting and S1 nuclease protection assay). According to Berthou et al., activated keratinocytes are able to protect against invading pathogens through GrB expression (Berthou et al., 1997).

Furthermore, primary keratinocyte cultures have elevated pRB expression; the RB protein, however, was dephosphorylated and reduced about tenfold in keratinocytes grown to confluence (data not shown). Still more telling is the fact that during epidermal differentiation in vivo, the post-proliferating keratinocytes in the suprabasal layers continue to overexpress pRB during the early transitional phase which is followed by an inevitable decline of pRB immunoreactivity and apoptotic death of the terminally differentiated cells (Cordon-Cardo and Richon, 1994; Xu, 1995). Overexpression of pRB also appears to be common in naturally occurring malignant cells with an as yet undisrupted RB gene, and in normal tissues adjacent to tumor masses (Xu, 1995). In additional, endogenous GrB has been detected in vivo in a subset of breast tumors and normal stroma, that coincides with overexpression of pRB in tumor cells and reactive mesenchymal and endothelial cells (FIG. 18). Hence, overexpression of pRB likely contributes to a common pathway of induction of GrB-NIC in non-hematopoietic cells; and the RB-reconstituted cell lines used in our studies might be partly mimicking the local events of host defense in vivo.

The pRB-Mediated Post-growth-arrest Apoptosis

The striking similarity between GrB-NIC and the cytotoxic lymphocyte-specific GrB supports the idea that up-regulation of GrB-NIC is a major event in pRB-induced post-growth-arrest apoptosis. There are apparent inconsistencies in the literature on the effects of RB replacement in tumor cells lacking functional pRB, which underscore the complexity of modeling gene functions in any experimental system. Early studies on RB replacement into RB-defective tumor cell lines through transient plasmid transfection or retrovirus infection showed massive cell death and dramatic cell growth suppression (Huang et al., 1988; Qin et al., 1992), which might be attributed to RB dosage effects (Bignon et al., 1993). On the other hand, establishing stable RB-reconstituted clones for functional studies also has some major drawbacks, including the possible bias toward selecting rapid-growing tumor cell clones, or the RB-deficient tumor cells may adapt to the gain of RB function, resulting in pRB-resistant clones throughout the cloning process. In support of this view, long-term stable clones of the RB-reconstituted tumor cells had been obtained in culture that grew just as rapidly (and indefinitely) as their parental lines (Chen et al., 1992; Zhou et al., 1994). As reflected herein, an improved Tc-regulated RB gene expression system is disclosed that minimizes the selection bias after RB reconstitution, because expression of pRB in transfected cells can be effectively turned off during cloning and subcloning. This system allowed successful demonstration that reexpression of functional pRB alone in RB/p53-defective tumor cells resulted in irreversible growth arrest and apparent resistance to apoptosis (Xu et al., 1997). The disclosed studies further demonstrate that when the pRB-mediated growth arrest took place as the result of pRB overexpression, it became strictly dependent on continuing overexpression of the functional pRB as well as maintaining its integrity; the inevitable post-growth-arrest cell death was consistent with apoptosis, which occurred concurrently with accumulation of GrB-NIC and proteolytic cleavage of the pRB protein.

Regulation of GrB-NIC, Watchman of the Cell Cycle

The inability to maintain a precise E2F-1 homeostasis in RB-reconstituted tumor cells (or in cells that overexpress pRB as part of their stress response to a variety of alterations) could eventually account for transcriptional activation of the otherwise silent GrB-NIC gene, with a fatal outcome. One of the fundamental differences between pRB-mediated senescence-like growth arrest and bona fide replicative senescence is perhaps that overexpression of pRB causes compromised cellular homeostasis, such as an imbalance in the ratio of unphosphorylated to phosphorylated E2F-1 proteins (FIG. 9). Down-regulation of E2F-1 in S phase through phosphorylation, reducing its affinity for DNA and preventing transcription of E2F-1 regulated genes, is important in cellular homeostasis because of the dual functions of E2F-1 as a critical regulator of apoptosis and cell proliferation (Dyson, 1998). It is noteworthy that there was a balanced E2F-1 phosphorylation pattern even in the pCMV.E2F-1 plasmid-transfected Cos-7 cells, in which ectopic expression of E2F-1 reached very high levels (see FIG. 9, E2F-1 control). The disappearance of phosphorylated E2F-1 proteins in RB-reconstituted cells is itself a sign of cell cycle progression out of equilibrium. Overexpression of E2F-1, or expression of a nonphosphorylatable, constitutively active form of E2F-1, can lead to S-phase entry or S/G2 arrest followed by apoptosis (Krek et al., 1995; Shan et al., 1996).

The promoters of GrB locus have two interesting features. First, the core promoter fragment for GrB-NIC comprises mainly consensus sequences, including CCAAT box, AP-1, and E2F-like sites, that are common in many cell cycle-regulated promoters; while the 5'-proximal region of GrB coding sequence contains additional cis elements believed to be essential for its transcription in activated lymphocytes such as NF-AT. Second, although the GrB locus is constitutively nearly silent, the GrB-NIC promoter fragment examined in plasmid constructs is transcriptionally active in non-hematopoietic, non-immune cells. The GrB-NIC promoter-driven CAT reporter gene activity is comparable with promoters of many housekeeping genes that are ubiquitously expressed, such as the RB promoter (FIG. 2D). The same is true for a murine GrB promoter fragment, which conferred high levels of luciferase reporter gene activity in transient transfection assays into T cells as well as mouse fibroblasts, in spite of the fact that transcription of GrB is CTL specific, and no GrB mRNA is detectable in resting T cells or fibroblasts (Babichuk et al., 1996). It has been proposed that a condensed (closed) chromatin structure at the natural GrB locus may be responsible for its silence in non-T cells (Babichuk et al., 1996).

Taken together, these findings indicate that abrogation of E2F-1 homeostasis during pRB-mediated G1 arrest leads to unprepared cell-cycle reentry (as illustrated by $^3$H-labeled deformed nuclei in FIG. 5C, b & c). Once the cells are in late G1/early S phase, the chromatin structure surrounding the GrB locus may adopt an open conformation (Brehm and Kouzarides, 1999). The excessive unphosphorylated (active) E2F-1 gains access to the GrB-NIC promoter and initiates derepression of the promoter. The resultant GrB-NIC protein, a watchman of the cell cycle, whose mature form is not distinguished from GrB of lymphocyte origins, can cleave pRB either directly (Sun et al., 2001) or through activation of other downstream executioner caspases (Yang et al., 1998). This process, once initiated, is self-sustaining until clearance of all functional pRB and full activation of the GrB-NIC gene, leading to post-growth-arrest apoptosis. Withdrawal or reduction of pRB expression in the Tc-regulated clone cells demonstrates this process in a relatively synchronous manner.

As further disclosed herein, in RB-reconstituted clone cells, GRB-NIC transcription is not proportional to protein accumulation. For example, the RB-reconstituted Saos-2 cells express more GrB-NIC at the transcript level, but less at the protein level, than the RB-reconstituted MDA-MB-468 cells. A polar distribution of GrB-NIC proteins is clearly seen in Saos-2 cells, but it is less evident in MDA-MB-468 cells, where GrB-NIC is mostly localized in the cytoplasmic-perinuclear region (see FIG. 3A, confocal images). Indicating that additional mechanisms for regulating GrB-NIC, which may include translation, glycosylation and intracellular trafficking, may exist.

Broader Implications of Induction of Endogenous GrB-NIC Expression

An endogenous GrB in non-hematopoietic, non-immune cells is identified herein as one of the critical molecules responsible for pRB-mediated post-growth-arrest apoptosis and bystander cell death. The presence of GrB-NIC may implicate a potential defense mechanism in vivo against neoplastic cells through induction of GrB activity that is intrinsic to the aberrant/damaged (or normal reactive) cells, rather than acquisition of GrB secreted by lymphocytes. The novel GrB-NIC pathway might be complementary to the existing paradigm for cytotoxic lymphocyte-mediated target cell death, allowing synergistic interactions between the local mechanism of defense and the immune system. As an example, CTLs from mice deficient in both GrB and FasL reportedly induce apoptosis of allogeneic targets through an intact late cytotoxicity pathway, which is primarily accounted for, according to the authors, by a perforin-dependent mechanism (Shresta et al., 1997), and in which granzyme A (or other tightly linked genes) has been proposed to play a part (Shresta et al., 1999). Given the knowledge of an intrinsic GrB-NIC in human non-hematopoietic, non-immune cells, the results also invites speculation on the possible interaction between perforin from CTLs and endogenous GrB activity of the target cells. The lymphocyte perforin may accelerate intracellular trafficking of the endogenous GrB in allogeneic target cells and thus the processes of apoptosis.

Interestingly, while GrB produced by tumor-infiltrating lymphocytes (TIL) has been reported to be involved in suppression of tumor progression in cancer patients, a recent paper reported that GrB was in fact distributed in the cytoplasm of cancer cells rather than in TIL (Kontani et al., 2001). The study was done on tumor tissues derived from patients with breast or lung cancer, including both early and late stage tumors. By assuming cancer cells may acquire GrB released from TIL, the study concluded that the percentage of cancer cells positive for GrB was inversely correlated with the status of regional lymph node metastasis. Identification of an endogenous GrB (GrB-NIC) directly expressed in non-immune cells provides a rational basis for the contemplated clinical significance of GrB-NIC expression in human cancers. Indeed, by immunohistochemical staining of paraffin-embedded tumor sections, GrB-NIC protein has been detected in malignant cells of a subset of breast cancers and their adjacent reactive endothelial and mesenchymal cells in which endogenous retinoblastoma protein (pRB) is overexpressed (FIG. 18).

Finally, in the context of in vivo host defense, the GrB-NIC gene products may cause apoptosis of aberrant/damaged cells, or induce death of cytotoxic lymphocytes and allograft cells. Therefore, expression of GrB-NIC can either positively or negatively affect the effectiveness of host immunity and might be causally related to autoimmune diseases and allograft rejection after, for instance, bone marrow, skin, renal, and other organ transplantation. In the latter scenarios, the requirement for CTL during allograft rejection is again controversial in the current literature. Most recent studies suggest that, in the absence of $CD8^+$ T cells, an alternative mechanism associated with GrB expression can mediate apoptosis and liver graft rejection (Ogura et al., 2001).

In non-immune cells, up-regulation of GrB-NIC has the same biological consequences as acquiring exogenous GrB from cytotoxic lymphocytes. Overexpression of ectopic pRB in $RB^{-/-}$ tumor cells results in differentiation and endogenous GrB-NIC expression, while presence of ectopic pRB in these tumor cells prevents GrB-NIC-mediated apoptosis. Of note, differentiating $RB^{-/-}$ cells, at least in restricted cell lineages, also produce GrB-NIC. For example, by functionally ablating the pRb family, the RA-treated, differentiating P19 neuronal cells underwent massive apoptosis that is associated with expression of GrB-NIC. p53 can induce GrB-NIC in Saos-2 in the absence of pRB, leading to rapid apoptosis of the GrB-NIC-producing tumor cells (FIG. 7). Lymphocyte GrB reportedly induces apoptosis through a Bcl-2-inhibitable mitochondrial cytochrome c release pathway, and Bcl-xL mutant mice die in mid-gestation with extensive apoptotic cell death in postmitotic immature neurons, similar to that seen in $RB^{-/-}$ mice. Both p53 and E2F-1 are upstream activators of GrB (GrB-NIC), and loss of p53 or E2F-1 gene function prevents CNS neuron cell death in RB mutant mice. Therefore, abundant data suggests that the newly discovered GrB-NIC provides an intriguing solution to the long-standing puzzle of massive neuronal cell death in mice with a homozygous RB gene mutation. The information disclosed herein indicates that differentiating and differentiated neuronal cells physiologically express both GrB-NIC and high level of pRB; the high level of pRB protects neuronal cells, but not the neighboring dividing neural precursor cells (which have a low level of pRB soon after metaphase) from GrB-NIC-mediated apoptosis. Programmed cell death (apoptosis) is a prominent feature of the developing nervous systems, which provides a simple way for eliminating "out-of-date" or misplaced cells, for regulating total nerve cell numbers and, perhaps, for selecting the most competitive, fittest neuron cells. In RB mutant mice, GrB-NIC expression leads to the execution of apoptosis of all neuronal cells. With the unexpected discovery of GrB-NIC, we might once again have to shift our thinking towards pRB's non-redundant role in protecting differentiating neural cells (and perhaps also other restricted cell lineages) from destruction by their own GrB-NIC.

The following general background information and protocols are provided to further support the disclosure and embodiments of the invention disclosed and particularly contemplated by the inventors.

Nucleic Acid Detection

The disclosed nucleic acid sequences facilitate the detection of complementary sequences in vivo and in vitro. For example, the disclosed sequences have utility as probes or primers in a variety of assays.

Hybridization

The use of a hybridization probe of between 10 and 100 nucleotides in length, or in some aspect of the invention even up to 1–2 kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be utilized in protocols to selectively form duplex molecules with complementary stretches of DNA, genes or RNAs or to provide primers for amplification of DNA or RNA. Depending on the application envisioned, one will desire to employ varying conditions of hybridization to achieve varying degrees of selectivity of probe towards target sequence.

For applications requiring high selectivity, one of skill would typically employ relatively stringent conditions, e.g., by selecting relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that stringency may be further increased through the addition of increasing amounts of formamide.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label. Exemplary techniques include Northern and Southern blotting.

"Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane supports for analysis with a radiolabeled, biotinylated or enzyme-labeled probe as described in sections 9.37–9.52 of Sambrook et al , supra.

"Northern analysis" is a method used to identify RNA sequences that hybridize to a known probe such as all oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

One of skill would further be aware of the variety of hybridization based technologies developed for the detection, amplification and/or isolation of target nucleic acids. Specifically contemplated by the present inventors are chip-based DNA technologies such as those described by Hacia et al., 1996 and Shoemaker et al., 1996. These techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization, Pease et al., 1994; Fodor et al., 1991.

Amplification

The disclosed nucleic acid sequences facilitate the amplification of GrB-NIC sequences in vivo and in vitro. For example, the disclosed sequences have utility in the construction of primers useful in the amplification or detection of a GrB-NIC construct.

Nucleic acids may be amplified using a variety of techniques standard in the art. In general, such techniques require the hybridization of a priming or initiating sequence to the nucleic acid sample to be amplified. In an exemplary embodiment, primers that selectively hybridize GRB-NIC genes sequences are contacted with a nucleic acid sample under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Nucleic acid may be roughly quantitated by detection of the amplified product. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A variety of other amplification procedures may be equally applicable. One of ordinary skill would be aware of such techniques, including but not limited to: the ligase chain reaction ("LCR"), disclosed in :EPA No. 320 308, incorporated herein by reference; Qbeta Replicase, described in PCT Application No. PCT/US87/00880, incorporated herein by reference; Strand Displacement Amplification (SDA); Repair Chain Reaction (RCR); transcription-based amplification systems (TAS), including nucleic acid sequence based amplification (NASBA) and 3SR (Gingeras et al., PCT Application WO 88/10315, incorporated herein by reference).

Other Assays

It is contemplated that alterations or mutations in the GrB-NIC gene in non-immune cells may have a broad range of implications. Thus, detections of alterations in the GrB-NIC gene in such cells is expressly contemplated. Methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above), single-strand conformation polymorphism analysis ("SSCP") as well as a variety of microarray based methodologies.

A number of methods of screening for point mutations are based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

Antisense

The modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA.

In general, an antisense compound refers to any RNA or DNA molecule which can bind specifically with a targeted polynucleotide sequence, thereby modulating the function of the targeted sequence. As used herein, the term "target nucleic acid" encompasses DNA encoding GrB-NIC, RNA (including pre-mRNA and mRNA) transcribed from such DNA, and also cDNA derived from such RNA. Antisense oligonucleotides of the present invention include nucleic acids of a variety of lengths from oligonucleotides to the length of the entire GrB-NIC mRNA, as well as up to and including the length of the GrB gene or longer if necessary.

"Targeting" an antisense compound to a particular nucleic acid, in the context of this invention, is a multistep process. The process usually begins with the identification of a sequence within the targeted nucleic acid, the blocking of which modulates function. This may be, for example, a start site, a promoter or enhancer sequence. Once determined, a construct complementary to this region is constructed.

Antisense compounds are commonly used as research reagents and diagnostics. For example, antisense oligonucleotides, which are able to inhibit gene expression with exacting precision, are used by those of ordinary skill to elucidate the function of particular genes. Antisense compounds are also used, for example, to distinguish between functions of various members of a biological pathway. It is thus specifically contemplated that antisense compounds incorporating the sequences of the invention may be harnessed for research use.

The specificity and sensitivity of antisense is also employed by those of skill in therapeutic applications. Antisense oligonucleotides have been employed as therapeutic moieties in the treatment of a variety of disease states in both animals and man. Antisense oligonucleotides have been safely and effectively administered to humans and numerous clinical trials are presently underway. One of skill would thus be aware of useful therapeutic modalities that can be configured in regimes for the treatment of animals and especially humans at the cellular, tissue organ, system or organismal level.

One of ordinary skill would be aware of methods and techniques for the formulation of antisense compounds. Such methods are readily known to those of skill in the art. Specific examples of such teaching is provided in the following patents, which are expressly incorporated herein by reference: U.S. Pat. Nos. 5,276,019, 5,563,255 6,365, 354, and 6,294,664.

The antisense compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention may further be formulated as a pharmaceutical compositions and formulations for administration. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Recombinant Vectors, Host Cells and Expression

The instant invention encompasses the insertion of GrB-NIC into vectors or constructs, the transformation of cells with such vectors and, in some circumstances, the expression of protein by these cells. The term "expression vector or construct" refers to any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein, polypeptide or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with an GrB-NIC gene, as included in the 5' non-coding sequences located upstream of the coding segment or exon. In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a GrB-NIC gene in its natural environment. Such promoters may include promoters normally associated with other genes, and/or promoters isolated from any other bacterial, viral, eukaryotic, or mammalian cell, and/or promoters made by the hand of man that are not "naturally occurring," i.e., containing difference elements from different promoters, or mutations that increase, decrease, or alter expression.

Understandably, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al.(1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

The use of viral, mammalian or bacterial promoters which are well-known in the art to achieve expression are contemplated as well, provided that the levels of expression are sufficient for a given purpose. Tables 1 and 2 below list several elements/promoters which may be employed, in the context of the present invention, to regulate the expression of a GrB-NIC gene. This list is not intended to be exhaustive of all the possible elements involved in the promotion of expression but, merely, to be exemplary thereof.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

Promoter and Enhancer Elements

| Promoter/Enhancer | References |
| --- | --- |
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α1-Antitrypain | Latimer et al., 1990 |
| H2B (TH2B) Histone | Hwang et al., 1990 |

TABLE 1-continued

Promoter and Enhancer Elements

| Promoter/Enhancer | References |
|---|---|
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotten 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1a | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Riffling et al., 1989 |
| MHC Class I Gene H-2 κb | Interferon | Blanar et al., 1989 |
| HSP70 | E1a, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal are convenient and known to function well in various target cells. Also contemplated as an element of the expression cassette is a terminator. These elements serve to enhance message levels and to minimize read through from the cassette into other sequences.

A specific initiation signal is generally required for efficient translation of coding sequences. These signals include the ATG initiation codon and adjacent sequences. Exogenous translational control signals, including the ATG initiation codon, may need to be provided. The presence or absence of such sites would be readily apparent to one of ordinary skill in the art, and the necessary signal may be readily engineered if necessary. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that GrB-NIC proteins, polypeptides or peptides may be co-expressed with other selected proteins, wherein the proteins may be co-expressed in the same cell or a GrB-NIC gene may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both the GrB-NIC and the other selected protein in the same recombinant cell.

As used herein, the terms "engineered" and "recombinant" cells or host cells are intended to refer to a cell into which an exogenous DNA segment or gene, such as a cDNA or gene encoding a GrB-NIC protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant GrB-NIC protein, polypeptide or peptide, whether mutant or wild-type, in accordance with the present invention one would prepare an expression vector that comprises a wild-type, or mutant GrB-NIC protein-encoding nucleic acid under the control of one or more promoters. To bring a coding sequence "under the control of a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

For long-term, high-yield production of a recombinant GrB-NIC protein, polypeptide or peptide, stable expression is preferred. For example, cell lines that stably express constructs encoding a GrB-NIC protein, polypeptide or peptide may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk-, hgprt- or aprt-cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. Such large scale production techniques would be well within the purview of one of ordinary skill.

Polypeptides

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof The polypeptides of the invention include full length proteins encoded by the nucleic acid sequences set forth above. Particularly preferred polypeptides comprise the amino acid sequence of SEQ ID NO: 3 with particularly preferred fragments comprising amino acid sequence of SEQ ID NO: 3 containing an internal deletion of the activation dipeptide $Gly_{53}$–$Glu_{54}$.

The polypeptide of SEQ ID NO: 3 includes an N-terminal hydrophobic region that functions as a signal peptide, followed by an activation dipeptide. Computer analysis predicts that the signal peptide corresponds to residues 1 to 52 of SEQ ID NO: 3, with a consensus cleavage site for signal peptidase following residue 52. A dual proteolytic processing pathway is implied for the maturation of biologically active enzyme. Cleavage of the signal peptide thus would yield an inactive proenzyme having an amino-terminal $Gly_{53}$–$Glu_{54}$ activation dipeptide, which must be removed to generate a mature protease comprising amino acids 55 through 281 of SEQ ID NO: 3. The skilled artisan will recognize that the above-described boundaries of such regions of the polypeptide are approximate. The polypeptides of the invention generally will be found intracellularly prior to processing, although the post-translationally modified product may be secreted.

Antibody Generation

In certain embodiments, the present invention provides antibodies that bind with high specificity to GrB-NIC polypeptides and peptides provided herein. Thus, antibodies that bind to the protein products of the isolated nucleic acid sequences of SEQ ID NO: 2 or the amino acid sequence of SEQ ID NO: 3 are provided. As detailed above, in addition to antibodies generated against the full length proteins, antibodies may also be generated in response to smaller constructs comprising epitopic core regions, including wild-type and mutant epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

Nevertheless, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The term "antibody" is used to refer to any antibody-like molecule that has an antigen binding region, and includes antibody fragments such as Fab', Fab, F(ab')2, single domain antibodies (DABS), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic GrB-NIC protein composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified GrB-NIC protein, polypeptide, peptide or domain, be it a wild-type or mutant composition. The immunizing composition is administered in a manner effective to stimulate antibody producing cells.

The methods for generating MAbs generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-wk intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1. Ag 4 1, Sp210-Ag14, FO, NSO/U, MPC-11, MPC11-X45-GTG 1.7 and S194/5XX0 Bul; for rats, one may use R210. RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two wk. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is further contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in E. coli.

Antibody Conjugates

The present invention further provides antibodies against GrB proteins, polypeptides or peptides, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody, conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins". In the context of the present invention, immunotoxins are generally less preferred.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

Immunodetection Methods

In still further embodiments, the present invention concerns immunodetection methods for binding, purifying, removing, quantifying or otherwise generally detecting GrB-NIC protein components. The GrB-NIC antibodies prepared in accordance with the present invention may be employed to detect wild-type or mutant GrB-NIC proteins, polypeptides or peptides. As described throughout the present application, the use of wild-type or mutant GrB-NIC specific antibodies is contemplated. The steps of various useful immunodetection methods have been described in the scientific literature, such as, e.g., Nakamura et al. (1987), incorporated herein by reference. Exemplary immunodetection methods are well known to those of ordinary skill, and would include, for example. RIA, EIA, ELISA, ELISPOT, as well as a variety of immunohistochemical techniques.

In general, the immunobinding methods include obtaining a sample suspected of containing an GrB-NIC protein, polypeptide or peptide, and contacting the sample with a first anti-GrB-NIC antibody in accordance with the present invention, as the case may be, under conditions effective to allow the formation of immunocomplexes.

These methods include methods for purifying wild-type or mutant GrB-NIC proteins, polypeptides or peptides as may be employed in purifying wild-type or mutant GrB-NIC proteins, polypeptides or peptides from patients' samples or for purifying recombinantly expressed wild-type or mutant GrB-NIC proteins, polypeptides or peptides. In these instances, the antibody removes the antigenic wild-type or mutant GrB-NIC protein, polypeptide or peptide component from a sample. The antibody will preferably be linked to a solid support, such as in the form of a column matrix, and the sample suspected of containing the wild-type or mutant GrB-NIC protein antigenic component will be applied to the immobilized antibody. The unwanted components will be washed from the column, leaving the antigen immunocomplexed to the immobilized antibody, which wild-type or mutant GrB-NIC protein antigen is then collected by removing the wild-type or mutant GrB-NIC protein, polypeptide or peptide from the column.

The immunobinding methods also include methods for detecting or quantifying the amount of a wild-type or mutant GrB-NIC protein reactive component in a sample, which methods require the detection or quantification of any immune complexes formed during the binding process. Here, one would obtain a sample suspected of containing a wild-type or mutant GrB-NIC protein, polypeptide or peptide, and contact the sample with an antibody against wild-type or mutant GrB-NIC, and then detect or quantify the amount of immune complexes formed under the specific conditions.

In terms of antigen detection, the biological sample analyzed may be any sample that is suspected of containing a wild-type or mutant GrB-NIC protein-specific antigen. Contacting the chosen biological sample with the antibody under conditions effective and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any GrB-NIC protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological or enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The GrB-NIC antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Immunohistochemistry

The antibodies of the present invention may also be used in conjunction with both fresh-frozen and formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

In Vivo Delivery and Treatment Protocols

It is expressly contemplated that the disclosed sequences may be incorporated into vectors as a gene replacement or a gene-based therapeutic. Exemplary delivery protocols would be known to one of skill. Exemplary protocols are briefly discussed below.

Adenovirus

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesize.

The expression vector comprises a genetically engineered form of adenovirus. Knowledge of the genetic organization or adenovirus, a 36 kB, linear, double-strained DNA virus, allows substitution of large pieces of adenoviral DNA with foreign sequences up to 7 kB (Grunhaus and Horwitz, 1992). In contrast to retrovirus, the infection of adenovira DNA in host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E213) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m.u. is particularly efficient during the late phase of infection, and all the mRNA's issued from this promoter possess a 5'-tripartite leader (TL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system in is an alternative approach for the production of recombinant adenovirus.

Generation and propagation of the current adenovirus vectors, which are replication deficient, depend on a unique helper cell line, designated 293, which was transformed from human embryonic kidney cells by Ads DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) discloses improved methods for culturing 293 cells and propagating adenovirus. In one format, natural cell aggregates are grown by inoculating individual cells into 1 L siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1 coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adendovirus have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

One limitation to the use of retrovirus vectors in vivo is the limited ability to produce retroviral vector titers greater than 106 infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions (Warner and Heston, 1991). (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

Other Viral Vectors Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Change et al., 1991).

Non-viral Vectors

In order to effect expression of sense or antisense gene constructs, the expression construct must be delivered into a cell. This delivery may be accomplished in vitro, as in laboratory procedures for transforming cells lines, or in vivo or ex vivo (see below), as in the treatment of certain disease states. As described above, the preferred mechanism for delivery is via viral infection where the expression construct is encapsidated in an infectious viral particle. Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yand et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer permeabilize the cell membrane. This is particularly applicable for transfer in vitro but it may be applied to in vivo use as well. Dubensky et al. (1984) successfully injected polyomavirus DNA in the form of CaPO4 precipitates into liver and spleen of adult and newborn mice demonstrating active viral replication and acute infection. Benvenisty and Neshif (1986) also demonstrated that direct intraperitoneal injection of CaPO4 precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cellleukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Stem Cell Technology and Cell Replacement Therapy

It is expressly contemplated that the methods and compositions of the disclosed invention will be applicable in the related fields of cell replacement therapy and stem cell technology. The recognized apoptotic properties of GrB-NIC are considered to be of particular relevance in the development and differentiation of stem cells. The modulation of GrB-NIC expression in stem cells allows for the maintenance of the potency of stem cells in culture and further promotes the survival of both the progenitor and differentiated descendants of stem cell lines.

A stem cell is an undifferentiated cell capable of propagation either in vivo or ex vivo and capable of differentiating into other cell types. In general, stem cells are capable of differentiation into certain differentiated, committed, immature, progenitor, precursor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. Stem cells considered totipotent can, in response to the appropriate stimuli or differentiation factor(s) differentiate into any tissue in the body. Stem cells considered pluripotent, can, in response to the appropriate stimuli or differentiation factor(s) differentiate into many different cell types, but not all the cells of an organism. One of ordinary skill would be aware of the differentiation factors that promote the development of alternate cell lineages from stem cell lines. When a stem cell differentiates it generally gives rise to a more adult cell type, which may be a partially differentiated cell such as a progenitor cell, a differentiated cell, or a terminally differentiated cell.

In general, stem cells are self-renewing, multipotent and able to differentiate, whereas "progenitor" or "precursor" cells refer to undifferentiated cells whose lineal descendants differentiate along the appropriate pathway to produce a fully differentiated phenotype (i.e., cells with a restricted lineage). For example, neural stem cells isolated from the hippocampus (HC) or the subventricular zone, are self renewing and able to generate, in vitro, multiple types of cells including neurons, glia and even hematopoetic cells.

Stem cells are propagated in vivo or in vitro, and in the absence of the proper stimuli, generally retain an undifferentiated state. In response to the proper stimuli or cues, the propagating stem cells will differentiate, losing potency and eventually terminally differentiating into a adult or mature cell type. In the course of differentiation, the number of terminally differentiated cells is not commensurate with the expected yield. Losses are considered to be due to a portion of the differentiating cells undergoing apoptotic cell death.

The use of stem cells in cell replacement applications has incredible therapeutic potential. Stem cells are useful in a variety of therapeutic modalities, including, for example: (1) cell replacement for regenerating the hematopoietic system of a host deficient in any class of hematopoietic cells; (2) cell replacement in a host with diseased, injured or damaged tissue or organ that is amenable to re-engraftment of stem cells or their progeny; (3) producing target cells for gene therapy. One of ordinary skill would be well aware of the many techniques of utilizing stem cells in the variety of cell replacement therapies now practiced or being developed. Examples of those technologies underlying stem cell technology and cell replacement techniques are described in a variety of publications well known to one of skill, including the following patents and publications, which are herein expressly incorporated by reference: U.S. Pat. Nos. 5,843,780, 5,922,597, 5,681,559, 6,334,872, 5,958,767, 5,914,108, 5,643,741; U.S. patent application Ser. No. 20,020,004,241; Kennea, et al. 2002, Wobus, et al. 2001, Pera, 2001, Odorico, et al. 2001, Zandstra, et al. 2001, Romano et al. 2000, and Weissman, 2000.

The use of pluripotent stem cells or lineage committed progenitor cells derived from stem cells circumvents many of the problems that arise from the transfer of mature cells. Methods of the present invention enhance the culture of stem cells and the production of cells derived from stem cells for cell replacement therapies. Cell replacement therapy involves the reintroduction or engraftment of cells that integrate into damaged, diseased or injured structures after transplantation. The replacement of cells may be targeted to specific, anatomically circumscribed regions of organ or tissue, or also, if desired, to larger areas of the an organ or tissue, up to and including the potential full replacement of a damaged or diseased structure. One of ordinary skill would be aware of the variety of applications of cell replacement therapy. For example, cells produced utilizing the method of the invention can be transferred into a host with the proper stimuli to induce the cells to develop into and replace disease, damaged or injured cells or tissue. Cells produced utilizing the method of the invention may also be grown ex vivo or in vitro under the proper stimuli to produce cells or tissue which may be directly engrafted into a recipient as a replacement for damaged or diseased organs or tissue. The cells subjected to transferring may be derived from a cell population obtained from the patient who will be infused with the cells to be transferred. Alternatively, the cells to be transfected may be derived from a cell population obtained from a suitable MHC-compatible donor or the cells may be rendered non-immunogenic.

Methods of the present invention may enhance target cell production for gene therapy protocols. Gene therapy, or the transfer of exogenous DNA into human cells, can be used to correct or ameliorate a variety of clinical conditions. Although originally developed for the treatment of inherited diseases including those of improper globin expression, certain enzyme deficiencies and auto-immune disorders, gene therapy now encompasses a wide variety of potential uses including in the treatment of infectious disease such as HIV and in cancer therapy. For example, cells produced utilizing the method of the invention can be transfected with transcribable genetic material encoding one or more protein products important to health or survival. Alternately or additionally, cells produced by the method of the invention can be transfected with transcribable genetic material encoding an anti-sense RNA capable of inhibiting the expression of an undesirable product which would otherwise be produced. Transfected cells may be infused into suitable subjects to treat or alleviate the symptoms of a pathological condition. The cells subjected to transfection may be derived from a cell population obtained from the patient who will be infused with the transfected cells. Alternatively, the cells to be transfected may be derived from a cell population obtained from a suitable MHC-compatible donor. In addition to gene therapy protocols, gene transfer into erythroid cells may be used to introduce genes coding for transcription or other factors to increase the production of hemoglobin or other erythroid-specific proteins. Gene transfer may also be used to introduce genes for growth factor receptors that have been mutated to render them either hypersensitive or constitutively active in order to reduce or alleviate the need for growth factors. Further, gene transfer can be used to introduce genes coding for proteins capable of immortalizing erythroid cells thus creating permanent cell lines.

Pharmaceutical Compositions

Where clinical applications are contemplated, it will be necessary to prepare a pharmaceutical compositions—either gene delivery vectors or engineered cells—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors and cells of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Screening for Modulators

The nucleic acid, protein and peptide compositions of GrB-NIC may be utilized in order to elucidate molecules that modulate the function, expression, transcription or effects of GrB-NIC. As used herein the term "candidate modulator" refers to any molecule that may potentially effect, inhibit or enhance GrB-NIC activity. The candidate substance may be a protein or fragment thereof, an antibody, an enzyme, a small molecule, a nucleic acid molecule or other biomolecules. Using lead compounds to help develop improved compounds is know as "rational drug design" and includes not only comparisons with know inhibitors and activators, but predictions relating to the structure of target molecules.

One goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Alternatively, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, nucleic acid, polysaccharide, small molecule or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on GrB-NIC.

In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

In Cyto Assays

The present invention also contemplates the screening of compounds for their ability to modulate GrB-NIC in cells. Various cell lines can be utilized for such screening assays, including cells specifically engineered for this purpose. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

EXAMPLES

The following examples are included to demonstrate preferred embodiments of the present disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Molecular Cloning of Inducible Granzyme B Gene in Human Non-hematopoietic Tumor Cells By using a panel of cell lines in which expression of the wild-type pRB is tightly controlled by tetracycline (Tc) (Xu et al, 1997), the active and inactive genes in Saos-2 osteosarcoma and MDA-MB-468 breast carcinoma cell lines after reexpression of pRB were examined. The peak levels of ectopic pRB expression in these cells are comparable to those observed in tumor cells overexpressing pRB in vivo (Xu, 1995). An approach involving differential display polymerase chain reaction (DD-PCR) and cDNA microarray assay was applied to identifying genes whose transcription is activated in the tumor cells upon pRB-induced growth arrest. Unexpectedly, one of the cloned cDNAs predicts a protease that shares complete amino acid identity with the human CTL/NK cell-specific GrB zymogen but is 34 amino acids longer at the amino terminus (FIG. 1). This heretofore unidentified and unisolated peptide was designated granzyme B in non-immune cells (GrB-NIC). The 5'-coding sequence of GrB-NIC cDNA extends into the proximal promoter region of lymphocyte GrB where the putative TATA box, NF-AT (nuclear factor of activated T cells)-binding site, and major transcription initiation site are located (Klein et al, 1989; McCaffrey et al, 1993) (FIG. 1). Both ribonuclease protection assay (RPA) and Northern blot analysis demonstrate that the GrB-NIC mRNA levels increase up to 17-fold in pRB-expressing Saos-2 and MDA-MB-468 tumor cells (FIG. 2A, B). The Northern blotting results establish that the GrB-NIC mRNA detected in these solid tumor cells is indeed larger than the GrB mRNA from IL-2-stimulated peripheral blood leukocytes (PBL) (FIG. 2B). The difference in transcript sizes of GrB-NIC and GrB is consistent with their respective cDNA lengths (951 bp for GrB-NIC versus 848 bp for GrB).

Example 2

Mature Endogenous GrB-NIC Protease is Essentially Identical to Lymphocyte GrB and Enzymatically Active Expression of GrB-NIC in Saos-2 and MDA-MB-468 tumor cells during pRB-induced growth arrest was further studied at the protein level by immunochemical staining and Western immunoblotting. As detected by immunostaining using anti-GrB antibodies (FIG. 3A), GrB-NIC is located both in cytoplasm and in nuclei (mainly in nucleoli); a comparable pattern is observed for GrB from IL-2-activated PBL (Trapani et al., 1996). Confocal laser scanning microscopy (CLSM) images obtained by double immunofluorescence staining of pRB and GrB-NIC reveals that the GrB-NIC protein accumulates in the pRB$^+$ (in Tc-free medium), but not in the pRB$^-$ (in medium containing Tc) Saos-2 and MDA-MB-468 tumor cells (FIG. 3A, inserts in panels a-d). Western blotting demonstrates GrB-NIC protein triplets from the growth-arrested Saos-2 and MDA-MB-468 tumor cells with apparent molecular masses ($M_r$) of 26, 33, and 39 kDa (FIG. 3B). By SDS-PAGE, the 33-kDa GrB-NIC protein band is identical to the mature glycosylated GrB protein from human PBL. The 39-kDa protein markedly increases in the tumor cells after reexpression of pRB. An in vitro hydrolysis assay using endoglycosidase H (Endo H) reveals that, after deglycosylation, the 39-kDa GrB-NIC and the 33-kDa lymphocyte GrB are identical to each other with a reduced apparent Mr of 26 kDa (FIG. 3C). Human GrB cDNA of CTL/NK origins contains a single open reading frame encoding a preproenzyme of 247 amino acids. The predicted mature GrB is an active enzyme of 227 amino acids (after N-terminal cleavage by signal peptidase and dipeptidyl peptidase I [DPPI]) with an unglycosylated $M_r$ of 26 kDa (Trapani et al., 1996). Marked differences in apparent Mr of the mature GrB, however, have been reported in the literature, ranging from 26 to 67 kDa, which are usually interpreted as being due to heterogeneous N-linked glycosylation. Both glycosylated and nonglycosylated mature GrB are proteolytically active (Trapani et al., 1996; Pinkoski et al., 2000).

Lymphocyte GrB is a highly regulated signaling molecule that controls target cell apoptosis by cleaving key cellular proteins solely after aspartate residues. Its primary specificity for Asp turns out to be very rare among proteases. An in vitro Asp-ase assay (Smyth et al., 1995) was performed to study the enzymatic activity of GrB-NIC extracted from the pRB-reexpressing Saos-2 cells. The assay was done by using immunopurified GrB-NIC with a synthetic thiobenzyl ester peptide as the substrate (FIG. 3D) and showed that Asp-ase activity of GrB-NIC in Saos-2 pRB-clone 11 peaked after the cells were grown in Tc-free medium (pRB$^+$) for 9–12 days (FIG. 3D)

This GrB-NIC-associated proteolytic activity was further confirmed by the specificity of the immune complexes. To this end, an expression plasmid driven by the human cytomegalovirus (CMV) promoter/enhancer was constructed containing the GrB-NIC cDNA, designated pCMV.GrB-NIC. By using the same antibodies, strong positive immunoreactivity was detected in COS-7 cells transfected with pCMV.GrB-NIC, but not in parental cells (FIG. 3A, panels f, g; FIG. 19). It was also determined by studies conducted in parallel that COS-7 cells transfected with CMV promoter-driven expression plasmids containing the wild-type GrB-NIC cDNA (pCMV.GrB-NIC), or a mutated version, in which the second AUG codon (corresponding to the first AUG codon of GrB mRNA) was substituted with UUC (Phe) (pCMV.2$^{nd}$Met |Phe), or the wild-type GrB cDNA (pCMV.GrB), all produced immunoreactive proteins of the same size (FIG. 19). The results provided clear evidence that the first AUG codon of the GrB-NIC open reading frame can be used as an authentic translation initiation site in vivo, and post-translational processing of GrB-NIC and GrB preproenzyme in COS-7 cells efficiently removed their amino-terminal signal peptides (Smyth et al., 1995).

Example 3

Accumulation of Endogenous GrB in Non-immune Cells is Accompanied by Site-specific Cleavage of Dephosphorylated pRB and Post-growth-arrest Apoptosis The RB protein status in the RB-reconstituted Saos-2 cells was evaluated by Western blotting. As shown in FIG. 5A, site-specific proteolytic cleavages of pRB occur in the Tc-regulated, RB-reconstituted tumor cell lines. After the tumor cells had been grown in Tc-free medium for 4 or more days, pRB was completely dephosphorylated (FIG. 5A, lane 2). An interior RB protein cleavage fragment of ~42 kDa (pRB42) (An and Dou, 1996) was detected following re-addition of Tc (0.5 µg/ml) to the medium to switch off expression of pRB (FIG. 5A, lane 3). Moreover, both the pRB42 and a C-terminal cleavage segment of pRB (pRB) that is roughly 5 kDa smaller than the full-length pRB (Tan et al., 1997; Chen et al., 1997) were observed when the growth-arrested tumor cells were subsequently cultured in medium with low Tc concentrations (0.01–0.05 µg/ml) (FIG. 5A, lanes 4, 5). It appears that under the latter condition, the Tc-responsible promoter activity was restricted to a threshold level (about an order of magnitude lower than in Tc-free medium), when pRB degradation exceeded output, resulting in accumulation of specific cleavage fragments of pRB. The C-terminal cleavage of pRB, in this case, occurred prior to the interior cleavage (compare FIG. 5A, lanes 4 and 5).

Next, a panel of assays, including DNA fragmentation, terminal deoxynucleotidyl transferase-mediated dUTP nick-end labeling (TUNEL), $^3$H-thymidine incorporation, immunocytochemical staining, and altered morphology, was applied to the RB-reconstituted Saos-2 cells after withdrawal (by re-addition of 0.5 µg/ml Tc to the culture medium) or reduction (by growing the cells in medium containing 0.01–0.05 µg/ml Tc) of pRB expression. It was found that massive cell death, which occurred concurrently with the proteolytic cleavage of pRB (FIG. 5A), was marked by DNA fragmentation (FIG. 5B), $^3$H-thymidine-labeled, strikingly deformed nuclei and positive TUNEL (FIG. 5C, panels b, c & d). These characteristics are consistent with apoptosis. The $^3$H-thymidine incorporation into the deformed nuclei was a sign of impaired cell-cycle reentry (FIG. 5C, panels b & c). It seems that the viability of tumor cells with accumulation of GrB-NIC was stringently dependent on continuing overexpression of the functional pRB as well as maintaining its integrity. In this context, several groups have reported that as cells are induced to apoptosis upon treatment with a wide variety of death inducers, the RB protein is dephosphorylated, and then cleaved at its C-terminal and/or interior putative consensus sites by a caspase-like activity (An and Dou, 1996; Tan et al., 1997; Chen et al., 1997; Fattman et al., 1998).

Example 4

GrB-NIC-Associated Rapid Apoptosis of Bystander pRB$^-$ Tumor Cells

Cytotoxic lymphocytes cause target cell apoptosis by exocytosis of cytoplasmic granules containing GrB and other cytolytic proteins. Therefore, to further identify the similarities in biological functions of GrB-NIC and lymphocyte GrB, whether GrB-NIC produced by the RB-reconstituted tumor cells had a paracrine effect on their pRB$^-$ neighbors that did not express GrB-NIC was investigated. The studies were carried out by co-cultivating the Tc-regulated, RB-reconstituted Saos-2 and MDA-MB-468 clone cells with their respective parental cell lines in a 2:1 ratio of pRB$^+$ to pRB$^-$ cells. By immunocytochemical staining of pRB and microscopic analysis, it was striking that numerous pRB$^-$ parental tumor cells died in the mixed cultures between Days 3 and 5, while most pRB$^+$ clone cells remained morphologically viable (FIGS. 4A–4F). The presence of large numbers of condensed subnuclear bodies (FIGS. 4C & F) suggested that the bystander killing of unmodified pRB$^-$ parental cells in the mixed cultures was a consequence of apoptosis. Of particular interest were the results of double immunofluorescence staining of pRB and GrB-NIC. The images obtained by CLSM clearly showed that some pRB$^-$ tumor cells in the mixed cultures that were originally GrB-NIC negative (see FIG. 3A above) acquired positive GrB-NIC staining prior to the onset of the bystander cell death (FIGS. 4B & E, inserts). Dual-parameter fluorescence-activated cell sorting (FACS) indicated that the pRB$^+$ Saos-2 cells were mostly arrested in G1 phase as expected; the pRB$^-$ parent cells in the mixed culture, which were not arrested in G1 phase, had a much larger sub-G1 fraction of apoptotic cells than the pRB$^+$ cells (17.5% versus 2.4% of the total gated events) (FIGS. 4G–4L). The FACS profiles are consistent with the microscopic examination. It appears that GrB-NIC secreted from the pRB$^+$ cells can be endocytosed by other pRB$^+$ cells, as well as pRB$^-$ cells in the case of mixed culture. In the latter case, apoptosis of the GrB-NIC-sensitive pRB$^-$ cells occurred first; the pRB$^+$ tumor cells would not die until their dephosphorylated pRB was mostly degraded (see FIG. 5). The data imply that GrB-NIC produced in non-immune cells can mediate bystander apoptosis via an exocytosis/endocytosis mechanism, which is similar to its lymphocyte counterpart GrB. The many biochemical and biological similarities between GrB-NIC and GrB support the view that in non-immune cells, up-regulation of endogenous GrB-NIC has the same biological consequences as acquiring exogenous GrB from cytotoxic lymphocytes.

Example 5

Localization of the GrB-NIC Promoter and its Essential Elements for Transcription Northern blot analysis indicates that the GrB-NIC mRNA is larger than the lymphocyte GrB mRNA, reflecting that it uses alternative promoter and upstream major transcription start site(s). To define the promoter region responsible for GrB-NIC transcription, the 5'-flanking sequence from human non-immune cells was cloned. Primers were designed on the basis of a partial sequence obtained from the genome database for human chromosome 14q11 corresponding to the 5'-flanking region of GrB locus (*Homo sapiens* genomic contig sequences, Hs14_10219). PCR amplification was performed on TaqI genomic DNA fragment pools prepared from the Saos-2 cells. The authenticity of the cloned fragment was confirmed by sequence analysis. The nucleotide sequence of the GrB-NIC 5'-flanking region is shown in FIG. 1 with minor revisions from previously published genomic sequence data. Three oligonucleotide primers complementary to disparate 5' coding and noncoding sequences were used for primer extension assays in an attempt to locate the transcriptional start site(s) of GrB-NIC. Based on the results illustrated in FIG. 2C, two putative transcriptional start sites were mapped 146 and 179 bases, respectively, upstream from the first ATG codon of the GrB-NIC cDNA open reading frame. The DNA sequence surrounding the major start site (corresponding to the 46-nt major band shown in FIG. 6A) coincides with the consensus initiator context (Py$_2$CAPy$_4$, Py denotes pyrimidine), and is here assigned +1 as a reference point for base positioning in the genomic sequence. The 5'-flanking sequence immediately preceding the major start site is 61% GC-rich and is devoid of a typical TATA box at its characteristic position (although a sequence TAATAAAA resembling the TATA motif is found at –374/–368). The upstream region, however, contains consensus sequences for CCAAT boxes on both the antisense (–122/–118) and sense (–494/–490) strands. In comparison, the 208-bp downstream fragment +70/+277 (5'-proximal region of lymphocyte GrB, –148/+60 relative to the GrB transcription start site) contains the known major transcription initiation site in lymphocytes and a TATA-like sequence, as well as Ikaros, CRE, CBF/AP-1, and NF-AT binding sites, which are essential and sufficient for activation of GrB transcription in T lymphocytes after antigenic or mitogenic stimulation (Wargnier et al., 1995).

The transcriptional activities of the cloned GrB-NIC upstream sequences were examined in plasmid constructs. A DNA fragment spanning the 5'-flanking region from –863 to +70 (upstream of the lymphocyte GrB 5'-proximal promoter) was inserted in the sense orientation into the KpnI/SmaI sites of a promoterless vector, pCAT3, containing a bacterial chloramphenicol acetyltransferase (CAT) gene. The derived reporter plasmid construct was transfected into Saos-2 cells. A LacZ expression vector was also cotransfected to allow normalization for transfection efficiencies. Cell lysates of the transfectants had significantly higher CAT activity than lysates of the same cells transfected with the vector plasmid only (FIG. 2D), which suggested the presence of a functional promoter within the region. To further define the cis active DNA sequences that are required for transcription of GrB-NIC in non-immune cells, a series of 5' deletion mutants were also tested in the heterologous expression system with CAT as the reporter. The transient transfection results shown in FIG. 2D indicate that the sequence from –180 to +70 was sufficient to confer core promoter activity. Neither of the subfragments +15/+70 (FIG. 2D) or –180/+15 (data not shown) alone can effectively activate CAT transcription in Saos-2 cells. This suggests that the promoter activity of the sequence from –180 to +70 is the result of synergistic effect between cis elements existing in these two subfragments. For deletion mutants mapped between positions –551/–180, relatively stable levels of transcription were observed (FIG. 2D). Deleting the 5'-end sequence (–863/–551) of the cloned large promoter fragment, however, resulted in a threefold decrease in transcription activity (FIG. 2D), which suggests that enhancer-like elements might reside in this distal region. By reexamining the promoter sequence, it was determined that an additional AP-1 site and a reverse CCAAT box is located at positions –854 to –848 and –833 to –829, respectively (FIG. 1).

The sequence of the GrB-NIC 5'-flanking region as shown in FIG. 1 contains a potential E2F-like motif (TTGGCGG) at –121/–115, partially overlapping with one of the inverted CCAAT boxes at –121/–118. To test whether this E2F-like site can be recognized by E2F-1 transcription factor, an in vitro DNA electrophoretic mobility shift (EMS) assay was performed. The results shown in FIG. 9A indicated that the E2F-1 protein bound to a GrB-NIC 5'-flanking fragment containing the deduced E2F site. The formation of DNA-protein complex was apparently specific, since the labeled complex was abolished by adding cold probes, comprising the wild-type E2F recognition sequence but not a mutated one (compare FIG. 9A, lanes 2 & 3).

Given the specific binding of E2F-1 with the GrB-NIC promoter, and that the GrB-NIC gene was transcriptionally activated prior to pRB-mediated post-growth-arrest apoptosis, the steady-state levels of E2F-1 proteins over the same period was examined. The Western blotting results shown in FIG. 9B reveal that unphosphorylated (active) E2F-1 proteins accumulate in the RB-reconstituted Saos-2 and MDA-MB-468 tumor cells that overexpress pRB for prolonged periods. The phenomenon with respect to changes in the ratio of unphosphorylated to phosphorylated E2F-1 proteins in the RB-reconstituted cells is very significant, since virtually all phosphorylated E2F-1 protein disappears when the cells are in pRB$^+$ status for 5 to 12 days. This supports the notion that overexpression of pRB, while nearly completely inhibiting cyclin A/cdk2 (the upstream regulators of E2F-1 phosphorylation and DNA-binding activity), also protects E2F-1 from phosphorylation (inactivation) and subsequent degradation through the ubiquitin-proteasome pathway (Hofmann et al., 1996).

Example 6 wt-p53 Can Induce Endogenous GrB-NIC in the Absence of pRB, Resulting in Rapid Apoptosis of pRB Mutant Cells By using our improved Tc-regulatable gene expression system as illustrated in FIG. 16, we have also established stable tumor cell clones, in which expression of wt p53 can be turned on and off. The osteosarcoma cell line, Saos-2, was chosen as a model system, since it contains a complete deletion of p53 gene (p53null) and a defective (non-functional) RB gene (pRB−). The tight control of wt p53 expression in one of the representative Saos-2 p53 clones is demonstrated in FIG. 7 by p53 immunostaining. Expression of wt p53 in the tumor cells was almost completely abrogated (p53−) when there was as little as 0.1–0.5 µg/ml of Tc in the medium (FIG. 7, compare panels A and B). In this model, we found that reexpression of wt p53 in p53null/pRB− Saos-2 cells (that is, in Tc-free medium for less than 24 h) triggered rapid apoptosis, which is shown by numerous TUNEL-positive cells in FIG. 7, panel C. The apoptotic cell death was associated with transcriptional activation of the endogenous GrB gene (in the absence of functional pRB) (FIG. 7, panel D).

Example 7

Up-regulation of GrB-NIC in Non-immune cells: The Key is Differentiation

Reexpression of the RB gene in a diverse group of RB-defective tumor cells results in a stable irreversible growth arrest with phenotypes that are, by many generally accepted criteria, consistent with senescence (Xu et al., 1997). Senescent arrest resembles a process of terminal differentiation (Goldstein, 1990; Campisi, 1996). In RB-reconstituted Saos-2 osteosarcoma cells, induction of cell differentiation has been directly demonstrated by increased alkaline phosphatase activity and reduced expression of fibronectin (Ookawa et al., 1997). Similar to the case of Saos-2 cells, overexpression of pRB in RB-reconstituted MDA-MB-468 breast carcinoma cells led to a terminal differentiation phenotype, as evidenced by increased expression of the milk protein casein and accumulation of intra-cytoplasmic lipid droplets, both are biomarkers associated with breast cell differentiation (FIG. 8). The MDA-MB-468 pRB-clone cells in Tc-free medium are arrested in G1/G0 phase of the cell cycle, exhibiting mature cell morphology, characterized by lacy nuclei surround by sizeable cytoplasms. It appears that overexpression of pRB in RB$^{-/-}$ tumor cells of our models results in cell differentiation, endogenous GrB-NIC expression, and apoptosis of bystander pRB/AE (or low pRB) cells, while presence of ectopic pRB in these tumor cells prevents immediate cell death induced by their own GrB-NIC. Moreover, we have recently found that the parental pRB/AE MDA-MB-468 cells accumulate GrB-NIC following genistein (a chemo-preventive agent)-induced cell differentiation, which is linked to early-onset of apoptosis. Thus, differentiating MDA-MB-468 cells, either pRB$^+$ or pRB/AE, are able to produce GrB-NIC. Taken together, it appears that the key factor responsible for endogenous GrB-NIC expression in non-immune cells is cell differentiation, at least in restricted cell lineages.

To further validate the view that the key for up-regulation of GrB-NIC in non-immune cells is cell differentiation, the Tc-regulated, RB-reconstituted Saos-2 cells were stably transfected with a GrB-NIC promoter-luciferase reporter plasmid. Stable subclones in which the GrB-NIC promoter-luciferase construct was chromosomally integrated were selected with puromycin. These subclones were then pooled and used to assess the relevance of cell differentiation induced by overexpression of pRB and GrB-NIC promoter activation. Although marked growth arrest of the cell culture was observed within 24 hr of switching on pRb expression (in Tc-free medium), up-regulation of GrB-NIC promoter (as shown by increased luciferase activity up to 7-fold) (FIG. 20A) was not seen until 3–4 days after removal of Tc, consistent with the kinetics of pRb-induced endogenous GrB-NIC expression and cell differentiation.

Ascorbic acid (AA, reduced vitamin C) is essential for the formation of bone and necessary for the in vitro osteoblast differentiation. The use of a normal osteoblast cell line containing stably integrated GrB-NIC promoter-luc allowed a more detailed analysis of the relationship between activation of the transfected GrB-NIC promoter and osteoblast differentiation during a long-term (21-day) culture period (FIG. 20B). MC3T3-E1 cells, like other normal mouse osteoblast cells lines, are phenotypically heterogeneous (i.e. only a fraction of cells exhibit osteoblast characteristics). Therefore, to assess the regulation of GrB-NIC promoter during osteoblast differentiation, subclones of MC3T3-E1 preosteoblasts with high (subclone 4) and low (subclone 24) responsiveness to AA stimulation were used. Osteoblast differentiation was initiated after MC3T3-E1 subclone 4 (but not the AA-insensitive subclone 24) cells were cultured in the presence of 50 µg/mL AA for greater than 5 days. Both MC3T3-E1 subclone 4 and subclone 24 cells were transfected with GrB-NIC promoter-luciferase reporter plasmid. Stable tranfectants with integrated GrB-NIC promoter-luciferase construct were obtained by selection in AA-free α-MEM medium containing puromycin for 14 days. It was shown that in MC3T3-E1 subclone 4 cells with integrated GrB-NIC promoter, addition of AA (50 µg/mL ) into culture medium consistently stimulated luciferase reporter activity after 6–7 days. Luciferase activity continued to increase up to 8-fold at day 21. In contrast, AA failed to stimulate meaningful luciferase activity in stable tranfectants of MC3T3-E1 subclone 24, which was insensitive to AA-stimulation of osteoblast differentiation.

Example 8

Physiological Expression of GrB-NIC in Differentiating and Differentiated Neuronal Cells In Vitro and In Vivo Because the many biochemical and biological similarities between GrB-NIC and lymphocyte GrB, if GrB-NIC, or the homeostasis of GrB-NIC and pRB, is a physiological regulator of cell differentiation, it is likely to function by eliminating "out-of-date" or misplaced cells, by regulating total cell numbers and, perhaps, by selecting the most competitive, fittest cells during development (phylogenesis, morphogenesis, and histogenesis). This role would demand that GrB-NIC is expressed in the immune privileged sites, such as brain, to compensate for those functions usually performed by immune cells. The prediction has been supported by our recent studies on physiological expression of GrB-NIC in neuronal cells.

The P19 mouse teratocarcinomas stem cells have been used for analysis of early neuronal commitment and differentiation. When aggregated and exposed to 0.3 µM retinoic acid (RA), the P19 cells differentiate and develop large numbers of neurons and astrocytes cells with long processes become evident 2 days after the spheroids are plated onto the tissue culture dishes (FIG. 11A, panel b). These cells have been identified as cholinergic neurons of the central nervous system Expression of the GrB-NIC gene is activated during RA-induced neuronal differentiation of P19 pluripotent stem cells as determined by immunochemical staining (FIG. 11A, panel d) and Western blotting (FIG. 11B), but GrB-NIC was not readily detectable during DMSO-induced muscle differentiation.

Human mature neurons from primary cultures of normal embryonic neural progenitor cells (Clonetics, NHNP CC-2599, San Diego) at 12-day after plating (long-term cultures were used to ensure that the vast majority of the neuron cells in the plates are postmitotic, terminally differentiated) maintain high levels of both pRB and GrB-NIC as determined by immunocytochemical staining (FIG. 6). RT-PCR analysis indicated that GrB-NIC mRNA from human neuronal cells indeed contained the upstream AUG codon, identical to the endogenous granzyme B (GrB-NIC) mRNA in Saos-2 osteosarcoma cells upon pRB-mediated senescent arrest (FIG. 10).

Example 9

Mutation of GrB-NIC Extends Survival of Nerve Cells in RB-deficient Mouse Embryos Intercrossing $GrB^{-/-}$ and $RB^{+/-}$ mutant mice to generate double-homozygous mutant ($GrB^{-/-}$, $RB^{-/-}$) mouse embryos. As homozygous RB mutant ($RB^{-/-}$) mice die in mid-gestation, mice heterozygous for RB deletion mutation ($RB^{+/-}$) were used. According to Heusel et al., in the vector used for lymphocyte GrB gene targeting in ES cells, a genomic DNA fragment containing the entire first exon of GrB gene was replaced with a $neo^R$ gene. Thus, the $GrB^{-/-}$ mice are in fact also $GrB$-NIC-$^{-/-}$ mice. Breeder pairs of the C57BL/6J $GrB^{-/-}$ mice and C57BL/6J Rb1 ($RB^{+/-}$) mice were purchased from The Jackson Laboratory. Either $RB^{+/-}$ or $GrB^{-/-}$ mice are viable, show normal development and fertility. CTL derived from $GrB^{-/-}$ mice are able to induce apoptosis of allogeneic target cells, but with reduced efficiency; the $RB^{+/-}$ mice are susceptible to pituitary and thyroid tumors in late life. These mice were used to obtain double-mutant mice homozygous for both GrB and RB mutations ($GrB^{-/-}RB^{-/-}$, FIG. 12). Briefly, the initial breeding colony was set up to consist of 8 breeding cages. Approximately 3–4 weeks after the breeding colony was set up, such a colony yielded 4–5 F1 heterozygous progeny mice per week. When the F1 progeny reached 3 weeks of age, they were weaned and separated by sex. DNAs were prepared from tail snips of the F1 progenies at the time of weaning (3 weeks of age, 1–1.5 cm tail fragment per offspring), and analyzed for genotype identification. A secondary breeding colony for intercrossing the F1 ($GrB^{+/-}$, $RB^{+/-}$) offsprings was subsequently established. The breeding cages were checked daily and the date of birth, size and weight of each new litter recorded on the cage card. Mice were genotyped by polymerase chain reaction using DNA extracted from tails or from remaining embryonic tissues. The RB and GrB-NIC double-mutant mouse embryos extended survival to approximately embryonic day 20 (E20). The data that have so far been observed strongly supports a physiological role of the novel GrB-NIC of this invention in embryonic, and particularly in early neuronal development. The $GrB^{-/-}$, $RB^{-/-}$ embryos can now be studied directly for detailed hematopoiesis and neural development.

It is known that the central nervous system of the RB mutant ($RB^{-/-}$) embryos exhibit excessive neuronal cell apoptosis. Thus, head or brain, spinal cord and dorsal root ganglia sections from $GrB^{-/-}$, $RB^{-/-}$ embryos are to be examined by TUNEL and BrdU staining to check if absence of GrB-NIC significantly reduces the degree of apoptosis and ectopic DNA synthesis associated with loss of RB function. The frequency of apoptotic cells or ectopically dividing cells are measured as the number of TUNEL-positive or BrdU-positive cells per unit area of tissue in the double mutant embryos compared to RB alone mutants.

Example 10

Comparison of the Numbers, Growth and Differentiation Characteristics of Embryonic Neural Progenitor Cells Derived From Wild-type, $GrB^{+/+}$ $RB^{-/-}$, $GrB^{-/-}$, $RB^{+/+}$, and $GrB^{-/-}/RB^{-/-}$ Mouse Embryos The time and place of a neuron's birth determine its end position and the target connections it will form. Because differentiated neurons do not divide, each one can be assigned a "birthday", defined as the time of the final mitosis that generated it from a dividing neuronal precursor cell. In both higher vertebrates and invertebrates, the birthdays of the neurons of a given type generally all occur within a strictly limited period of development, after which no further neurons of that type are produced. In pivotal studies, caspase 3 has been shown to play a critical role during morphogenetic cell death in the mammalian brain. Deficiency of caspase 3 in mice results in accumulation of supernumerary postmitotic and terminally differentiated neuron cells in the CNS, but does not protect CNS neurons from apoptosis in RB mutant mice. Accordingly, if GrB-NIC secreted by differentiating and differentiated neurons plays a critical role in programmed cell death of neighboring dividing neural progenitors during the early phase of neural development (genesis of neurons), one would predict that GrB-NIC mutant mice may preserve more neural stem cells and/or neural precursor cells in the central nervous system, although these cells are not dividing in vivo.

Primary Cultures of Cortical Progenitor Cells, Neurons, and Neural Stem Cells: For timed pregnancies, mice are bred, and the time of plug identification is counted as embryonic day 0.5 (E0.5). The mice are euthanized at E12.5 and four consecutive embryonic days, and embryos are dissected. To culture progenitor cells, cortices are removed from embryos, triturated, and spheres from each embryo are plated individually on poly-L-ornithine/laminin-coated dishes. The culture medium consisted of neurobasal medium (Life Technologies, Inc.), 0.5 mM glutamine, 50 U/ml penicillin-streptomycin, and 1% N2 supplement. In addition, basic fibroblast growth factor (25 ng/ml, Sigma) is added only upon plating. After 48 h, medium is replaced with the same medium, except 1% N2 supplement is now replaced with 2% B27 (195, 196). After polymerase chain reaction genotyping, the appropriate genotypes (wild-type, $GrB^{+/+}$/$RB^{-/-}$, $GrB^{-/-}/RB^{+/+}$, and $GrB^{-/-}/RB^{-/-}$) are selected for experimentation on day 2 after plating. Rapidly proliferating neural stem cells are isolated from the striatum. At E12.5, the striatum is removed from mouse embryos and triturated to produce a single-cell suspension, Stem cells are plated at a density of $4\times10^4$ cells/ml in Dulbecco's modified Eagle's medium/F-12 medium containing 20 ng/ml basic fibroblast growth factor as described previously. These cells are grown as spheres in suspension, and medium is added on day 3 after trituration. To passage, spheres are again triturated to obtain a single-cell suspension and replated at 4x104 cells/ml. Mature postmitotic neurons are prepared from E17.5 embryos (depending on whether the GrB-NIC deficiency might have the embryos survived longer), from which cortices are collected and triturated in culture medium (Neurobasal medium with 0.5 mM glutamine, 50 units/ml penicillin-streptomycin, 1% N2 supplement, and 2% B27).

Even if the GrB-NIC mutant mice preserve more neural stem cells and/or neural precursor cells in the central nervous system, the microstructure changes may not be grossly revealed by microscopic imaging in tissue sections. The supernumerary $GrB-NIC^{-/-}/RB^{-/-}$ neural stem cells and neural precursor cells, however, might be detected in culture when they are induced to undergo cell division. The $GrB-NIC^{-/-}$ neural progenitor cells, and even the mature neurons, might actually survive better in culture without the cytotoxic effects their own GrB-NIC. To assess these predictions, population analysis is performed as described previously. Briefly, self-maintenance of EGF-responsive precursors is examined in populations in two ways. After 7 days in vitro, spheres grown in flasks are removed, spun down, and resuspended in 2 ml of medium. The spheres are mechanically dissociated into single cells by trituration with a fire-polished Pasteur pipette, an aliquot is counted, and for quantitative determination of the frequency of secondary spheres, 500 cells/200 μl/well are plated in 96-well plates. For long-term passaging, $1\times10^6$ primary EGF-generated cells are plated into a 75-cm tissue culture flask with 20 ml of medium. This procedure is repeated every 6–8 days. The total fold increase in cell numbers through the sequential passages (without losing multilineage potential) will be calculated, and compared with each other (neural cell cultures derived from $GrB^{+/+}/RB^{-/-}$, $GrB^{-/-}/RB^{+/+}$, and $GrB^{-/-}/RB^{-/-}$ embryos), and with those derived from wild-type embryos. In addition, by removing EGF and adding a small amount of FBS, the EGF-responsive neural progenitor cells undergo differentiation after plating onto poly-L-ornithine coated glass coverslips. Indirect immunocytochemistry for neuronal (β-tubulin III and MAP2), glial cell (glial fibrillary acidic protein, or GFAP), and oligodendrocytes (GalC) antigens (172, 173, 196, 197), in combination with morphological examination, are used to characterize the multilineage potential of neural cell cultures derived from F2 embryos of different genotypes.

GrB knockout mice develop normally, so do the mice deficient for E2F-1 or p53. A mutant organism may compensate for the loss of a gene product, which underscore the complexity of modeling gene functions in gene knockout animals. Nevertheless, mouse embryos mutant for both RB and E2F-1, or both RB and p53, demonstrate significant reduction of apoptosis in neurons of the central nervous system compared to RB alone mutants, and extend survival to approximately E17.0. Thus, studies as described here have been well justified. In addition, although the GrB knockout mice develop normally, there might be microstructure changes in the CNS of the mutant mice which have not been to date identified, especially since the majority of previous studies had been focused on the T lymphocytes.

As an alternative approach, there are detailed anatomical data yet to be obtained from the $GrB^{-/-}$ (wild-type RB) mutant mice. Tissue distribution of GrB transcripts in wild-type and $RB^{-/-}$ mouse embryos will be studied by Western blotting, immunohistochemical staining and in situ hybridization (using single-stranded anti-sense RNA probes) to determine if accumulation of endogenous GrB occurs exclusively or mainly in the developing nervous system (in addition to lymphoid cells). The fact that expression of GrB-NIC and Caspase-3 genes overlaps in neural tissues implies that they could be involved in functionally either redundant or non-redundant pathways. The experimental protocols as described should clarify if GrB-NIC and caspase-3 have additional functions independent of each other, and if there is critical requirement for GrB-NIC by neural cells during the early phase of neuronal development (genesis of neurons) as compared with caspase-3 null mutants, whose premature lethality is thought due to lack of neuron cell death in the brain during the relatively late phase of neuronal development (morphogenesis). The caspase 3 deficiency does not protect CNS neurons from apoptosis in RB mutant mice.

Example 11

Design and Methods to Investigate Neural Cell Lineage-specific Requirement for a Precise Endogenous GrB-NIC and pRB Homeostasis During Neuronal Development Examples 11 through 14 provide the rationale and methods for multiplying neural stem cells in vitro by temporal inhibition of their own GrB-NIC activity. The committed neural precursors and differentiating neurons obtained through this procedure can be better used for embryonic neural cell replacement therapy of neurodegenerative diseases.

Although there appears to be a critical requirement for pRB and GrB-NIC during embryonic neural development, it would be premature to conclude that this requirement is lineage specific. The murine embryonic stem (ES) transgenic models have some major draw-back. The function of the gene product must be deduced from the phenotype of animals that are, in the vast majority of cases, deficient throughout ontogeny for the product of the disrupted gene, so that interpretation of the knockout phenotypes is often difficult. Moreover, if the complete loss of a gene product, and the RB-deficient mice in particular, results in embryonic lethality, it precludes monitoring the effect of loss of RB function on other embryonic lineages during later stages of development. Notably, while $RB^{-/-}$ developing neurons undergo excessive apoptosis in vivo, neural precursor cells cultured from RB-deficient embryos appear to differentiate and survive quite normally. Studies of chimeras have also revealed that, embryonic stem cells carrying two inactive RB alleles ($RB^{-/-}$) can contribute substantially to most tissues in adult chimeric mice, including blood, liver and central nervous system, which are severely affected in pure $RB^{-/-}$ embryos. No ostensive abnormalities are seen in the developing and adult CNS of the chimeras. Second, in the study of development and differentiation of higher eukaryotes, especially mammalia, the complexities involved have led to the use of tissue culture systems in order to facilitate more experimental and analytical approaches. In particular, the culture of embryonal carcinoma cells, the stem cells of teratocarcinomas, has allowed the analysis of early commitment and differentiation events analogous to those which occur in small numbers of cells in the early mammalian embryo (see FIG. 13 for a schematic representation). Therefore, more direct evidence for the cell lineage-specific role of GrB-NIC in embryonic neural development may come from knockout pluripotent stem cells in culture. The GrB-NIC knockout P19 stem cell differentiation model offers a unique opportunity to study the lineage- and developmental stage-related role of GrB-NIC without struggling with the complexities of animal models.

Example 11.1

Establishing GrB-NIC Knockout P19 Teratocarcinomas Cell Lines Using a Novel Targeting Vector Designed for Disrupting a Nearly Silent Gene in Target Cells The P19 (ATCC CRL 1825) is a euploid stem cell line derived from a teratocarcinoma induced in a mouse. In contrast to many of the embryonal carcinoma cell lines, P19 can be cloned at high efficiency. These pluripotent cells, which differentiate poorly under normal culture conditions, can be induced to differentiate into neuronal and glial cells in the presence of retinoic acid (RA). In the presence of dimethyl sulfoxide (DMSO), spheroids of P19 cells differentiate rapidly to form large amounts of cardiac and skeletal muscle but no neurons or glia. We therefore propose to disrupt the GrB-NIC (GrB) gene by homologous recombination in P19 cells. The P19 is chosen because it is a perfect diploid (40:XY) cell line, and no more than two 14 chromosomes, where GrB is located, are detected by cytogenetic analysis.

Gene targeting in mammalian cells in culture allows us to study basic questions in cell biology without struggling with the complexities of animal models. A number of recent advances have significantly facilitated gene targeting techniques. Gene targeting for a nearly silent gene, however, represents a new challenge to the standard technique. Promoterless vectors that rely on target gene promoter to express the positive selectable marker enrich homologous recombinants, but they could do so only if the target gene is active in the cell line. We therefore have designed a novel targeting vector (see FIG. 14) for knockout of the GrB-NIC gene that is nearly silent in undifferentiated P19 pluripotent cells. The GrB-NIC gene is known to be activated during RA-induced neuronal differentiation. Instead of using a standard promoterless neoR gene vector, the novel vector contains exon 1 and intron 1 of the mouse GrB genomic sequence and promoterless coding sequence for the modified tetracycline-controlled chimeric transcriptional activator fusion peptide (m-tTA, see FIG. 16) with a polyadenylation site, as well as the modified tTA-dependent promoter (FIG. 16) controlled neoR gene expression cassette. In the knockout cells, a 1182-bp of the GrB fragment is deleted. This corresponds to 6 nucleotides of 3-intron 1, exon 2, intron 2, exon 3, intron 3, exon 4 and 127 nucleotides of 5'-intron 4 of the GrB gene. There are no in-frame ATG codons in the remaining GrB sequences upstream from the translational start site of the tTA fusion peptide. By using this specially designed vector, after homologous recombination, the low-level expression of the m-tTA transactivator driven by the nearly silent native GrB-NIC (GrB) promoter in undifferentiated P19 pluripotent cells can in turn activate the m-tTA-responsive promoter in tetracycline-free environment and thus high-levels of G418-resistent gene expression. In pilot studies, when the 5'-flanking sequence of the murine GrB gene was inserted upstream the promoterless mtTA cassette, the vectors can indeed express significantly higher levels of neoR or CAT activity in exponentially growing P19 cells in Tc-free medium as compared with the same vector without the m-tTA cassette. Two novel targeting vectors, each containing a geneticin- or hygromycin-resistance gene are used to sequentially disrupt the two GrB alleles in P 19.

Example 11.2

Establishing a Two-alternative (Neurons and Muscles) Differentiation Model In Vitro Using the Parental and GrB-NIC Knockout P19 Pluripotent Stem Cells To maintain cultures of P19 EC cells in their undifferentiated state they must remain in exponential growth phase. It is essential to clone cells periodically and to maintain them in exponential growth to ensure that each cell in the population maintains its developmental potential. After GrB-NIC knockout, same approach is applied to select best clones for the differentiation model, and the methods are routinely used in our laboratory. Briefly, a dispersed population of cells will be plated out at a density of 100–200 cells per 100-mm dish in medium containing 0.1 mM.-mercaptoethanol. After 4–6 h of incubation to allow the cells to firmly attached to the plastic surface, and single cells are then picked up by cloning cylinders. As the single-cell cultures grow up, exponentially growing cultures will be prepared for long-term storage in liquid nitrogen.

When aggregated and exposed to 0.3 µM RA, the GrB-NIC knockout P19 clone cells differentiate and develop large numbers of neurons and astrocytes in addition to relatively small numbers of fibroblast-like cells (oligodendroglia). Cells with long processes become evident 1 or 2 days after the spheroids are plated onto the tissue culture surface. These cells have been identified as cholinergic neurons (Note: In the central nervous system, cholinergic neurons are found in several different locations of the brain, including the striatal complex, the basal forebrain, the diencephalon, pontomesencephalic cell groups, and the medulla. It is this cholinergic system, among others, that has been shown to suffer serious neurodegeneration in Alzheimer's disease). The proportion of neurons to non-neuronal cells is initially very high, but the non-neuronal cells proliferate and eventually become more numerous than the neurons. Amongst these non-neuronal cells are the precursors to astrocytes. To produce a population consisting primarily (greater than 90%) of neurons, 1 to 2 days after the spheroids are plated, replace the medium with fresh medium containing 5 µg/ml cytosine arabinoside. This treatment kills the proliferating non-neuronal cells including precursors to astrocytes, and a neuron-enriched population is obtained by day 8 or day 9. Spheroids of P19 cells formed after exposure to medium containing 0.5–1.0% (v/v) DMSO for the 4-day culture in the aggregated state, differentiate into a spectrum of cells which include mainly cardiac and skeletal muscle, but do not include neurons or astrocytes. Differentiated cells derived from GrB-NIC knockout P19 EC cells are identified by immunostaining of lineage-restricted markers, such as neurofilament, β-tubulin III and MAP2 for neurons, GFAP for glia cells, GalC for oligodendroglia, and muscle myosin for skeletal and cardiac muscles.

The effects of GrB-NIC knockout phenotypes in P19 pluripotent stem cells are examined. If GrB-NIC produced by differentiating neurons is responsible for developmental neuronal cell death during genesis of neurons in vivo, the RA-treated GrB-NIC knockout P19 neural precursor cells may survive, divide, and differentiate better in culture without suffering the cytotoxicity of GrB-NIC secreted by their neighboring advanced differentiating neuronal cells. This possibility is tested by the same population analysis as described above, and the results as measured by total fold increase in cell numbers through the sequential passages are compared with wild-type GrB-NIC P19 cell cultures treated with RA in parallel. In addition, the percentage apoptotic or dividing (as measured by BrdU-positive incorporation) cells are analyzed by dual-parameter fluorescence-activated cell sorting (FACS).

Example 11.3

Examining the Effects of Functionally Ablating the RB Family Proteins in Parental and GrB-NIC Knockout P19 Stem Cell Differentiation Models at Different Stages $RB^{-/-}$ neural precursor cells from RB-deficient embryos are able to differentiate and survive in vitro, but exhibit an upregulation of p107, one of the RB family proteins, suggesting that p107 may partially compensate for the loss of pRB in neural precursor cells. As also demonstrated, by functionally ablating the RB family proteins (that is, infection with AdV.tTAΔE1a), including p107, the RA-treated, differentiating P19 neuronal cells (GrB-NIC$^{+/+}$) underwent massive apoptosis that is associated with expression of GrB-NIC. Therefore, experiments are set up to ablate the RB family proteins by infection of wild-type (GrB-NIC$^{+/+}$) and GrB-NIC knockout (GrB-NIC$^{-/-}$) P19 cultures with AdV.tTAΔE1a at MOI of 30 to 50; cultures at different differentiation directions and stages will be included, that is, exponentially growing, undifferentiated P19 cells; RA- or DMSO-treated P19 spheroids at day 2, day 4, at the time of plating (starting differentiation), and 2-, 4-, 6-, 8- and 10-day after plating (long-term cultures are used to ensure that the vast majority of the cells in the plates are postmitotic, terminally differentiated; and in the case of neuronal differentiation, two days after spheroids are plated, 5 µg/ml cytosine arabinoside treatment is applied in parallel to obtain neuron-enriched populations). All experiments are performed at least in triplicate. Apoptotic cell death is visualized by TUNEL staining, and quantitatively measured by dual-parameter FACS analysis. The following scenarios serve as useful guidelines to interpret the data to be obtained: 1) if functionally ablating the RB family proteins in parental (GrB-NIC$^{+/+}$), but not GrB-NIC knockout (GrB-NIC$^{-/-}$) P19 cells exhibits large increases in apoptosis, the results suggest that endogenous GrB-NIC activity might be responsible for excessive neuronal cell death in RB-deficient embryos; 2) if functionally ablating the RB family proteins in RA-treated, but not DMSO-treated differentiating parental (GrB-NIC$^{++}$) P19 cells results in larger increase in apoptosis, and there are no significant differences in apoptotic rates of RA-treated and DMSO-treated GrB-NIC knockout (GrB-NIC$^{-/-}$) P19 cell cultures, the data, taken together, would suggest that the requirement for endogenous GrB-NIC to regulate apoptosis during embryonic development is neuronal cell lineage (and perhaps also other restricted cell lineages)-specific; and 3) finally, if functionally ablating the RB family proteins in parental (GrB-NIC$^{+/+}$), but not GrB-NIC knockout (GrB-NIC$^{-/-}$) terminally differentiated, mature neurons induces apoptosis, it implies that an excessive accumulation of the endogenous GrB-NIC activity, or failure to maintain the high steady-state levels of total RB protein, in neuronal cells late in life could potentially contribute to degenerative neurological disorders.

Cultures infected with AdV.tTA.ΔE1a under non-permissive (medium containing 0.1 µg/ml tetracycline) condition, or with another vector, AdVtTA.β-gal, consisting of the same tetracycline-regulated adenovirus backbone but carrying a lacZ reporter expression cassette, which has also been constructed in our laboratory, are used as controls.

The principal barrier to facile manipulating the mammalian genome by homologous recombination (HR) is not the low frequency of HR, but rather the high frequency of nonhomologous integration. Positive-negative selection—the most commonly used approach—works well in mouse embryonic stem (ES) cells and has made gene targeting fairly routine in these cells. Moreover, the ES cells can still enter the germline after such genetic manipulation in culture. The positive-negative selection vectors typically achieve enrichments of only 2–5-fold, while the promoterless vectors used in this protocol typically achieve enrichments of 100–500-fold for homologous recombination events. P19 is a mouse embryonal carcinoma (EC) stem cell line. As an alternative strategy, an adenovirus vector, AdV.tTASPI-6, is constructed as will be described in detail in Example 13, is used for transient inhibition of endogenous GrB-NIC activity in differentiating and differentiated P19 cells (in two different differentiation directions).

Example 12

Design and Methods to Demonstrate that Temporal Inhibition of Endogenous GrB-NIC by Adenovirus-mediated Delivery of a Serine Protease Inhibitor, SPI-6 (the Murine Counterpart of Human Protease Inhibitor-9), can Promote the Survival of Neuronal Progenitor Cells Early in Culture: Implications in Neural Cell Replacement Therapy Neural stem cells (NSCs), defined as self-renewing, propagatable primordial cells each with the capacity to give rise to differentiated progeny within all neural lineages in all regions of the neuraxis, have recently been identified in the mammalian CNS, including humans, at stages from fetus to adult in a surprisingly wide range of regions.

During the past 10 years, some of the genetic causes of many of the primary neurodegenerative diseases have been found. These diseases have many pathological mechanisms in common, and there may be relatively few pathways to neuronal death seen in these disorders.

As a result, replacement of cells in the brain by neural stemlike cell transplants is being explored as a new therapeutic strategy for such diseases, which include Alzheimer's disease, Parkinson's disease, and so on. But the wider clinical use of embryonic neural stem cells is problematic, not only from an ethical point of view but also because fetal tissue is potentially in limited supply. Concerns related to increasing our ability to multiply neural stem cells in vitro before transplantation are now being addressed by the convergence of disciplines interested in neural cell replacement therapy.

Even though there might be a critical requirement for GrB-NIC in neural cells in vivo during embryonic development and in adult life, the existence of this endogenous GrB-NIC may have created significant obstacles to long-term culturing neural stem cells. The Example 13 and 14 below are to demonstrate that temporal inhibition of GrB-NIC by a specific GrB-NIC inhibitor can promote the survival of neuronal progenitor cells early in culture The new techniques, that is, multiplying neural stem cells in vitro by transient inhibition of GrB-NIC activity in differentiating neurons, has practical implications for embryonic cell replacement therapy of neurodegenerative diseases. On the other hand, one would also need to recommend caution in using permanent GrB-NIC gene knockout neural progenitor cells for transplantation, since GrB-NIC activity might be needed later by the neuronal cells derived from these precursors in order to complete their migration and differentiation in vivo.

Example 13

Construction of a Tc-regulatable Adenovirus Vector, AdVtTA.SPI-6, Expressing SPI6 Serine Protease Inhibitor SPI6 is an ideal natural GrB-NIC (GrB)-Specific Inhibitor. A defense mechanism has recently been reported for T lymphocytes, particularly CTLs, involving a human intracellular serine proteinase inhibitor (serpin), proteinase inhibitor 9 (PI-9). This serpin efficiently inhibits GrB in vitro and in vivo, and cells transfected with a PI-9 expression vector are protected against CTL GrB-mediated apoptosis. Therefore, PI-9 appears to protect CTLs against death induced by their own GrB. Similar observations were reported for the murine counterpart of PI-9, SPI-6. Like PI-9, SPI-6 binds irreversibly to purified GrB and granules from murine CTLs, which can be visualized on SDS/PAGE as a "shifted" complex. The brain tissue, however, has undetectable SPI-6, suggesting that differentiated neural cells protect themselves from apoptosis induced by their own GrB-NIC by maintaining high steady-state levels of endogenous pRB, instead of using SPI-6.

In addition, the inability to reliably express foreign proteins in postmitotic neurons has hampered numerous studies in the field of neurobiology. Within the past several years, however, a number of viral vectors that overcome this problem have been developed. In particular, recombinant adenoviruses have proved to be efficient, non-cytotoxic vectors for manipulating neurons in dissociated and organotypic cultures. It was reported that recombinant adenovirus can be used at titers sufficiently high to transduce the majority of the neuronal population without perturbing survival, electrophysiological function, or cytoarchitecture.

Construction of AdVtTA.SPI-6. We therefore chose to a construct a Tc-regulatable adenovirus vector expressing SPI-6 in neural cells. Procedures for construction of the AdVtTA.SPI-6 adenovirus vector are essentially as described (Hu, et al., 1997. ), and are diagramed in FIG. 15. Briefly, both the modified tTA expression cassette and the tetracycline-responsive SPI-6 expression cassette are inserted into the E1 shuttle plasmid p)E1sp1A which retains the Ad5 packaging signal sequence (P). The resultant recombinant shuttle plasmid p)E1. tTA.SPI-6 and the Ad5 master plasmid, pBHG10 are then co-transfected into 293 cells in 24-well tissue culture plates. The pBHG10 plasmid contains the backbone of the circular Ad5 genome with partial deletion of both E1 (0.5–3.7 m.u.) and E3 (77.5–86.2 m.u.) sequences. The E1 deletion in pBHG10 removes the P packaging signal. Co-transfection of 293 cells with plasmids p)E1. tTA.SPI-6 and pBHG10 produced infectious virions by in vivo recombination, in which the P sequence, the modified tTA expression cassette and the tetracycline-responsive SPI-6 expression cassette are rescued into the E1 deletion region (1.0–9.8 m.u.) of the Ad5 genome (FIG. 15). Presence of infectious adenoviruses as initially demonstrated by cytopathic effect (CPE) will be examined. Cell culture supernatants are collected from the transfected 293 cells in which CPE has occurred. Recombinant viruses are further identified by restriction enzyme digestion mapping and by transducing cells in culture followed by immunocytochemical staining and Western blotting analysis of SPI-6 expression under both permissive (medium without tetracycline) and non-permissive (medium containing 0.1 µg/ml tetracycline) conditions. The AdVtTA.SPI-6 virus is further purified by three rounds of limited dilution of the virus supernatant. Stocks of the virus are prepared by ultracentrifugation banding. Before use, each batch of the adenovirus stocks is evaluated for the absence of replication-competent adenovirus.

The full-length SPI-6 cDNA will be synthesized by RT-PCR using total RNAs extracted from mouse cytotoxic T cell line, MTL2.8.2 as the template. Primers are designed on the basis of the published SPI6 cDNA sequence (GeneBank U96700). The two primers to be used for the reaction are: the sense primer, 5'-GAAGCTTATCATG (TATACTGATATCGAGATGAACCGCCTCGGTAAG) AATA CTCTGTCTGAAGGA-3' (tagged with 11 amino acids from the carboxyl terminus of VSV G protein just on the N-terminal site of SPI-6 immediate after ATG codon; the antisense primer: 5'-GAAGCTTTGTGTAGTATATGTGTCT-3'. The full-length cDNA fragment is then cloned directly into our modified, single-plasmid Tc-responsive expression vector (FIG. 16) via the additional 5'- and 3'-Hind III sites introduced by the primers.

Example 14

Temporal Inhibition of GrB-NIC by SPI-6 can Promote the Survival of Neuronal Progenitor Cells Early in Culture Primary cultures of cortical neuronal progenitor cells derived from wild-type mouse embryos are used. The progenitor cells growing in EGF+FGF-2 formed spheres of undifferentiated cells can generate neurons, glia, and oligodendrocytes. To passage the spheres, they are titrated to obtain a single-cell suspension and replated. At 14 days of expansion, the progenitor cells will be infected at the time of plating with AdVtTA.SPI-6 at multiplicity of infection (MOI) of 30 to 40, which are sufficient to transduce the majority of the neuronal population without detectable cytotoxicity in the case of β-gal control adenovirus infection. Cultures infected with AdVtTA.SPI-6 under non-permissive (medium containing 0.1 µg/ml tetracycline) condition will be used to establish working parameters for the effective genetic manipulation of the neurons. The AdVtTA.β-gal vector as previously described will also be used as an additional control.

Transgene expression in target cells via an adenovirus vector usually persist for only one week, and over the period of time, levels of the ectopic gene expression are diminished gradually. Therefore, in addition to immunocytochemical staining and Western blotting, expression of the ectopic SPI-6 transgene and endogenous GrB-NIC in AdVtTA.SPI-6-infected neural cell cultures is assessed functionally at intervals of 2 days throughout the post-infection periods by in vitro gel shifting assay using granules purified from mouse cytotoxic T cell line, MTL2.8.2 (a function assay for SPI-6), and by Asp-ase assay (an enzymatic assay for GrB-NIC as previously discussed). The quality of the neuronal differentiation will be evaluated by immunocytochemical staining of neuronal marker β-tubulin III and glia cell marker GFAP.

Prior to adenovirus infection, the neural progenitor cells are pulsed with BrdU for 48 h. Seven days after neural differentiation (plating), the total and BrdU-labeled (both dense and lighter labeled) cells are accounted to calculate the percentage BrdU-positive cells and expansion factors (number of cells at end of culture divided by number of cells plated). If our prediction is correct, that is, differentiating and differentiated neural cells express GrB-NIC to eliminate neighboring dividing neural precursor cells, and temporal inhibition of this endogenous GrB-NIC activity by SPI-6, a GrB-NIC-specific inhibitor, can promote survival of the neuronal progenitor cells, we would expect a higher percentage of BrdU-positive cells and higher expansion factors in neural cell cultures pretreated by AdVtTA.SPI-6 and maintained in permissive (in Tc-free medium) condition for SPI-6 expression, as compared with parallel controls. The major statistical end point of this study are expansion factors and percentage of BrdU-positive cells. All experiments are performed at least in triplicate. The statistical significance of the results is calculated using the two-tailed Student's t test. When the stem cell culture and treatment are conducted under GMP condition, the neural progenitor cell harvests can then be used for cell replacement therapy of neurodegenerative diseases in conjunction with a pre-proved gene therapy protocol.

Example 15

Inhibition of GrB-NIC by SPI-6 can Also Promote the Survival of Mature Neurons Under Genotoxic Stress of β-Amyloid (Aβ)

Alzheimer's disease is a neurodegenerative disorder. An increasing body of evidence suggests the importance of β-amyloid (Aβ) in the initiation/progression of the disease. Studies with cultured neurons treated with toxic forms of aggregated Aβ protein demonstrated neuronal loss by an apoptotic pathway. However, the mechanism by which Aβ causes neuronal apoptosis is not well understood. The transcriptional factor E2F1 has recently been found to mediate death of Aβ-treated cortical neurons in culture. In this connection, the newly defined GrB-NIC promoter contains a potential E2F-like motif, which can be specifically recognized by E2F-1 transcription factor, and accumulation of unphosphorylated (active) free E2F-1 was shown to take place in RB-reconstituted cells expressing GrB-NIC (FIG. 9). It is contemplated that up-regulation of E2F-1 and in turn GrB-NIC might occur in Aβ-treated neurons, and inhibition of GrB-NIC by SPI-6 can promote the survival of mature neurons under genotoxic stress of β-amyloid (Aβ).

Both primary cultures of GrB-NIC$^{+/+}$ and GrB-NIC$^{-/-}$ mature cortical neurons, or terminally differentiated wild-type (GrB-NIC$^{+/+}$) and GrB-NIC knockout (GrB-NIC$^{-/-}$) P19 neurons are treated with Aβ. Two days after initial plating, the medium is exchanged with serum-free medium supplemented with pre-aggregated Aβ(50 μg/ml) (Bachem, Torrence, Calif.). Aβ is pre-aggregated by incubation in serum-free medium at a concentration of 0.2 mg/ml at 37° C. overnight. The Aβ-treated GrB-NIC$^{+/+}$ neuronal cultures are subsequently infected with AdVtTA.SPI-6 at MOI of 30 to 40. Expression of E2F-1 and GrB-NIC (GrB-NIC$^{+/+}$ neurons only) is examined by immune Western blotting. If GrB-NIC-deficient (GrB-NIC$^{-/-}$) neurons can escape from apoptosis induced by exposure to Aβ, or inhibition of endogenous GrB activity by SPI-6 is able to rescue Aβ-treated wild-type (GrB-NIC$^{+/+}$) neurons against cell death as measured by TUNEL assay and DNA fragmentation, the results would suggest that GrB-NIC might be partly responsible for neuronal loss through apoptosis in degenerative neurological disorders, such as Alzheimer's disease.

Example 16

GrB-NIC-associated Apoptosis is Accelerated by Infection With AD, a Substitute for Perforin In terms of lymphocyte granule-mediated target cell apoptosis, a recently revised model suggests that target cells internalize GrB through receptor-mediated endocytosis but require perforin for cytosolic delivery and subsequent apoptosis. It has also been reported that adenovirus (AD), a virus that escapes endosomes to reach the cytosol, can substitute for perforin (Shi et al., 1997; Motyka et al., 2000). Hence, an experiment was undertaken to examine whether AD can accelerate GrB-NIC-mediated apoptosis. Parental Saos-2 (pRB$^-$) tumor cells were mixed with the RB-reconstituted Saos-2 pRB-clone 11 cells that had been grown in Tc-containing or Tc-free medium for 4 days and infected with a replication-deficient adenovirus, AdVβ-gal (AD). Dual-parameter FACS analysis (FIG. 17) revealed that approximate 3 h after AD infection, the percentage of pRB$^+$ sub-G1 cells was increased to 14.4% from 1.37% before AD infection, while the number of pRB$^-$ sub-G1 cells was also increased to 3.72% from 1.69%. The apoptotic nature of the sub-G1 cells was further demonstrated by TUNEL labeling. We found that shortly after AD infection, the percentage of TUNEL-positive (apopiotic) cells increased to 11.8% of the total gated cells from 1.79% before AD infection, and the vast majority of sub-G1 cells (~74.9%) were TUNEL positive (FIGS. 17K & L). Apoptosis of the RB-reconstituted Saos-2 cells after AD infection was also accompanied by site-specific cleavage and subsequent degradation of the RB protein. In contrast, AD infection had no effect in mixed cultures that were maintained in medium containing 0.5 μg/ml of Tc, in which all cells, including both the Saos-2 pRB-clone 11 and the parental Saos-2, were pRB$^-$/GrB-NIC$^-$ (FIG. 17). We conclude that GrB-NIC-associated apoptosis is accelerated by infection with AD, a substitute for perforin, which can facilitate release of GrB-NIC into the cytosol.

Example 17

Detection of Endogenous GrB-NIC in Primary Breast Carcinomas Overexpressing pRB

To address the issue of whether breast cancer cells can produce their own GrB-NIC, a total of 25 randomly selected breast carcinomas were examined for endogenous pRB and GrB-NIC expression. As illustrated in FIG. 18A, by immunohistochemical staining of routinely processed pathological specimens, we found that 5 of the 25 breast tumors were pRB$^-$, i.e., loss of pRB staining occurred in every malignant cell of the tumors. In these pRB$^-$ tumors, some (but not all) of the reactive stromal cells were stained positively for pRB, which was consistent with the view that expression of pRB in normal tissues was regulated by their proliferation and differentiation states. Malignant cells of the five pRB$^-$ breast tumors were all negative for GrB-NIC, although there were clearly GrB$^+$ tumor infiltrating lymphocytes (TILs) in immediately adjacent tumor stroma; the latter served as an excellent internal control for validating the GrB-NIC staining (FIG. 18B). Second, 17 of the 25 cases fulfilled the established criteria for pRB+ tumors, that is, the observed pRB immunoreactivity patterns in these tumors were highly heterogeneous, and the staining intensity was not uniform among the tumor cells, with more or less of the tumor cell nuclei stained positively (FIG. 18C). In the majority (16 out of 17) of the pRB+ cases, all tumor cells stained negatively for GrB-NIC, while TILs in the same tumor sections were GrB+ (FIG. 18D). Third, the remaining three tumors expressed extremely high levels of pRB as determined by their uniformly high intensity of pRB staining (pRB++, FIG. 18E). In these three pRB+ and one pRB+ tumors, GrB-NIC staining was readily detected in many tumor cells as well as in nonlymphoid reactive stromal cells, including endothelial and mesenchymal cells (FIGS. 18F to 18G). The intensity of the endogenous GrB-NIC staining was variable, with some areas exhibiting typical granular or dot-like cytoplasmic and nuclear staining (FIG. 18G). In this small cohort study, the correlation between endogenous GrB-NIC and pRB protein expression in malignant cells appeared to be significant ($p<0.001$, calculated using the Chi-squared method). On the other hand, the number of tumor-infiltrating lymphocytes with GrB+ staining was variable within the same cohort, and in general was unrelated to the pRB status of the tumor specimens (FIGS. 18B, 18D and 18H). Two proven anti-granzyme B antibodies, B18.1 and GrB7, were used for the studies with essentially similar results.

Experimental Procedures

Exemplary experimental procedures and protocols carried out in the above described examples are set forth below. Other protocols incorporated in the above examples would be well known to one of ordinary skill in the art.

Modification of the Tetracycline (Tc)-responsive Gene Expression System.

The original, multi-plasmid tetracycline repressor/operator-based regulatory system was generously provided by Dr. H. Bujard. The tetracycline-responsive transactivator (tTA) used in the system contains the activating domains of the herpes virus protein VP16, which is known to have squelching effects on cell growth. There have been several modified versions of the tetracycline-regulatable gene expression system in the literature, including the tetracycline activation ("tet-on") system (with relatively higher leakiness) and the modified autoregulation system. The latter system, since it up-regulates VP-16 transactivator expression level, further aggravating its squelching effects on host cell growth, may not be quite useful for careful studies on target gene function.

We have thus modified the original VP16 activation domain through site-directed mutagenesis and generated a more potent (but less cytotoxic) version of the chimeric transcriptional activator (m-tTA). Second, we modified the tTA expression cassette by replacing the strong CMVp enhancer with a pair of imperfect direct repeat sequences (mCMVp), lowering the levels of m-tTA expression. The modifications resulted in a m-tTA cassette with no cytotoxic effects on host cell growth (FIG. 16) and further reduced the leakiness of the system; both features are important for validating the use of this system for studies on gene function in a target cell.

We next designed a single plasmid vector, named EC1214A (FIG. 16), which has been used in our laboratory to obtain various stable tumor cell lines in which expression of pRB or wt p53 can be turned on and off without detectable leakage. Our single-plasmid system is readily convertible to tetracycline-controlled adenoviral vectors because the mCMVp is not up-regulated in response to E1a; the latter viral protein is normally expressed in 293 producer cells and is a potent transactivator of the unmodified CMV promoter. The system has allowed us to generate recombinant adenovirus vectors with tetracycline-regulatable TNF-α, I6B, pRB110, pRB94, β-gal, and E1a expression. The latter two virus vectors, that is, AdV.tTA.)E1a and AdVtTA.β-gal are used for some of the studies in the above described examples.

Molecular Cloning of Differentially Expressed Genes in Tumor Cells With Tc-regulated pRB Expression The Tc-regulatable pRB-reconstituted Saos-2 osteosarcoma and MDA-MB-468 breast carcinoma cell lines (Xu et al., 1997) used in the present studies were all early passage sublines following initial plasmid transfection and G418 selection. DD-PCR and UniGEM V microarray assay (GenomeSystems/Incyte) were performed on total RNA or mRNA samples extracted from syngeneic cell lines at their "RB-off" and "RB-on" modes, respectively. A number of cDNA clones representative of active genes in tumor cells in their "RB-on" mode were identified. Primers designed on the basis of partial nucleotide sequences of the candidate genes were then used for 5'- and 3'-rapid amplification of cDNA ends (RACE) to clone the full-length cDNAs according to the user manual (Clontech). The two primers used for cloning the GrB-NIC cDNA were 5'-GGCAGCCTTCCTGAGAAG-3' (sense, for 3'-RACE) and 5'-GCACCTCTCCCAGTGTAAAT-3' (antisense, for 5'-RACE).

RPA and Northern Blot Analysis

Multiprobe template sets for human apoptosis-related genes (hAPO-1; PharMingen) were used for RPA. The assay was conducted according to the RiboQuant system manuals. Templates for L32 and GAPDH housekeeping genes were included to allow assessment of the amounts of total RNAs in each sample. Northern blot analysis was done on total RNA (10 μg/lane for Saos-2 and 2 μg for PBL) or mRNA (2 μg/lane for MDA-MB-468) samples using a $^{32}$P-labeled full-length GrB-NIC cDNA probe, and an actin probe (for rehybridization). After exposure to a storage phosphor screen, quantitative comparison of GrB-NIC transcript levels between the samples was carried out by using a Storm 860 PhosphorImager system and ImageQuant software (Molecular Dynamics), and fold increases in transcription were calculated based on the PhosphorImager counts of GrB-NIC bands adjusted for counts of β-actin bands from the same samples.

Immunostaining, FACS, and Western Blot Analyses

Immunostaining of pRB and GrB-NIC/GrB proteins was carried out with the avidin-biotinylated peroxidase or fluorescence methods (Pinkoski et al., 2000; Zhou et al., 1994). An anti-RB antibody RB-WL-1 (Xu, 1995) and anti-GrB monoclonal antibodies B18.1 or GrB7 (Alexis) were used. For double immunofluorescence analysis of pRB and GrB-NIC, anti-RB monoclonal antibodies G3-245 (mouse IgG1; PharMingen) and B18.1 (mouse IgG2a) were used. Digital images were acquired by CLSM (Zeiss LSM 210). To quantify apoptosis in mixed cultures of pRB+ or pRB− tumor cells by two-color FACS analysis, single-cell suspensions collected under the indicated conditions were fixed with formaldehyde and ethanol, sequentially labeled with fluorescein isothiocyanate (FITC)-conjugated G3-245 and DNA-binding fluorescent dye Hoechst 33342. Dot plots and histograms depicting profiles of fluorescence-labeled cells were generated using FACS Vantage (Becton-Dickinson). Detection of pRB, GrB-NIC/GrB and E2F-1 by Western blotting was done as described (Zhou et al., 1994; Berthou et al., 1997).

Deglycosylation Analysis of GrB-NIC and GrB Proteins by Endo H

The conditions for hydrolysis of N-glycosylated proteins in whole cell lysates by Endo H were optimized based on the general guidelines previously established for deglycosylation of purified glycoproteins (Trimble and Maley, 1984). Briefly, cell extracts were prepared in 50 mM TrisHCl (pH 8.0) containing 120 mM NaCl and 0.5% NP-40, and then changed into 100 mM phosphate reaction buffer (pH 5.8) by using Bio-Spin 6 columns (Bio-Rad). Since deglycosylation rate can be increased by pre-denaturing the glycoproteins, the cell extracts in the case of using denatured substrates were pre-heated for 2 min at 100° C. with 1.2-fold weight excess of sodium dodecyl sulfate (SDS) in relation to the protein contents. The deglycosylation assays were carried out in triplicate in microfuge tubes. Each tube contained 5 μg of total cellular proteins in 25 μl reaction buffer, a cocktail of proteinase inhibitors, 100 mM of β-mercaptoethanol (β-ME), and (Tube 1, Control) without Endo H, or (Tubes 2 & 3) with 10 mU of Endo H (for IL-2-activated PBL). Cell extracts in Tube 2 were pre-denatured. Because MDA-MB-468 pRB-clone 19 in Tc-free medium accumulated a large amount of 39-kDa GrB-NIC protein, 45 mU of Endo H were used in each of the corresponding reactions. All reaction mixtures were incubated for 18 h at 37° C., and then analyzed by Western blotting as described above.

Asp-ase Assay

Cell lysates ($10^7$ cells/ml) were prepared from Saos-2 pRB-clone 11. GrB-NIC proteins were immunoprecipitated from the cell lysates using B18.1 antibody. Immune complexes attached to protein A beads were eluted and assayed for Asp-ase activity using Boc-Ala-Ala-Asp-SBzl substrate (Bzl) (Alexis Biochemicals) (Smyth et al., 1995). The color development was completed at 37° C. for 2 h and was measured at 405 nm using a microplate reader.

Primer Extension, EMS and CAT Assays

The primer extension assay was performed as previously described (Klein et al., 1989). A 20-mer oligonucleotide, 5'-AATCATGCAGTGACCACATC-3', complementary to GrB-NIC 5' untranslated sequence, was end-labeled with ($\gamma$-$^{32}$P)ATP and annealed to 40 μg of total RNAs from each sample, as indicated in FIG. 2C. The primer extension reactions were carried out using the AMV reverse transcriptase (Promega). The products of the chain elongation were analyzed by denaturing polyacrylamide gel electrophoresis. Two additional oligonucleotide primers (5'-AGAAGCAGGATTGGTTGCAT-3' and 5'-AGGCTCAGTGACTTCATGTT-3') complementary to disparate 5' coding and noncoding sequences were also used for primer extension assay but failed to yield reproducible elongation products.

For EMS assay, a Ban II/Pvu II GrB-NIC promoter fragment (−180 to +15), containing the putative E2F site, was end labeled with ($\alpha$-$^{32}$P)dCTP using Klenow fragment, and 1 ng of the labeled DNA fragment was incubated with cell extracts prepared from pCMV.E2F-1 plasmid-transfected Saos-2 cells. In parallel experiments, unlabeled DNA fragments, containing either wild-type or mutated E2F site (−118 G to A), were added as competitors. The DNA-protein complexes were separated on a polyacrylamide gel.

The relative promoter strength was analyzed by measuring expression of the CAT reporter gene after transfection of various promoter-CAT constructs as indicated in FIG. 6B. Cells were harvested 48 h after transfection, and nonradioactive CAT assay, including visual analysis of the thin-layer chromatography (TLC) plates and quantitative analysis of the acetylated products was done according to the technical manual (Stratagene).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically and expressly incorporated herein by reference.

An, B., and Dou, Q. P. (1996). Cleavage of retinoblastoma protein during apoptosis: an interleukin 1 beta-converting enzyme-like protease as candidate. Cancer Res. 56, 438–442.

Babichuk, C. K., Duggan, B. L., and Bleackley, R. C. (1996). In vivo regulation of murine granzyme B gene transcription in activated primary T cells. J. Biol. Chem. 271, 16485–16493.

Berthou, C., Marolleau, J. P., Lafaurie, C., Soulie, A., Dal Cortivo, L., Bourge, J F, Benbunan, M., and Sasportes, M. (1995). Granzyme B and perforin lytic proteins are expressed in CD34$^+$ peripheral blood progenitor cells mobilized by chemotherapy and granulocyte colony-stimulating factor. Blood 86, 3500–3506.

Berthou, C., Michel, L., Soulie, A., Jean-Louis, F., Flageul, B., Dubertret, L., Sigaux, F., Zhang, Y., and Sasportes, M. (1997). Acquisition of granzyme B and Fas ligand proteins by human keratinocytes contributes to epidermal cell defense. J. Immunol. 159, 5293–5300.

Bignon, Y. J., Chen, Y., Chang, C. Y., Riley, D. J., Windle, J. J., Mellon, P. L., and Lee, W. H. (1993). Expression of a retinoblastoma transgene results in dwarf mice. Genes Dev. 7,1654–1662.

Brehm, A., and Kouzarides, T. (1999). Retinoblastoma protein meets chromatin. Trends Biochem. Sci. 24, 142–145.

Bruno, A. P., Lautier, D., d'Orgeix, A. T., Laurent, G., and Quillet-Mary, A. (2000). Acute myeloblastic leukemic cells acquire cellular cytotoxicity under genotoxic stress: implication of granzyme B and perforin. Blood 96, 1914–1920.

Campisi, J. (1996). Replicative senescence: an old lives' tale? Cell 84, 497–500.

Chen, P. L., Chen, Y., Shan, B., Bookstein, R., and Lee, W. H. (1992). Stability of retinoblastoma gene expression determines the tumorigenicity of reconstituted retinoblastoma cells. Cell Growth Differ. 3, 119–125.

Chen, W. D., Otterson, G. A., Lipkowitz, S., Khleif, S. N., Coxon, A. B., and Kaye, F. J. (1997). Apoptosis is associated with cleavage of a 5-kDa fragment from RB which mimics dephosphorylation and modulates E2F binding. Oncogene 14, 1243–1248.

Cordon-Cardo, C., and Richon, V. M. (1994). Expression of the retinoblastoma protein is regulated in normal human tissues. Am. J. Pathol. 144, 500–510.

Dyson, N. (1998). The regulation of E2F by pRB-family proteins. Genes Dev. 12: 2245–2262.

Fattman, C. L., An, B., Sussman, L., and Dou, Q. P. (1998). p53-independent dephosphorylation and cleavage of retinoblastoma protein during tamoxifen-induced apoptosis in human breast carcinoma cells. Cancer Letters 130, 103–113.

Graubert, T. A., DiPersio, J. F., Russell, J. H., and Ley, T. J. (1997). Perforin/granzyme-dependent and independent mechanisms are both important for the development of graft-versus-host disease after murine bone marrow transplantation. J. Clin. Invest. 100, 904–911.

Haas-Kogan, D. A., Kogan, S. C., Levi, D., Dazin, P., T'Ang, A., Fung, Y. K., and Israel, M. A. (1995). Inhibition of apoptosis by the retinoblastoma gene product. EMBO J. 14, 461–472.

Heusel, J. W., Wesselschmidt, R. L., Shresta, S., Russell, J. H., and Ley, T. J. (1994). Cytotoxic lymphocytes require granzyme B for the rapid induction of DNA fragmentation and apoptosis in allogeneic target cells. Cell 76, 977–987.

Hirst, C. E., Buzza, M. S., Sutton, V. R., Trapani, J. A., Loveland, K. L., and Bird, P. I. Perforin-independent expression of granzyme B and proteinase inhibitor 9 in human testis and placenta suggests a role for granzyme B-mediated proteolysis in reproduction. Molecular Human Reproduction, 7:1133–1142, 2001.

Hofmann, F., Martelli, F., Livingston, D. M., and Wang, Z. (1996). The retinoblastoma gene product protects E2F-1 from degradation by the ubiquitin-proteasome pathway. Genes Dev. 10, 2949–2959.

Hu, S. X., Ji, W., Zhou, Y. L., Logothetis, C., and Xu, H.-J. (1997) Development of an Adenovirus Vector With Tetracycline-regulatable Human TNF-α Gene Expression. Cancer Res., Advances in Brief, 57: 3339–3343.

Hu S X, Wang S, Wang J P, Mills G B, Zhou Y, Xu H J, (2003) Expression of endogenous granzyme B in a subset of human primary breast carcinomas. Br. J. Can. 89(1): 135–9.

Huang, H. J., Yee, J. K., Shew, J. Y., Chen, P. L., Bookstein, R., Friedmann, T., Lee, E. Y., and Lee, W. H. (1988). Suppression of the neoplastic phenotype by replacement of the RB gene in human cancer cells. Science 242, 1563–1566.

Kennea N L, Mehmet H. J (2002) Neural stem cells, Pathol., 197(4):536–50

Klein, J. L., Shows, T. B., Dupont, B., and Trapani, J. A. (1989). Genomic organization and chromosomal assignment for a serine protease gene (CSPB) expressed by human cytotoxic lymphocytes. Genomics 5, 110–117.

Kontani, K., Sawai, S., Hanaoka, J., Tezuka, N., Inoue, S., and Fujino, S. (2001). Involvement of granzyme B and perforin in suppressing nodal metastasis of cancer cells in breast and lung cancers. Eur. J. Surg. Oncol. 27,180–186.

Krek, W., Xu, G., and Livingston, D. M. (1995). Cyclin A-kinase regulation of E2F-1 DNA binding function underlies suppression of an S phase checkpoint. Cell, 83: 1149–1158.

Lobe, C. G., Finlay, B. B., Paranchych, W., Paetkau, V. H., and Bleackley, R. C. (1986). Novel serine proteases encoded by two cytotoxic T lymphocyte-specific genes. Science 232, 858–861.

McCaffrey, P. G., Luo, C., Kerppola, T. K., Jain, J., Badalian, T. M., Ho, A. M., Burgeon, E., Lane, W. S., Lambert, J. N., Curran, T. et al. (1993). Isolation of the cyclosporin-sensitive T cell transcription factor NFATp. Science 262, 750–754.

Motyka, B., Korbutt, G., Pinkoski, M. J., Heibein, J. A., Caputo, A., Hobman, M., Barry, M., Shostak, I., Sawchuk, T., Holmes, C. F. B., Gauldie, J., and Bleackley, R. C. (2000) Mannose 6-phosphate/insulin-like growth factor II receptor is a death receptor for granzyme B during cytotoxic T cell-induced apoptosis. Cell 103, 491–500.

Odorico, Kaufman, Thomson, (2001) Multilineage Differentiation from Human Embryonic Stem Cell Lines Stem Cells 19: 193–204

Ogura, Y., Martinez, O. M., Villanueva, J. C., Tait, J. F., Strauss, H. W., Higgins, J. P., Tanaka, K., Esquivel, C. O., Blankenberg, F. G., and Krams, S. M. (2001). Apoptosis and allograft rejection in the absence of CD8$^+$ T cells. Transplantation 71, 1827–1834.

Pera M F, (2001)Human pluripotent stem cells: a progress report. Curr Opin Genet Dev (5):595–9

Pinkoski, M. J., Heibain, J. A., Barry, M., and Bleackley, R. C. (2000). Nuclear translocation of granzyme B in target cell apoptosis. Cell Death Differ. 7, 17–24.

Qin, X. Q., Chittenden, T., Livingston, D. M., and Kaelin, W. G., Jr. (1992). Identification of a growth suppression domain within the retinoblastoma gene product. Genes Dev. 6, 953–964.

Romano, G., Micheli, P., Pacilio, C., Giordano, A. (2000) Latest Developments in Gene Transfer Technology: Achievements, Perspectives, and Controversies over Therapeutic Applications Stem Cells 18: 19–39

Schmid, J., and Weissmann, C. (1987) Induction of mRNA for a serine protease and a ∃-thrombo-globulin-like protein in mitogen-stimulated human leukocytes. J. Immunol. 139, 250–256.

Shan, B., Farmer, A. A., and Lee, W. H. (1996). The molecular basis of E2F-1/DP-1-induced S-phase entry and apoptosis. Cell Growth Differ. 7, 689–697.

Shi, L., Mai, S., Israels, S., Browne, K., Trapani, J. A., and Greenberg, A. H. (1997). Granzyme B (GraB) autonomously crosses the cell membrane and perforin initiates apoptosis and GraB nuclear localization. J. Exp. Med. 185, 855–866.

Shresta, S., Russell, J. H., and Ley, T. J. (1997). Mechanisms responsible for granzyme B-independent cytotoxicity. Blood 89, 4085–4091.

Smyth, M. J., McGuire, M. J., and Thia, K. Y. (1995). Expression of recombinant human granzyme B. A processing and activation role for dipeptidyl peptidase I. J. Immunol. 154, 6299–6305.

Sun, J., Whisstock, J. C., Harriott, P., Walker, B., Novak, A., Thompson, P. E., Smith, A. I., and Bird, P. I. (2001). Importance of the P4' residue in human granzyme B inhibitors and substrates revealed by scanning mutagenesis of the proteinase inhibitor 9 reactive center loop. J. Biol. Chem. 276, 15177–15184.

Tan, X., Martin, S. J., Green, D. R., and Wang, J. Y. J. (1997). Degradation of retinoblastoma protein in tumor necrosis factor and CD95-induced cell death. J. Biol. Chem. 272, 9613–9616.

Trapani, J. A., Browne, K. A., Smyth, M. J., and Jans, D. A. (1996). Localization of granzyme B in the nucleus. A putative role in the mechanism of cytotoxic lymphocyte-mediated apoptosis. J.Biol.Chem. 271, 4127–4133.

Trapani, J. A., Klein, J. L., White, P. C., and Dupont, B. (1988). Molecular cloning of an inducible serine esterase gene from human cytotoxic lymphocytes. Proc. Natl. Acad. Sci. U.S.A. 85, 6924–6928.

Trimble, R. B., and Maley, F. (1984) Optimizing hydrolysis of N-linked high-mannose oligosaccharides by endo-∃-N-acetylglucosaminidase H. Analytical Biochem. 141, 515–22.

Wargnier, A., Legros-Maida, S., Bosselut, R., Bourge, J. F., Lafaurie, C., Ghysdael, C. J., Sasportes, M., and Paul, P.

(1995). Identification of human granzyme B promoter regulatory elements interacting with activated T-cell-specific proteins: implication of Ikaros and CBF binding sites in promoter activation. Proc. Natl. Acad. Sci. U.S.A. 92, 6930–6934.

Weissman I L (2000), Translating stem and progenitor cell biology to the clinic: barriers and opportunities. Science, 287(5457): 1442–6.

Wobus A M, Guan K, Pich U., (2001) In vitro differentiation of embryonic stem cells and analysis of cellular phenotypes,: Methods Mol Biol, 158:263–86.

Xu, H.-J. (1995). Altered retinoblastoma (RB) protein expression in human malignancies. Adv. Anat. Pathol. 2, 213–226.

Xu, H.-J., Zhou, Y., Ji, W., Perng, G. S., Kruzelock, R., Bast, R. C., Mills, G. B., Li, J., and Hu, S. X. (1997). Reexpression of retinoblastoma protein induces tumor cell senescence and telomerase inhibition. Oncogene 15, 2589–2596.

Yang, X., Stennicke, H. R., Wang, B., Green, D. R., Janicke, R. U., Srinivasan, A., Seth, P, Salvesen, G. S., and Froelich, C. J. (1998). Granzyme B mimics apical caspases. Description of a unified pathway for transactivation of executioner caspase-3 and -7. J. Biol. Chem. 273, 34278–34283.

Yasukawa, M., Ohminami, H., Arai, J., Kasahara, Y., Ishida, Y., and Fujita, S. (2000). Granule exocytosis, and not the Fas/Fas ligand system, is the main pathway of cytotoxicity mediated by alloantigen-specific CD4(+) as well as CD8(+) cytotoxic T lymphocytes in humans. Blood 95, 2352–2355.

Zhou, Y., Li, J., Xu, K., Hu, S. X., Benedict, W. F., and Xu, H. J. (1994). Further characterization of retinoblastoma gene-mediated cell growth and tumor suppression in human cancer cells. Proc. Natl. Acad. Sci. U.S.A. 91, 4165–4169.

Zandstra P W, Nagy (2001), A Stem cell bioengineering, Annu Rev Biomed Eng., 3:275–305

What is claimed is:

1. An isolated nucleic acid consisting of the nucleic acid sequence of SEQ ID NO: 1, or the complement thereof.

2. An isolated nucleic acid consisting of the nucleic acid sequence of SEQ ID NO: 2, or the complement thereof.

3. A method for producing a non-immune cell granzyme B (GrB-NIC polypeptide, comprising:

(a) transforming or transfecting a host cell with a nucleic acid comprising the nucleic acid sequence of SEQ ID NO: 1, to obtain a transformed or transfected host cell;

(b) culturing the transformed or transfected host cell to obtain a cell culture; and, (c) expressing the nucleic acid in the transformed or transfected host cell;

thereby producing the GrB-NIC polypeptide.

4. The method of claim 3, wherein the host cell is a prokaryotic cell.

5. The method of claim 3, wherein the host cell is a eukaryotic cell.

6. The method of claim 3, wherein said nucleic acid further comprises regulatory necessary to express GrB-NIC polypeptide in a eukaryotic host cell.

7. The method of claim 6, wherein said regulatory elements comprise native GrB-NIC regulatory elements within the nucleic acid sequence set forth in SEQ ID NO:1 from position 1 through position 1031.

8. A vector comprising a cloned nucleic acid, said cloned nucleic acid consisting of the nucleic acid sequence of SEQ ID NO: 1, or the complement thereof.

9. A vector comprising a cloned nucleic acid, said cloned nucleic acid consisting of the nucleic acid sequence of SEQ ID NO: 2, or the complement thereof.

10. The method of claim 3, further comprising isolating the GrB-NIC polypeptide from the host cell or cell culture.

11. The vector of claim 9, further comprising regulatory nucleotide sequence elements necessary to express the encoded GrB-NIC polypeptide in a eukaryotic host cell.

12. The vector of claim 11, wherein said regulatory nucleotide sequence elements comprise native GrB-NIC nucleotide sequence elements within the nucleic acid sequence set forth in SEQ ID NO:1 from position 1 through position 1031.

13. A vector comprising a cloned nucleic acid sequence encoding the amino acid sequence of SEQ ID NO: 3 and further comprising regulatory nucleotide sequence elements necessary to express the encoded GrB-NIC polypeptide in a eukaryotic host cell.

14. The vector of claim 13, wherein said regulatory nucleotide sequence elements comprise one or more native GrB-NIC nucleotide sequence elements within the nucleic acid sequence set forth in SEQ ID NO:1 from position 1 through position 1031.

* * * * *

SEQUENCE LISTING

<160> NUMBER OF SEQ ID NOS: 6

<210> SEQ ID NO 1
<211> LENGTH: 1977
<212> TYPE: DNA
<213> ORGANISM: Homo sapiens

<400> SEQUENCE: 1

```
tcacaagaat cgaaccatgt agagagactt agttgtcttt taacagaatt gggcacgggc      60
tgttcagaaa caacaatctt tcacatccat tataatgata gcattagtgt agtttgttta     120
gcaaatgttt actgtgagcc tgttatgtgc tgagcctgct atgtaagaag tgtggctctc     180
tggacaggag acagaatact aaacaacaca actactgatc tttggctgcc tggcatgctt     240
cctcacttca tatggtatca gcaatttagc accacaaacg tcctttagag aaccagccct     300
ttctcattct tggttctagt ggcttgagta gactgacccc agcctaccca aagtggattt     360
gactcctagc aattcattaa tctagcccaa tccaataaaa tgtcaagtac aggacttttta    420 ttgaaagcat tcagaaaga ggtggactct cacactaaac atttgtaact aaataaggga     480
tgttagaaat tctctagaaa ggaagctatg ataataaatg ggttgctaga tgggtctagt     540
agatggtggc cgtgctttgt tactgccttg tgtattgtgc taccatagcc ctccccaaac     600
tgtactctgg ctcctggcat ttccgtctct tcaaccagat ggtcagctct ctaagtgaag     660
gagacacatc tccaacatgc ttggttctag cacaacagaa gggctcaaac acatacctgc     720
taaagaaact atcctgatgg atttagcagc atggccatga ggcattggcg gttctatcac     780
tgggaactca ggtttctggt gctccagtac ctctactggc tgataccaca tcctacaatt     840
cacttcatag gcttgggttc ctgctctggg ctgaataggt ggtccactct gagtcatcag     900
ctgtgggtga tgatgtggtc actgcatgat tctcacacaa gcacccagag gacgtcatca     960
ggcagaggca gtgggggtgg gcagcattta cagaaaatct gtgatgagac accacaaaac   1020 cagagggaa catgaagtca ctgagcctgc tccacctctt tcctctccca agagctaaaa    1080
gagagcaagg aggaaacaac agcagctcca accagggcag ccttcctgag aagatgcaac   1140
caatcctgct tctgctggcc ttcctcctgc tgccagggc agatgcaggg gagatcatcg   1200
ggggacatga ggccaagccc cactcccgcc cctacatggc ttatcttatg atctgggatc   1260
```

-continued

```
agaagtctct gaagaggtgc ggtggcttcc tgatacaaga cgacttcgtg ctgacagctg    1320
ctcactgttg gggaagctcc ataaatgtca ccttgggggc cacaatatc aaagaacagg     1380 agccgaccca gcagtttatc cctgtgaaaa gacccatccc ccatccagcc tataatccta    1440
agaacttctc caacgacatc atgctactgc agctggagag aaaggccaag cggaccagag    1500
ctgtgcagcc cctcaggcta cctagcaaca aggcccaggt gaagccaggg cagacatgca    1560
gtgtggccgg ctgggggcag acggccccc tgggaaaaca ctcacacaca ctacaagagg     1620
tgaagatgac agtgcaggaa gatcgaaagt gcgaatctga cttacgccat tattacgaca    1680
gtaccattga gttgtgcgtg ggggacccag agattaaaaa gacttccttt aagggggact    1740
ctggaggccc tcttgtgtgt aacaaggtgg cccagggcat tgtctcctat ggacgaaaca    1800
atggcatgcc tccacgagcc tgcaccaaag tctcaagctt tgtacactgg ataaagaaaa    1860
ccatgaaacg ctactaacta caggaagcaa actaagcccc cgctgtaatg aaacaccttc    1920
tctggagcca agtccagatt tacactggga gaggtgccag caactgaata aatacct      1977
```

<210> SEQ ID NO 2
<211> LENGTH: 946
<212> TYPE: DNA
<213> ORGANISM: Homo sapiens
<220> FEATURE:
<221> NAME/KEY: CDS
<222> LOCATION: (1)..(843)
<223> OTHER INFORMATION:

<400> SEQUENCE: 2

```
atg aag tca ctg agc ctg ctc cac ctc ttt cct ctc cca aga gct aaa      48
Met Lys Ser Leu Ser Leu Leu His Leu Phe Pro Leu Pro Arg Ala Lys
 1               5                  10                  15 aga gag caa gga gga aac aac agc agc tcc aac cag ggc agc ctt cct      96
Arg Glu Gln Gly Gly Asn Asn Ser Ser Ser Asn Gln Gly Ser Leu Pro
             20                  25                  30 gag aag atg caa cca atc ctg ctt ctg ctg gcc ttc ctc ctg ctg ccc     144
Glu Lys Met Gln Pro Ile Leu Leu Leu Leu Ala Phe Leu Leu Leu Pro
         35                  40                  45 agg gca gat gca ggg gag atc atc ggg gga cat gag gcc aag ccc cac     192
Arg Ala Asp Ala Gly Glu Ile Ile Gly Gly His Glu Ala Lys Pro His
     50                  55                  60 tcc cgc ccc tac atg gct tat ctt atg atc tgg gat cag aag tct ctg     240
Ser Arg Pro Tyr Met Ala Tyr Leu Met Ile Trp Asp Gln Lys Ser Leu
 65                  70                  75                  80 aag agg tgc ggt ggc ttc ctg ata caa gac gac ttc gtg ctg aca gct     288
Lys Arg Cys Gly Gly Phe Leu Ile Gln Asp Asp Phe Val Leu Thr Ala
                 85                  90                  95 gct cac tgt tgg gga agc tcc ata aat gtc acc ttg ggg gcc cac aat     336
Ala His Cys Trp Gly Ser Ser Ile Asn Val Thr Leu Gly Ala His Asn
            100                 105                 110 atc aaa gaa cag gag ccg acc cag cag ttt atc cct gtg aaa aga ccc     384
Ile Lys Glu Gln Glu Pro Thr Gln Gln Phe Ile Pro Val Lys Arg Pro
        115                 120                 125 atc ccc cat cca gcc tat aat cct aag aac ttc tcc aac gac atc atg     432
Ile Pro His Pro Ala Tyr Asn Pro Lys Asn Phe Ser Asn Asp Ile Met
    130                 135                 140 cta ctg cag ctg gag aga aag gcc aag cgg acc aga gct gtg cag ccc     480
Leu Leu Gln Leu Glu Arg Lys Ala Lys Arg Thr Arg Ala Val Gln Pro
145                 150                 155                 160 ctc agg cta cct agc aac aag gcc cag gtg aag cca ggg cag aca tgc     528
Leu Arg Leu Pro Ser Asn Lys Ala Gln Val Lys Pro Gly Gln Thr Cys
                165                 170                 175
```

```
agt gtg gcc ggc tgg ggg cag acg gcc ccc ctg gga aaa cac tca cac      576
Ser Val Ala Gly Trp Gly Gln Thr Ala Pro Leu Gly Lys His Ser His
        180                 185                 190 aca cta caa gag gtg aag atg aca gtg cag gaa gat cga aag tgc gaa      624
Thr Leu Gln Glu Val Lys Met Thr Val Gln Glu Asp Arg Lys Cys Glu
    195                 200                 205 tct gac tta cgc cat tat tac gac agt acc att gag ttg tgc gtg ggg      672
Ser Asp Leu Arg His Tyr Tyr Asp Ser Thr Ile Glu Leu Cys Val Gly
210                 215                 220 gac cca gag att aaa aag act tcc ttt aag ggg gac tct gga ggc cct      720
Asp Pro Glu Ile Lys Lys Thr Ser Phe Lys Gly Asp Ser Gly Gly Pro
225                 230                 235                 240 ctt gtg tgt aac aag gtg gcc cag ggc att gtc tcc tat gga cga aac      768
Leu Val Cys Asn Lys Val Ala Gln Gly Ile Val Ser Tyr Gly Arg Asn
            245                 250                 255 aat ggc atg cct cca cga gcc tgc acc aaa gtc tca agc ttt gta cac      816
Asn Gly Met Pro Pro Arg Ala Cys Thr Lys Val Ser Ser Phe Val His
        260                 265                 270 tgg ata aag aaa acc atg aaa cgc tac taactacagg aagcaaacta            863
Trp Ile Lys Lys Thr Met Lys Arg Tyr
    275                 280 agcccccgct gtaatgaaac accttctctg gagccaagtc cagatttaca ctgggagagg    923
tgccagcaac tgaataaata cct                                            946

<210> SEQ ID NO 3
<211> LENGTH: 281
<212> TYPE: PRT
<213> ORGANISM: Homo sapiens

<400> SEQUENCE: 3

Met Lys Ser Leu Ser Leu Leu His Leu Phe Pro Leu Pro Arg Ala Lys
1               5                   10                  15

Arg Glu Gln Gly Gly Asn Asn Ser Ser Asn Gln Gly Ser Leu Pro
            20                  25                  30

Glu Lys Met Gln Pro Ile Leu Leu Leu Ala Phe Leu Leu Leu Pro
        35                  40                  45

Arg Ala Asp Ala Gly Glu Ile Ile Gly Gly His Glu Ala Lys Pro His
    50                  55                  60

Ser Arg Pro Tyr Met Ala Tyr Leu Met Ile Trp Asp Gln Lys Ser Leu
65                  70                  75                  80

Lys Arg Cys Gly Gly Phe Leu Ile Gln Asp Asp Phe Val Leu Thr Ala
                85                  90                  95

Ala His Cys Trp Gly Ser Ser Ile Asn Val Thr Leu Gly Ala His Asn
            100                 105                 110

Ile Lys Glu Gln Glu Pro Thr Gln Gln Phe Ile Pro Val Lys Arg Pro
        115                 120                 125

Ile Pro His Pro Ala Tyr Asn Pro Lys Asn Phe Ser Asn Asp Ile Met
    130                 135                 140

Leu Leu Gln Leu Glu Arg Lys Ala Lys Arg Thr Arg Ala Val Gln Pro
145                 150                 155                 160

Leu Arg Leu Pro Ser Asn Lys Ala Gln Val Lys Pro Gly Gln Thr Cys
                165                 170                 175

Ser Val Ala Gly Trp Gly Gln Thr Ala Pro Leu Gly Lys His Ser His
            180                 185                 190

Thr Leu Gln Glu Val Lys Met Thr Val Gln Glu Asp Arg Lys Cys Glu
        195                 200                 205
```

```
Ser Asp Leu Arg His Tyr Tyr Asp Ser Thr Ile Glu Leu Cys Val Gly
        210                 215                 220

Asp Pro Glu Ile Lys Lys Thr Ser Phe Lys Gly Asp Ser Gly Gly Pro
225                 230                 235                 240

Leu Val Cys Asn Lys Val Ala Gln Gly Ile Val Ser Tyr Gly Arg Asn
                245                 250                 255

Asn Gly Met Pro Pro Arg Ala Cys Thr Lys Val Ser Ser Phe Val His
            260                 265                 270

Trp Ile Lys Lys Thr Met Lys Arg Tyr
        275                 280
```

<210> SEQ ID NO 4
<211> LENGTH: 846
<212> TYPE: DNA
<213> ORGANISM: Homo sapiens

<400> SEQUENCE: 4

```
atgaagtcac tgagcctgct ccacctcttt cctctcccaa gagctaaaag agagcaagga      60
ggaaacaaca gcagctccaa ccagggcagc cttcctgaga gatgcaacc  aatcctgctt     120
ctgctggcct tcctcctgct gcccagggca gatgcagggg agatcatcgg gggacatgag    180
gccaagcccc actcccgccc ctacatggct tatcttatga tctgggatca gaagtctctg    240
aagaggtgcg gtggcttcct gatacaagac gacttcgtgc tgacagctgc tcactgttgg    300
ggaagctcca taaatgtcac cttggggggcc cacaatatca agaacagga gccgacccag    360
cagtttatcc ctgtgaaaag acccatcccc atccagcct ataatcctaa gaacttctcc    420
aacgacatca tgctactgca gctggagaga aaggccaagc ggaccagagc tgtgcagccc    480
ctcaggctac ctagcaacaa ggcccaggtg aagccagggc agacatgcag tgtggccggc    540
tggggggcaga cggccccccct gggaaaacac tcacacacac acaagaggt gaagatgaca    600
gtgcaggaag atcgaaagtg cgaatctgac ttacgccatt attacgacag taccattgag    660
ttgtgcgtgg gggacccaga gattaaaaag acttcctta aggggactc  tggaggccct     720
cttgtgtgta acaaggtggc ccagggcatt gtctcctatg gacgaaacaa tggcatgcct    780
ccacgagcct gcaccaaagt ctcaagcttt gtacactgga taaagaaaac catgaaacgc    840
tactaa                                                                846
```

<210> SEQ ID NO 5
<211> LENGTH: 952
<212> TYPE: DNA
<213> ORGANISM: Homo sapiens

<400> SEQUENCE: 5

```
gggaacatga agtcactgag cctgctccac ctctttcctc tcccaagagc taaaagagag     60
caaggaggaa acaacagcag ctccaaccag ggcagccttc ctgagaagat gcaaccaatc   120
ctgcttctgc tggccttcct cctgctgccc agggcagatg caggggagat catcggggga   180
catgaggcca agccccactc ccgccccttac atggcttatc ttatgatctg ggatcagaag   240
tctctgaaga ggtgcggtgg cttcctgata caagacgact tcgtgctgac agctgctcac   300
tgttggggaa gctccataaa tgtcaccttg ggggcccaca atatcaaaga acaggagccg   360
acccagcagt ttatccctgt gaaaagaccc atcccccatc cagcctataa tcctaagaac   420
ttctccaacg acatcatgct actgcagctg gagagaaagg ccaagcggac cagagctgtg   480
cagccctca ggctacctag caacaaggcc caggtgaagc cagggcagac atgcagtgtg   540
```

```
gccggctggg ggcagacggc cccctggga aaacactcac acacactaca agaggtgaag      600
atgacagtgc aggaagatcg aaagtgcgaa tctgacttac gccattatta cgacagtacc      660
attgagttgt gcgtggggga cccagagatt aaaaagactt cctttaaggg ggactctgga      720
ggccctcttg tgtgtaacaa ggtggcccag ggcattgtct cctatggacg aaacaatggc      780
atgcctccac gagcctgcac caaagtctca agctttgtac actggataaa gaaaaccatg      840
aaacgctact aactacagga agcaaactaa gccccgctg taatgaaaca ccttctctgg       900
agccaagtcc agatttacac tgggagaggt gccagcaact gaataaatac ct             952

<210> SEQ ID NO 6
<211> LENGTH: 1091
<212> TYPE: DNA
<213> ORGANISM: Homo sapiens

<400> SEQUENCE: 6
actctgagtc atcagctgtg ggtgatgatg tggtcactgc atgattctca cacaagcacc       60
cagaggacgt catcaggcag aggcagtggg ggtgggcagc atttacagaa aatctgtgat      120
gagacaccac aaaaccagag gggaacatga agtcactgag cctgctccac ctctttcctc      180
tcccaagagc taaagagag caaggaggaa acaacagcag ctccaaccag ggcagccttc      240
ctgagaagat gcaaccaatc ctgcttctgc tggccttcct cctgctgccc agggcagatg      300
caggggagat catcggggga catgaggcca agccccactc ccgcccctac atggcttatc      360
ttatgatctg ggatcagaag tctctgaaga ggtgcggtgg cttcctgata caagacgact      420
tcgtgctgac agctgctcac tgttggggaa gctccataaa tgtcaccttg ggggcccaca      480
atatcaaaga acaggagccg acccagcagt ttatccctgt gaaaaaccca tcccccatcc      540
agcctataat cctaagaact tctccaacga catcatgcta ctgcagctgg agagaaaggc      600
caagcggacc agagctgtgc agcccctcag gctacctagc aacaaggccc aggtgaagcc      660
agggcagaca tgcagtgtgg ccggctgggg gcagacggcc ccctgggaa aacactcaca      720 cacactacaa gaggtgaaga tgacagtgca ggaagatcga aagtgcgaat ctgacttacg      780
ccattattac gacagtacca ttgagttgtg cgtgggggac ccagagatta aaaagacttc      840
ctttaagggg gactctggag gccctcttgt gtgtaacaag gtggcccagg gcattgtctc      900
ctatggacga aacaatggca tgcctccacg agcctgcacc aaagtctcaa gctttgtaca      960
ctggataaag aaaccatga aacgctacta actacaggaa gcaaactaag ccccgctgt      1020 aatgaaacac cttctctgga gccaagtcca gatttacact gggagaggtg ccagcaactg     1080
aataaatacc t                                                           1091
```